(12) United States Patent
Burnett et al.

(10) Patent No.: US 8,858,543 B2
(45) Date of Patent: Oct. 14, 2014

(54) CYROGENIC TREATMENT SYSTEMS

(71) Applicant: Channel Medsystems, Inc., San Francisco, CA (US)

(72) Inventors: Daniel R. Burnett, San Francisco, CA (US); Ric Cote, Oakland, CA (US); William W. Malecki, Piedmont, CA (US); Brian M. Neil, San Francisco, CA (US); David Beaulieu, El Cerrito, CA (US); Benjamin D. Voiles, San Francisco, CA (US)

(73) Assignee: Channel Medsystems, Inc., San Francisco, CA (US)

( * ) Notice: Subject to any disclaimer, the term of this patent is extended or adjusted under 35 U.S.C. 154(b) by 0 days.

(21) Appl. No.: 14/086,088

(22) Filed: Nov. 21, 2013

(65) Prior Publication Data

US 2014/0088579 A1    Mar. 27, 2014

Related U.S. Application Data

(63) Continuation of application No. 13/900,916, filed on May 23, 2013, which is a continuation-in-part of application No. 13/361,779, filed on Jan. 30, 2012.

(60) Provisional application No. 61/462,328, filed on Feb. 1, 2011, provisional application No. 61/571,123, filed on Jun. 22, 2011.

(51) Int. Cl.
| | |
|---|---|
| *A61B 18/02* | (2006.01) |
| *A61B 5/00* | (2006.01) |
| *A61B 5/01* | (2006.01) |
| *A61B 17/12* | (2006.01) |
| *A61B 18/00* | (2006.01) |
| *A61B 18/04* | (2006.01) |
| *A61B 17/00* | (2006.01) |

(52) U.S. Cl.
CPC ............... *A61B 5/01* (2013.01); *A61B 5/4836* (2013.01); *A61B 2018/0022* (2013.01);
(Continued)

(58) Field of Classification Search
USPC ........................................ 606/20–26
See application file for complete search history.

(56) References Cited

U.S. PATENT DOCUMENTS

| | | |
|---|---|---|
| 2,849,002 A | 8/1958 | Oddo |
| 3,924,628 A | 12/1975 | Droegemueller |

(Continued)

FOREIGN PATENT DOCUMENTS

| | | |
|---|---|---|
| WO | WO 98/29068 | 7/1998 |
| WO | WO 02/051491 | 7/2002 |

(Continued)

OTHER PUBLICATIONS

International Patent Application No. PCT/US2012/023176 filed Dec. 19, 2003 in the name of Channel Medsystems, Inc., International Search Report and Written Opinion mailed Jun. 21, 2012.

*Primary Examiner* — Michael Peffley
(74) *Attorney, Agent, or Firm* — Levine Bagade Han LLP

(57) ABSTRACT

Methods and apparatus for the treatment of a body cavity or lumen are described where a heated fluid and/or gas may be introduced through a catheter and into treatment area within the body contained between one or more inflatable/expandable members. The catheter may also have optional pressure and temperature sensing elements which may allow for control of the pressure and temperature within the treatment zone and also prevent the pressure from exceeding a pressure of the inflatable/expandable members to thereby contain the treatment area between these inflatable/expandable members. Optionally, a chilled, room temperature, or warmed fluid such as water may then be used to rapidly terminate the treatment session.

22 Claims, 74 Drawing Sheets

(52) U.S. Cl.
CPC ............... *A61B 2018/00553* (2013.01); *A61B 2018/046* (2013.01); *A61B 2018/0262* (2013.01); *A61B 2017/00539* (2013.01); *A61B 2018/00577* (2013.01); *A61B 18/04* (2013.01); *A61B 2018/00982* (2013.01); *A61B 2018/00011* (2013.01); *A61B 18/0218* (2013.01); *A61B 2018/00488* (2013.01); *A61B 2018/0212* (2013.01); *A61B 18/02* (2013.01); *A61B 17/12022* (2013.01); *A61B 2018/00559* (2013.01)
USPC ............................................. 606/21; 606/23

(56) References Cited

U.S. PATENT DOCUMENTS

| | | | |
|---|---|---|---|
| 4,949,718 A | 8/1990 | Neuwirth | |
| 5,084,044 A | 1/1992 | Quint | |
| 5,334,181 A * | 8/1994 | Rubinsky et al. | 606/22 |
| 5,382,252 A | 1/1995 | Failla | |
| 5,437,665 A | 8/1995 | Munro | |
| 5,501,681 A | 3/1996 | Neuwirth et al. | |
| 5,776,129 A | 7/1998 | Mersch | |
| 5,800,493 A | 9/1998 | Stevens et al. | |
| 5,827,269 A | 10/1998 | Saadat | |
| 5,879,347 A | 3/1999 | Saadat | |
| 5,921,982 A | 7/1999 | Lesh et al. | |
| 5,954,714 A | 9/1999 | Saadat | |
| 6,057,689 A | 5/2000 | Saadat | |
| 6,066,132 A | 5/2000 | Chen et al. | |
| 6,159,160 A | 12/2000 | Hsei et al. | |
| 6,241,722 B1 | 6/2001 | Dobak et al. | |
| 6,280,439 B1 | 8/2001 | Martin et al. | |
| 6,355,029 B1 | 3/2002 | Joye et al. | |
| 6,497,703 B1 | 12/2002 | Korteling et al. | |
| 6,517,533 B1 | 2/2003 | Swaminathan | |
| 6,547,784 B1 | 4/2003 | Thompson | |
| 6,575,932 B1 | 6/2003 | O'brien et al. | |
| 6,589,234 B2 | 7/2003 | Lalonde et al. | |
| 6,602,247 B2 | 8/2003 | Lalonde | |
| 6,607,545 B2 | 8/2003 | Kammerer et al. | |
| 6,648,879 B2 * | 11/2003 | Joye et al. | 606/21 |
| 6,752,802 B1 | 6/2004 | Isenberg | |
| 6,758,831 B2 | 7/2004 | Ryan | |
| 6,875,209 B2 * | 4/2005 | Zvuloni et al. | 606/21 |
| 6,951,569 B2 | 10/2005 | Nohilly | |
| 7,306,589 B2 | 12/2007 | Swanson | |
| 7,500,973 B2 | 3/2009 | Vancelette et al. | |
| 7,566,341 B2 | 7/2009 | Keller et al. | |
| 7,727,228 B2 * | 6/2010 | Abboud et al. | 606/21 |
| 7,794,454 B2 | 9/2010 | Abboud et al. | |
| 2002/0099364 A1 | 7/2002 | Lalonde | |
| 2005/0107855 A1 | 5/2005 | Lennox et al. | |
| 2005/0177148 A1 | 8/2005 | van der Walt et al. | |
| 2006/0259023 A1 | 11/2006 | Abboud et al. | |
| 2007/0088247 A1 | 4/2007 | Bliweis et al. | |
| 2007/0203396 A1 | 8/2007 | Mccutcheon et al. | |
| 2007/0237739 A1 | 10/2007 | Doty | |
| 2009/0076573 A1 | 3/2009 | Burnett et al. | |
| 2009/0138000 A1 | 5/2009 | Vancelette et al. | |
| 2009/0299355 A1 | 12/2009 | Bencini et al. | |
| 2009/0306588 A1 | 12/2009 | Nguyen et al. | |
| 2010/0004595 A1 | 1/2010 | Nguyen et al. | |
| 2010/0049190 A1 | 2/2010 | Long et al. | |
| 2011/0152722 A1 | 6/2011 | Yackel | |
| 2012/0197245 A1 | 8/2012 | Burnett et al. | |

FOREIGN PATENT DOCUMENTS

| | | |
|---|---|---|
| WO | WO 2010/135602 | 11/2010 |
| WO | WO 2012/106260 | 8/2012 |

* cited by examiner

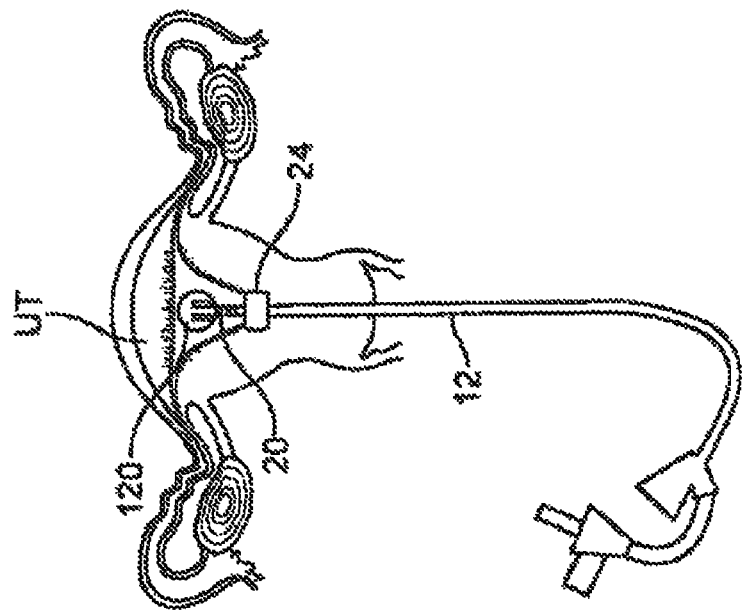
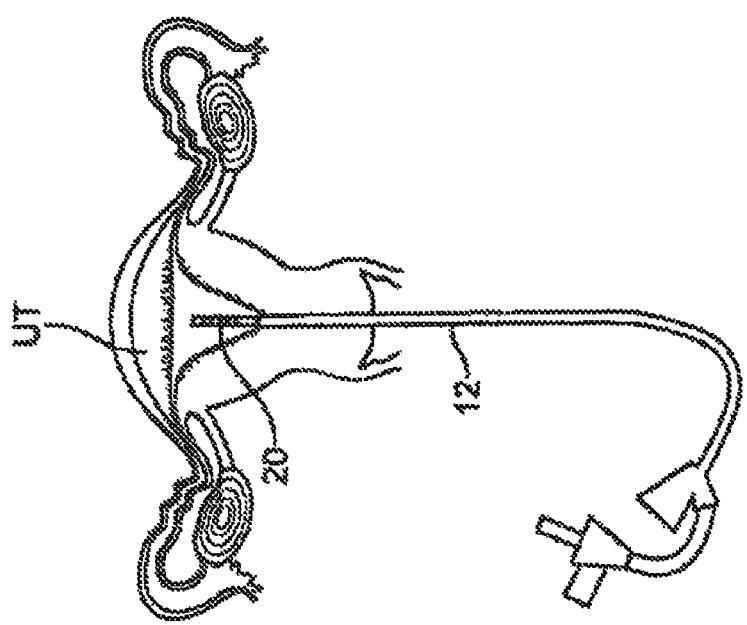

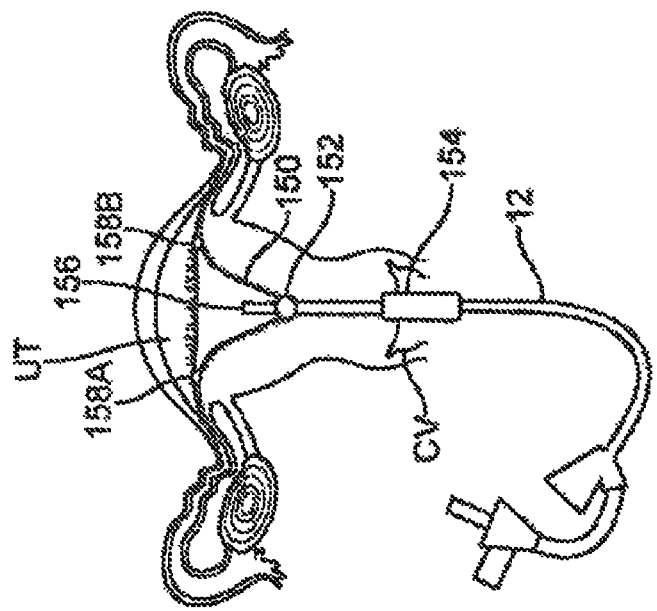
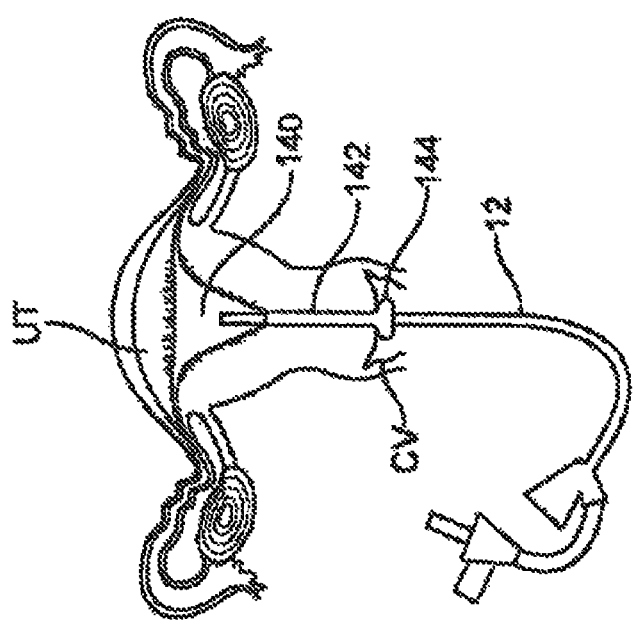

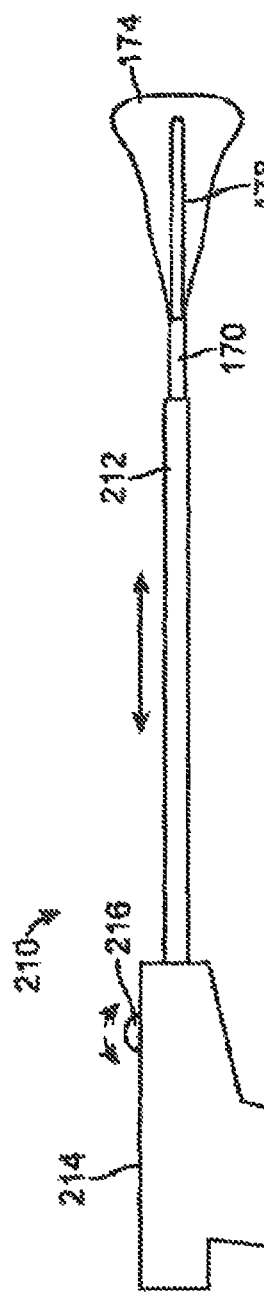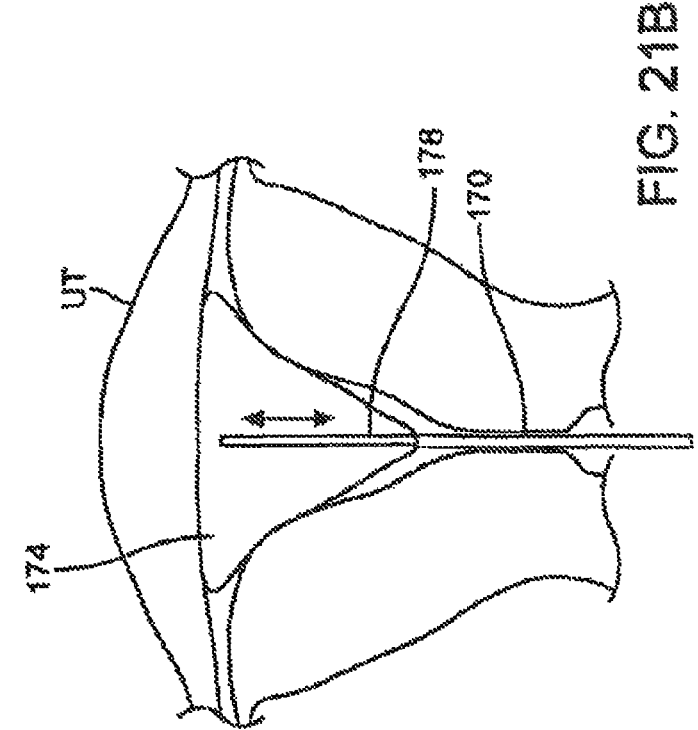
FIG. 21A
FIG. 21B

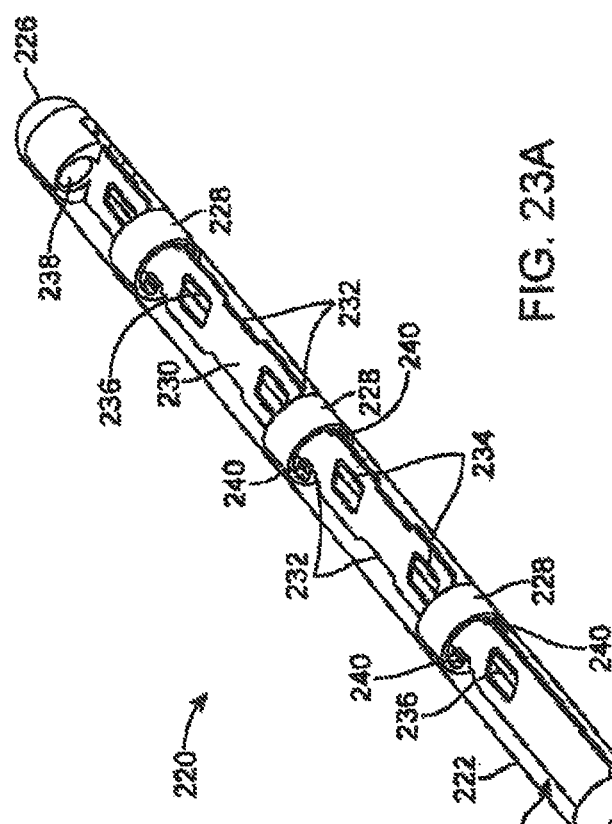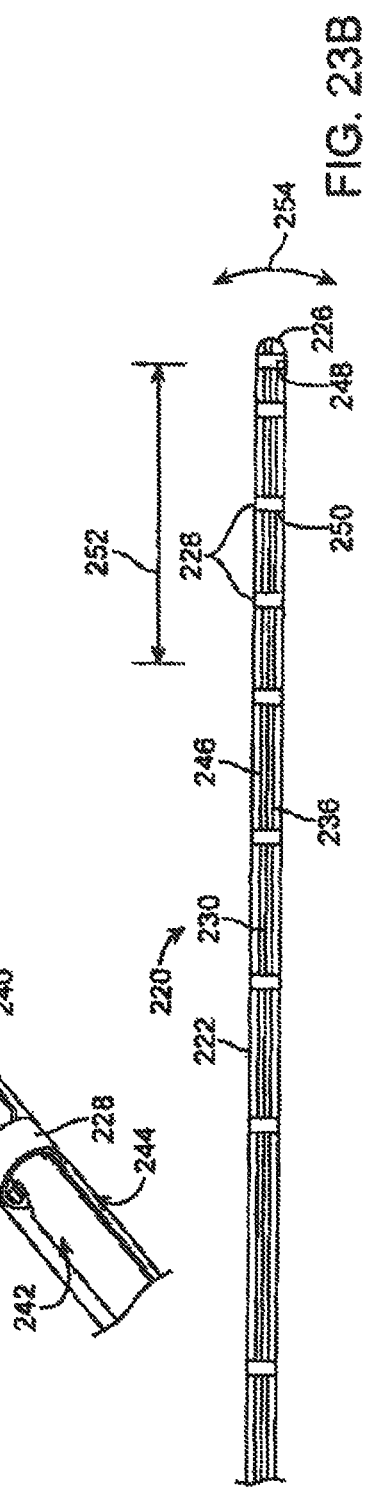

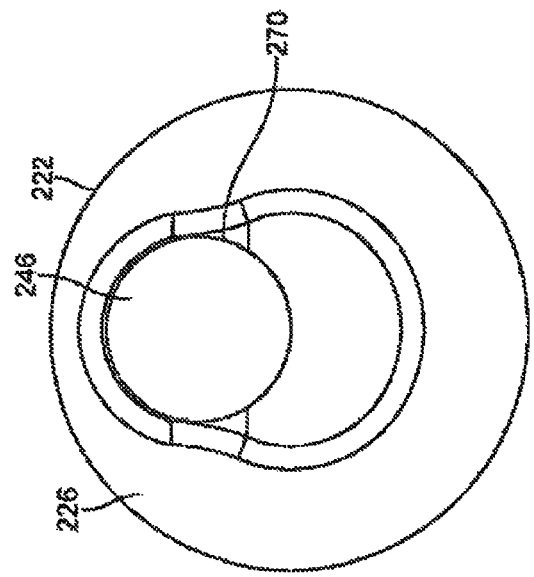
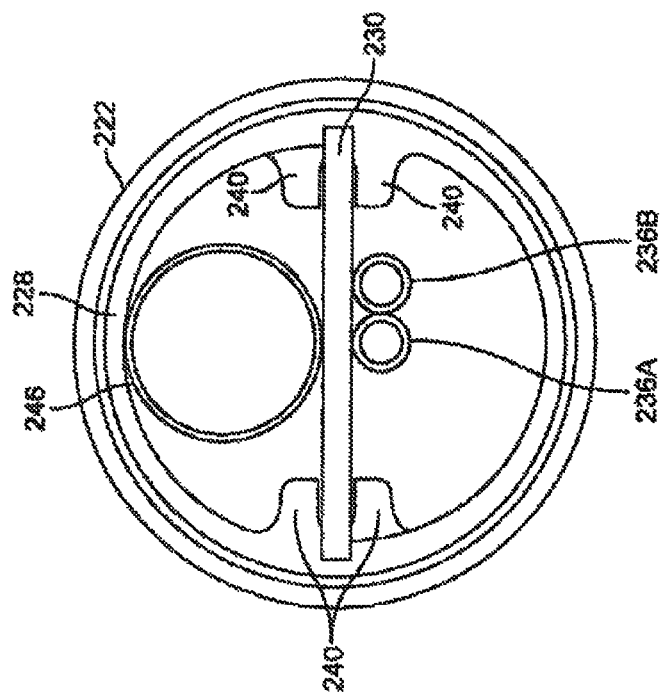

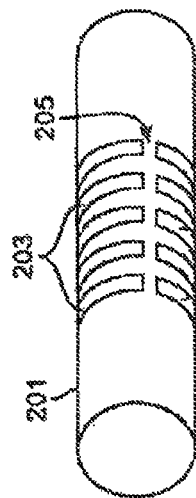
FIG. 26A
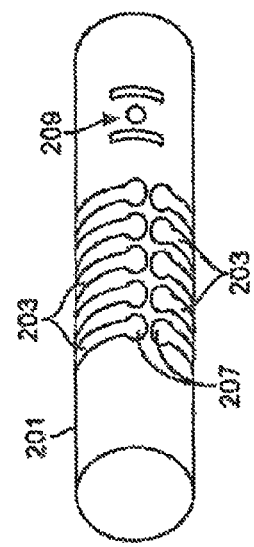
FIG. 26B
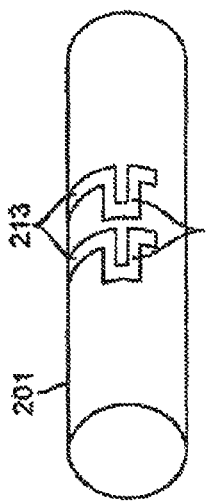
FIG. 26C
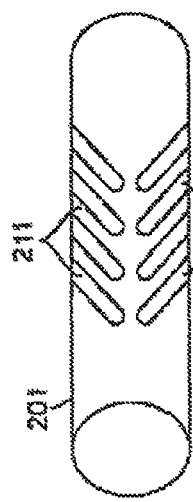
FIG. 26D
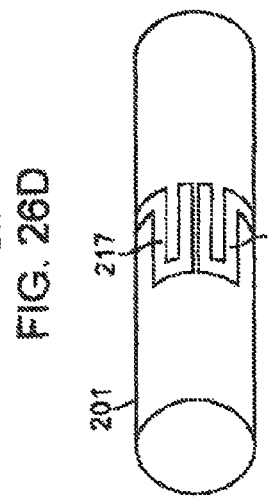
FIG. 26E
FIG. 26F

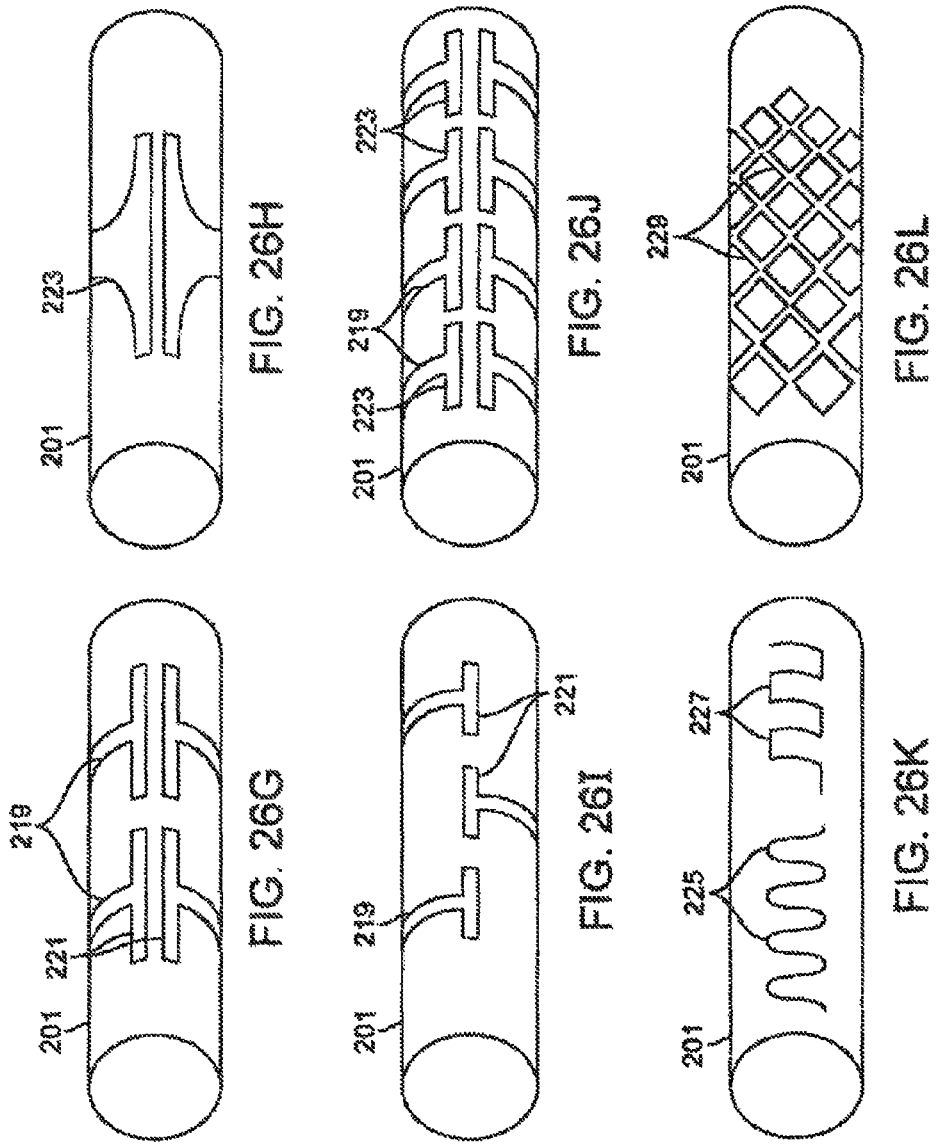

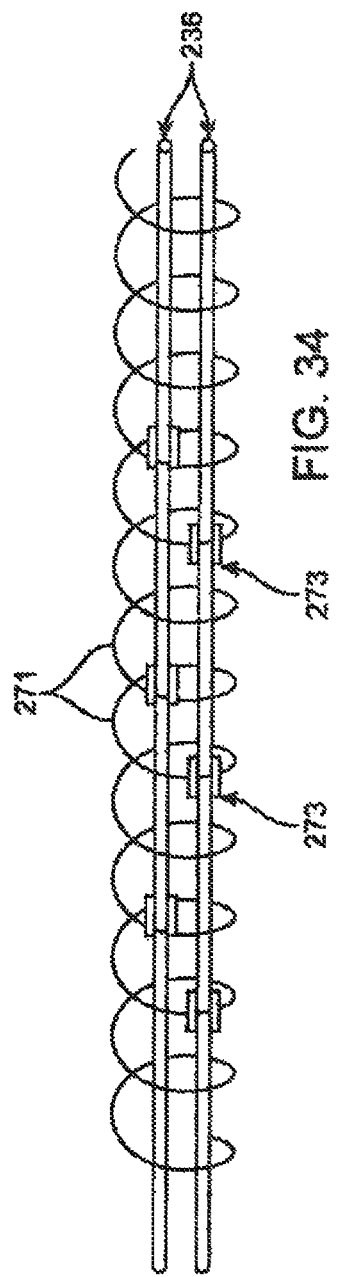
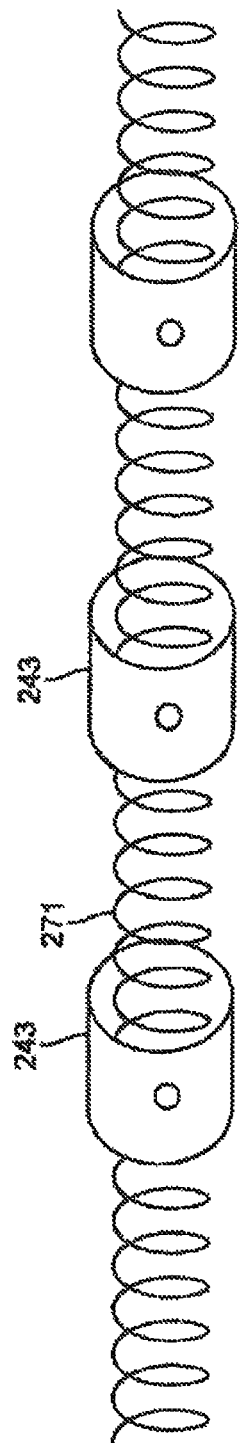
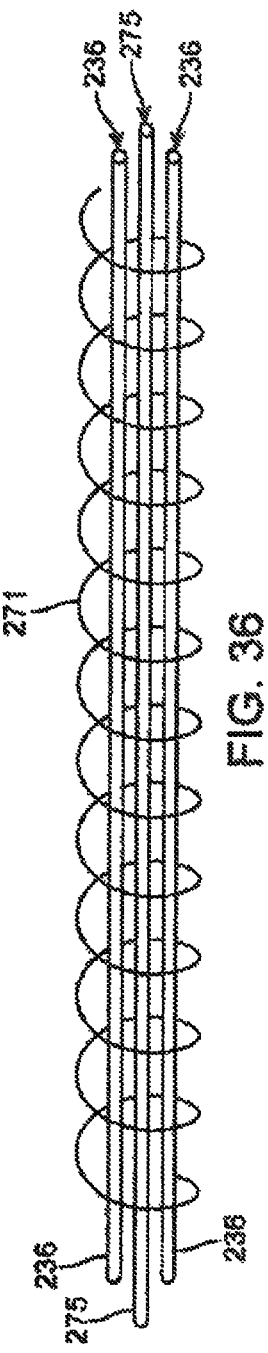
FIG. 34
FIG. 35
FIG. 36

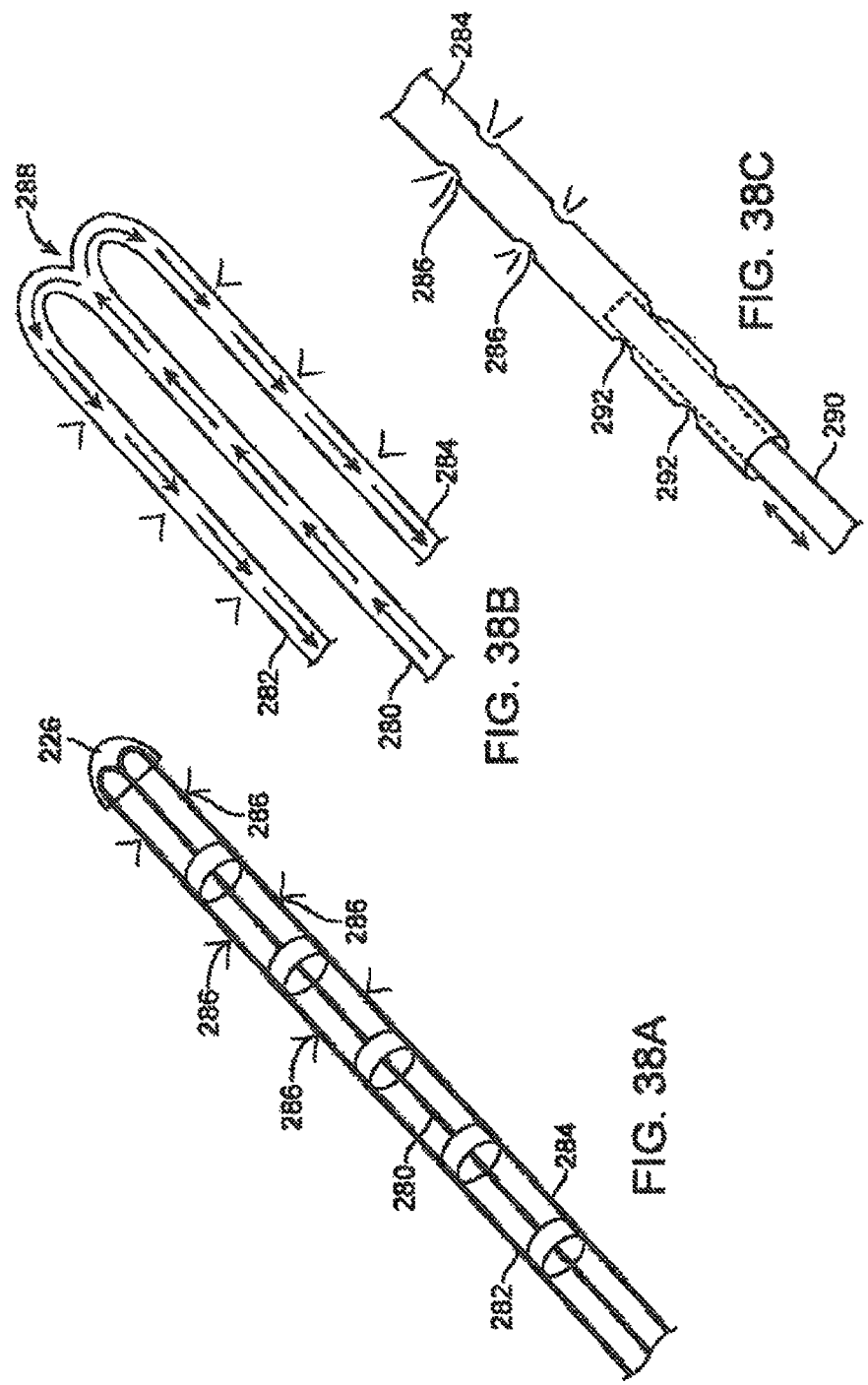

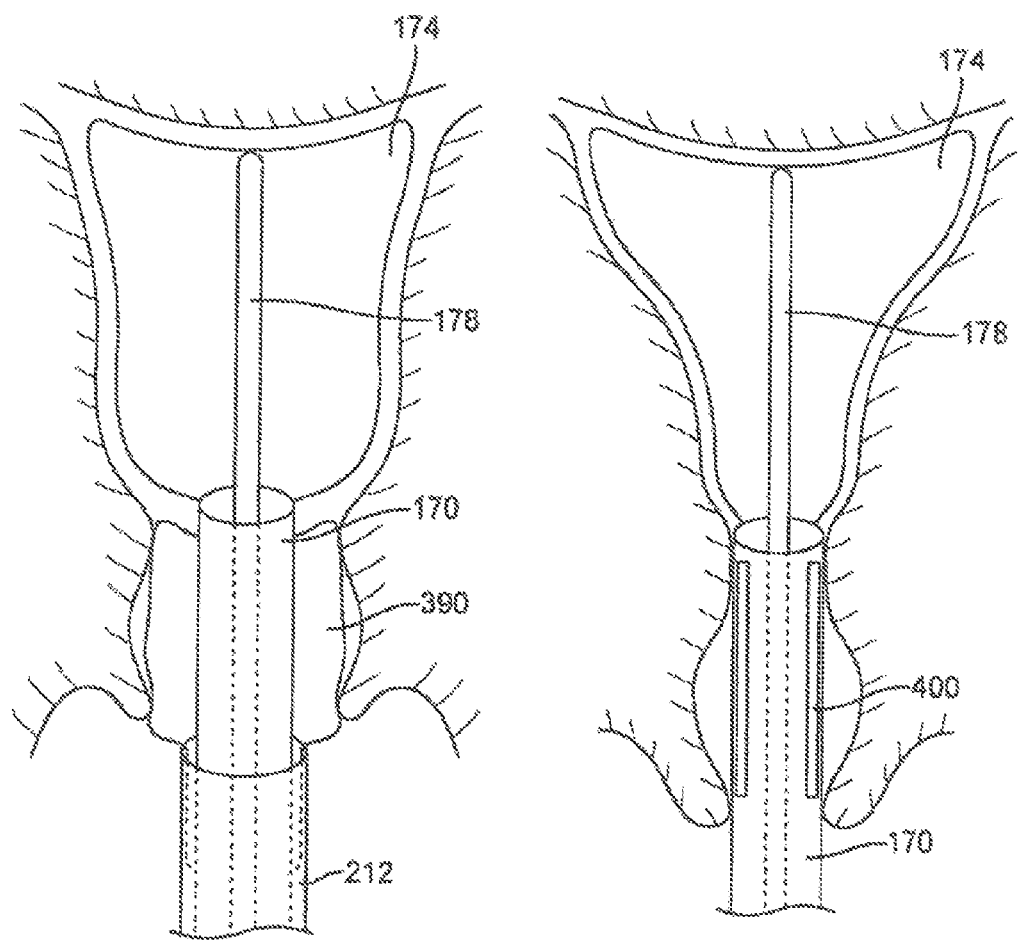

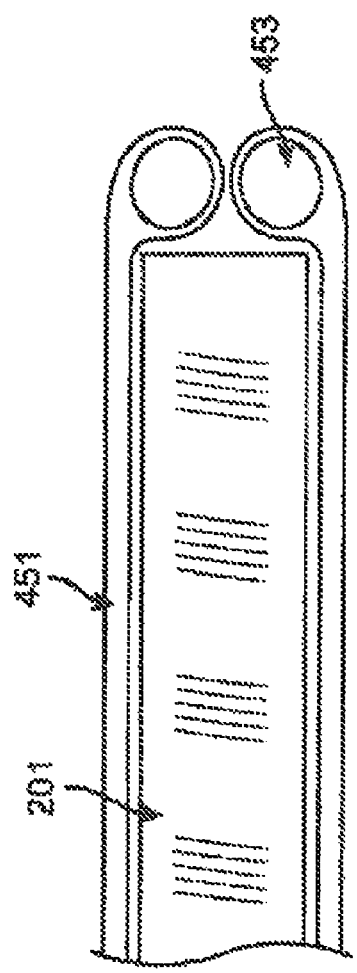
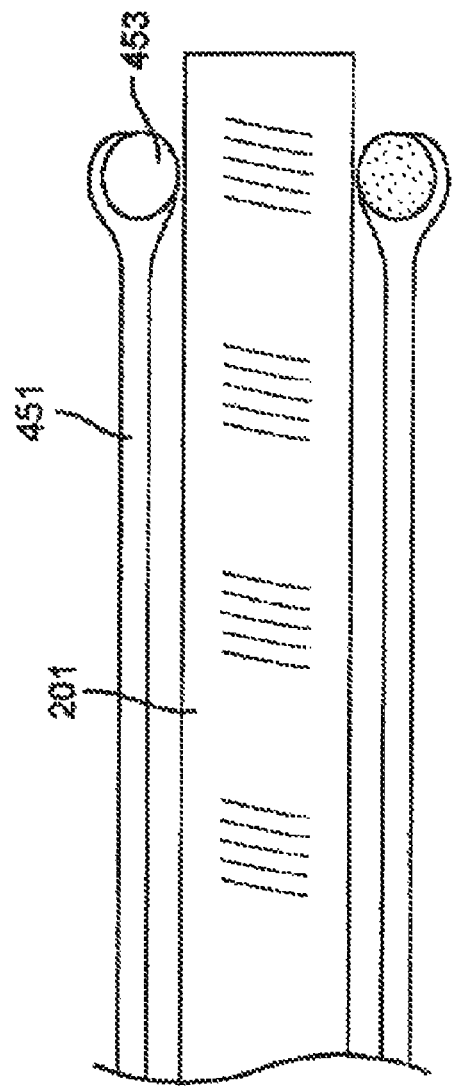
FIG. 74A
FIG. 74B

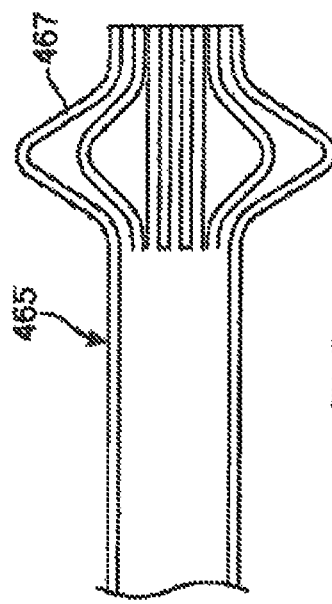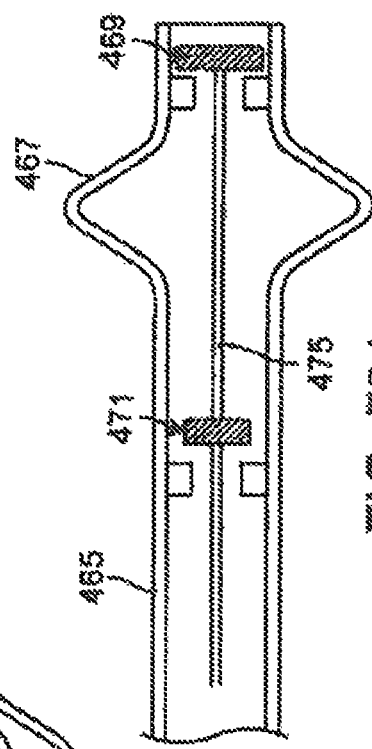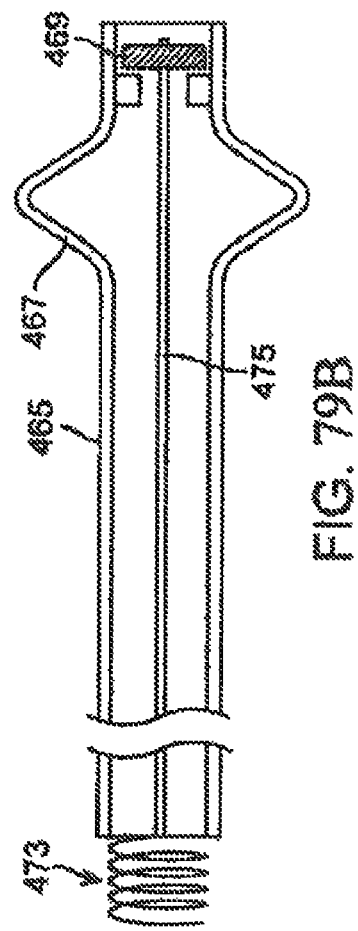

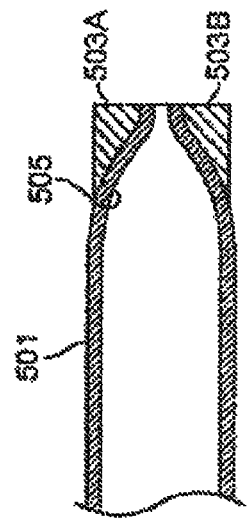
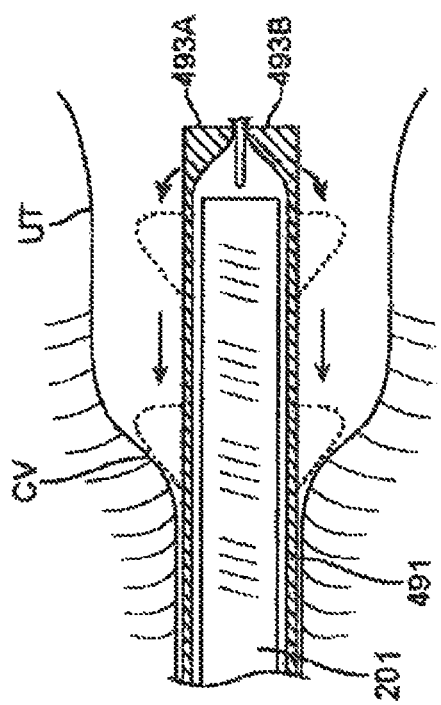
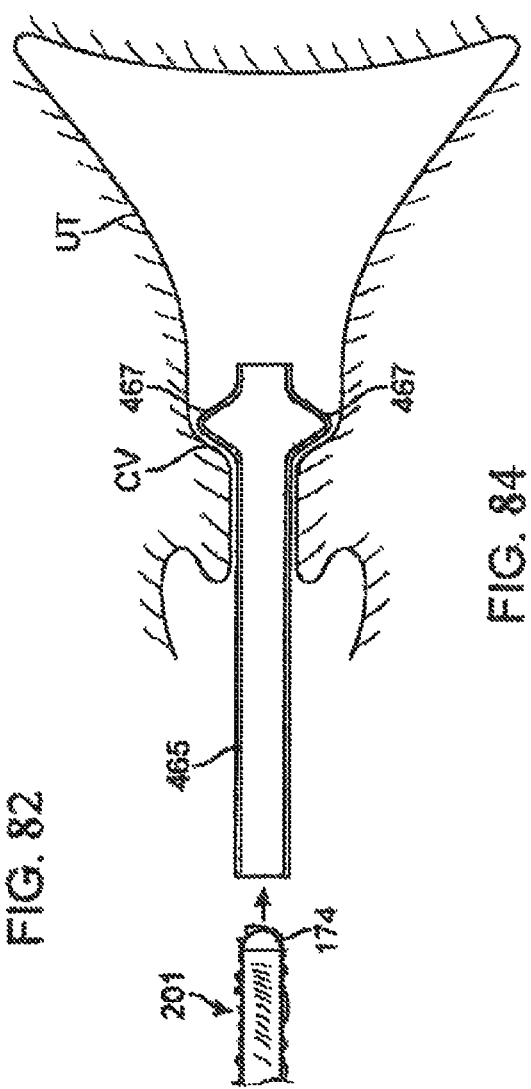

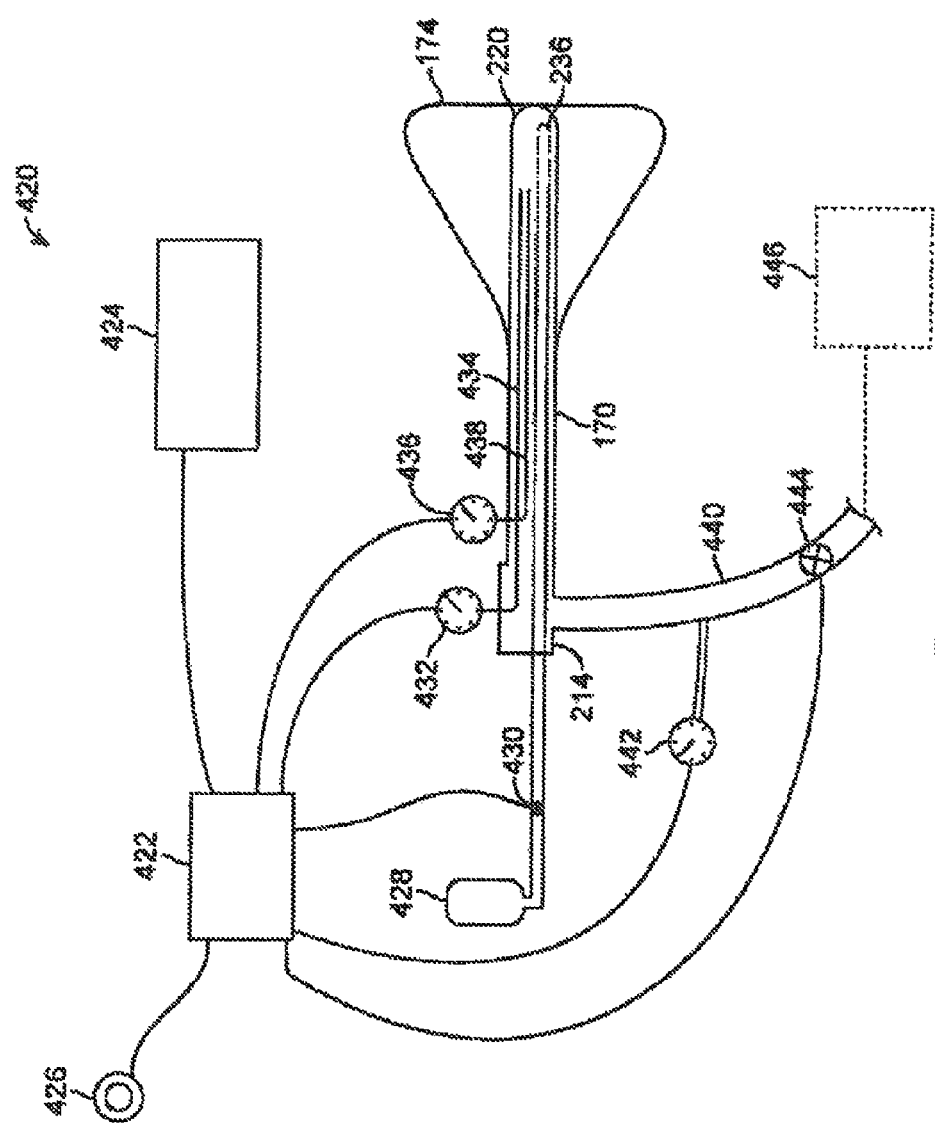

CYROGENIC TREATMENT SYSTEMS

CROSS-REFERENCE TO RELATED APPLICATIONS

This application is a continuation of U.S. patent application Ser. No. 13/900,916 filed May 23, 2013, which is a continuation-in-part of U.S. patent application Ser. No. 13/361,779 filed Jan. 30, 2012, which claims the benefit of priority to U.S. Provisional Application No. 61/462,328 filed Feb. 1, 2011 and U.S. Provisional Application No. 61/571,123 filed Jun. 22, 2011, each of which is incorporated herein by reference in its entirety.

FIELD OF THE INVENTION

The present invention relates to medical devices. In particular, the present invention relates to methods and apparatus for therapeutic devices capable of exposing areas of the body to elevated or decreased temperatures, in a highly controlled manner.

BACKGROUND OF THE INVENTION

In the last few decades, therapeutic intervention within a body cavity or lumen has developed rapidly with respect to delivery of energy via radiofrequency ablation. While successful in several arenas, radiofrequency ablation has several major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

The current state of the art would benefit from minimally invasive devices and methods which deliver thermal energy to a desired area or extract energy from a desired area, in a consistent, controlled manner that does not char or inadvertently freeze certain tissues or create excessive risk of unwanted organ or lumen damage.

SUMMARY OF THE INVENTION

When bodily tissues are exposed to even slightly elevated temperatures (e.g., 42 degrees C. or greater), focal damage may occur. If the tissues are exposed to temperatures greater than, e.g., 50 degrees C., for an extended period of time, tissue death will occur. The energy delivered by RF can then be excessive while a more controlled treatment can be achieved with heated fluids and/or vapors.

Generally, devices for delivering controlled treatment may comprise a source for a heated liquid and/or gas, e.g., hot water/steam, one or more pumps to deliver said hot water/steam, a catheter having one or more lumens defined therethrough and also having one or more ports to deliver or circulate the heated liquid and/or gas, e.g., hot water and/or vapor, to a controlled site in a controlled manner. The catheter may also have optional pressure and temperature sensing elements. The optional pressure and temperature sensing elements may allow the operator to monitor and/or control the pressure and temperature within the treatment zone and also prevent the pressure from becoming too high. The treatment site may be delineated by inflatable or expandable members which are pressurized or expanded to a target pressure to form a seal with the body cavity/lumen. The heated liquid and/or gas may then be delivered to the area contained by the inflatable/expandable members at a pressure that is less than that of the inflatable/expandable members thereby effectively containing the treatment area between these inflatable/expandable members. Optionally, a chilled, room temperature, or warmed fluid such as water may then be used to rapidly terminate the treatment session.

The catheter having the inflatable/expandable members and optional pressure or temperature-sensing elements may be fitted within the lumen of an endoscope or other visualization device allowing the therapy to be delivered under direct visualization. In addition to direct visualization, this advance allows the scope to function as an insulator for the treatment catheter, thereby preventing unwanted exposure of body cavities/lumens to the elevated temperatures found in the heated liquid and/or gas coursing within the treatment catheter.

Generally, the heated liquid and/or gas may be heated to a temperature of between, e.g., 50 and 100 degrees Celsius. Exposure to these less elevated temperatures may allow for more controlled tissue damage and may obviate issues typically associated with the higher energy forms of treatment. It is understood and known in the art that the lower the temperature, the longer the dwell/treatment time needed. One treatment modality may be to deliver the heated liquid and/or gas at a temperature of, e.g., about 70 degrees C. for 5 minutes. Another modality may be to treat the tissue with the heated liquid and/or gas at a temperature of, e.g., 90 degree C. for 30 secs.

Among other features, the system may also include 1) the ability to thoroughly treat the treatment area due to the use of confining balloon(s) and/or use of an umbrella-like seal and use of a pressurized heated liquid and/or gas as the energy delivery medium, 2) the ability to treat relatively large areas in a very controlled manner due to the adjustable relationship between the two treatment-area defining inflatable/expandable components (e.g. balloon(s) and/or an umbrella-like seal), 3) the ability to form a liquid and/or gas-tight seal between the balloon(s) (and/or an umbrella-like seal) due to the catheter for the distal balloon traveling within the lumen of the proximal balloon catheter (avoidance of leakage around the catheters that the balloons can seal about), 4) the optional ability to monitor and control the pressure within the treatment area to ensure that the treatment area is not exposed to excessive pressures and that the pressure in the treatment area is prohibited from exceeding a pressure of the treatment area defining balloons, 5) the ability to ablate to a controlled depth in a reliable manner due to the lower energy and longer exposure times which allow the submucosa to cool itself with incoming blood flow, 6) the optional ability to fit within a working channel of an endoscope so that the device need not be inserted in a blind manner, 7) the ability to combine thermal or cooling therapy with delivery of active agents (e.g., anesthetic for pre-treatment of the target area or a chemotherapeutic for the treatment cancer or precancerous lesions, etc.), 8) the ability to fill the treatment defining area with fluid (e.g. cool, warm or room temperature fluid) capable of neutralizing the thermal or cooling energy in the treatment area in order to prevent potential damage caused by balloon rupture or seepage around the balloon and/or expandable member, 9) the ability to pre-chill (or pre-warm) the treatment area so that the submucosal tissues can be protected against the elevated (or cooling) temperature to which the lumen or bodily organ is being exposed, 10) the ability to adjust the treatment temperature time and/or temperature, 11) the ability to have modular, automated or semi-automated components and controls for handling the cooling, heating, inflations, deflations, infusions and/or extractions, 12) the ability to treat through the working channel of an endoscope or alongside an endoscope, 13) the ability to treat through a variety of endoscopes, e.g. nasal, gastrointestinal, esophageal, etc., 14) the ability to use off-the-shelf and/or disposable components to handle the fluid and pressure controls, or to use an automated or semi-automated system.

Additionally, the system may also incorporate features that may allow for efficacious therapy. For example, the system may utilize a sub-zero degrees Celsius temperature fluid lavage. This cold lavage may allow for much better control than charring and heating of the tissue and instead may provide a consistent depth of ablation in a manner that allows for rapid recovery and minimal post-operative pain (as opposed to heating methods). In addition, by using lavage of a liquid rather than cryogenic sprays (e.g., sprays which rely on the judgment of the user for determining time of spray application or spray location, etc.), the potential for over-ablation may be avoided. Also, the relatively colder cryogenic sprays have been found, in many cases, to result in damage to the endoscope while the higher temperatures possible with the system described herein (e.g., anywhere from −5 degrees Celsius to −90 degrees Celsius) is much less likely to damage the delivery equipment.

Secondly, the apparatus may utilize an umbrella-like element in the gastric space to allow for ablation of tissue regions, such as the lower esophageal sphincter at the gastroesophageal junction. This ablation is generally difficult to perform using balloon-based ablation technologies due to the expansion of the sphincter into the stomach. By utilizing an expandable, umbrella-like structure to form a firm seal at this site while allowing the ablation liquid and/or gas (heated or chilled) to contact the entire gastroesophageal junction. In addition, a spring-loaded element or other external force mechanism may be incorporated to provide for steady pressure and a firm seal against the stomach lining.

The apparatus may also be utilized with or without a balloon in body lumens or cavities that can be otherwise sealed. For example, a hypothermic fluid lavage of the uterus may be accomplished by introducing a subzero (Celsius) fluid into the uterus via cannulation of the uterus with a tube or cannula. If the tube is of sufficient diameter, backflow of the hypothermic lavage into the cervix and vagina may be prevented without the need for a balloon to contain the fluid. Use of balloons may be avoided for this particular type of application. In utilizing a hypothermic lavage, a fluid may be used that remains fluid even at subzero temperatures. This fluid may then circulated in the lumen (with or without a balloon) in order achieve ablation.

In using a hypothermic liquid rather than a gas, a greater thermal load can be repeatedly extracted from the tissue under controlled physiologic conditions using a liquid beyond the thermal load which may be extracted using a compressed gas. A liquid lavage, on the other hand, may be controlled based on temperature and pressure to provide a repeatable effect on the target organ. Compressed gas or other rapid cooling mechanisms, though, may be utilized in combination with this therapy in order to chill a solution to subzero temperatures after introduction into the body. In this variation, the biocompatible liquid capable of retaining liquid characteristics in a subzero state, or "anti-freeze solution", may be infused into the lumen or cavity after which the cooling probe may be introduced. Heat may be drawn from the anti-freeze solution until the desired hypothermic ablation temperature has been achieved for the desired duration of time. Fluid may or may not be circulated during this process via a pump or agitating element within the catheter in order to improve distribution of the ablative fluid.

In yet another variation, the treatment fluid may function to expand the uterus for consistent ablation, function to distribute the cryoablative freezing more evenly throughout the uterus, and potentially function to slow or prevent ice formation at the surface of the lumen or body cavity. The apparatus may be used with, for example, lipophilic, hydrophilic or amphipathic solutions with the latter two being having the ability to remove any aqueous fluid from the surface of the target cavity or lumen which may interfere with conduction of the heat from the target tissues into the cryoablative fluid.

Additionally and/or alternatively, the apparatus and methods described herein may be used as an adjunct to other treatments, such as the Her Option® therapy (American Medical Systems, Minnetonka, Minn.), by utilizing a lavage of the target cavity or lumen such as the uterus with the aqueous anti-freeze solution either prior to or during treatment in order to provide superior transmission of cryoablation with other existing cryoprobes without creation of the insulating ice layer at the surface. Moreover, lavage of the target lumen or cavity with a biocompatible antifreeze solution may be performed to improve transmission of the cryoablative effect as an adjunct to any cryotherapy treatment anywhere in the body where applicable. As described herein, the cryoablative fluid may also be introduced and/or lavaged within the target lumen or body cavity within a balloon which may be expanded to contact the walls of the lumen or body cavity. The cryoablative treatment fluid may be actively lavaged in and out of the balloon and/or deeply chilled by a cryoprobe within the balloon after introduction into the body cavity or lumen. Moreover, the anti-freeze solution may also comprise various salts and/or other biocompatible molecules capable of driving the freezing temperature of the solution below, e.g., −10 degrees Celsius. Additionally, the fluid may be capable of resisting freezing even at a temperature of, e.g., −90 degrees Celsius. A combination of salts, alcohols, glycols and/or other molecules may be used to provide this resistance to freezing in an aqueous solution.

In yet another variation, a cryoprobe with, e.g., a protective cage and/or a recirculator/fluid agitator, may be utilized to ensure that the hypothermic fluid is evenly distributed. The cage may be configured into various forms so long as it exposes the fluid to the surface of the cryoprobe while preventing direct contact of the cryoprobe with the wall of the lumen or cavity to be ablated (such as a uterus). A recirculator may comprise, e.g., a stirring element at the tip of the cryoprobe, an intermittent or continuous flow system or other fluid movement mechanism.

In another variation, to facilitate the balloon expanding and conforming readily against the tissue walls of the uterus, the balloon may be inflated with a gas or liquid. Alternatively, the balloon may be filled partially or completely with a conductive material. Once the elongate shaft has been introduced through the cervix and into the uterus, the distal opening of the shaft may be positioned distal to the internal os and balloon may be deployed either from within the shaft or from an external sheath. The balloon may be deployed and allowed to unfurl or unwrap within the uterus. The cooling probe may be introduced through the shaft and into the balloon interior (or introduced after insertion of the conductive elements).

The conductive elements may be introduced into the balloon interior through an annular opening within the distal end of the shaft until the balloon is at least partially or completely filled with the elements. The conductive elements may generally comprise any number of thermally conductive elements such as copper spheres or some other inert metal such as gold. These conductive elements may be atraumatic in shape and are small enough to fill the balloon interior and conform the balloon walls against the uterine walls to ensure consistent contact with the tissue, e.g., about 20 ml in volume of the elements. The conductive elements may also help to fill any air pockets which may form particularly near the tapered portions of the balloon and insulate the tissue from the ablative effects of the cryoablative fluid. For instance, the conductive elements may be formed into spheres having a diameter of, e.g., 0.8 mm to 4 mm or larger. To ensure that that conductive elements are fully and evenly dispersed throughout the balloon interior, the elements may be introduced through the shaft via an ejector or push rod, auger, compressed air, etc. In particular, the conductive elements may fill the tapered portions of the balloon to ensure that the balloon is positioned proximate to and in contact with the uterine cornu to fully treat the interior of the uterus.

With the conductive elements placed within the balloon, the cryoablative fluid may be introduced within and through the balloon such that the conductive elements facilitate the thermal transfer from the contacted uterine walls. Once the cryoablative treatment has been completed, the conductive elements may be removed through the shaft via a vacuum force or other mechanical or electromechanical mechanisms and the balloon, once emptied, may also be withdrawn from the uterus.

The cooling probe introduced into the interior of the balloon may comprise a number of different configurations which facilitate the introduction of the cryoablative fluid into the balloon. One such variation, the shaft may have one or more cooling members which project from the distal end of the shaft at various angles. Another variation of the cooling probe may have a rotating base and spray member positioned upon the shaft. The spray member may have a surface which is meshed, latticed, perforated, etc. such that the cryoablative fluid introduced through the shaft may enter the rotating base and spray member where it may be evenly dispersed through the spray member and into the interior of the balloon for treatment.

The cooling probe positioned within the balloon may be variously configured and may include further variations. The cooling probe assembly may comprise an exhaust catheter having an atraumatic tip and an imaging instrument such as a hysteroscope positioned within. One or more supporting members or inserts may be positioned throughout the length of the lumen to provide structural support to the catheter and to prevent its collapse and a probe support (e.g., flat wire, ribbon, etc.) may extend through the catheter interior.

The probe support may be supported within the lumen via the inserts such that the probe support separates the lumen into a first channel and a second channel where the cooling lumens may be positioned along the probe support within the second channel while the first channel may remain clear for the optional insertion of a hysteroscope. Because of the thickness of the probe support relative to its width, the probe support may be flexed or curved in a single plane while remaining relatively stiff in the plane transverse to the plane.

The probe may further include one or more cooling lumens which are positioned along the probe support within the second channel. Because the cooling lumens are located along the second channel, as separated by the probe support, one or more windows or openings may be defined along the length of the probe support to allow for the passage of any cryoablative fluid to proliferate through the entire lumen defined by the catheter. The number of cooling lumens may also be varied to number more than three lumens terminating at different positions along the active portion.

As the cryoablative fluid is introduced into and distributed throughout the catheter lumen, the exhaust catheter may also define one or more openings to allow for the cryoablative fluid to vent or exhaust from the catheter interior and into the interior of the balloon.

One example for a treatment cycle using a two cycle process may include the introduction of the cryoablative fluid for a treatment time of two minutes where the surrounding tissue is frozen. The fluid may be withdrawn from the balloon and the tissue may be allowed to thaw over a period of five minutes. The cryoablative fluid may be then reintroduced and the tissue frozen again for a period of two minutes and the fluid may then be withdrawn again to allow the tissue to thaw for a period of five minutes. The tissue may be visually inspected, e.g., via the hysteroscope, to check for ablation coverage. If the tissue has been sufficiently ablated, the assembly may be removed from the uterus, otherwise, the treatment cycle may be repeated as needed. In other alternatives, a single cycle may be utilized or more than two cycles may be utilized, as needed, to treat the tissue sufficiently. Furthermore, during the treatment cycle, a minimum pressure of, e.g., 40 to 80 mm Hg, may be optionally maintained by the cryogenic liquid or by a gas (e.g., air, carbon dioxide, etc.) to keep the balloon and uterus open.

The balloon may be expanded within the uterus and particularly into the uterine cornu by an initial burst of gas or liquid. Other mechanisms may also be used to facilitate the balloon expansion. One variation may utilize one or more supporting arms extending from a support which may be deployed within the balloon. The supporting arms may be variously configured although they are shown in this example in a Y-configuration. Yet another variation may include the supporting arms incorporated into elongate channels or pockets defined along the balloon itself.

Aside from the balloon itself and the use of balloons for obstructing the os, internal os, and/or external os, balloons or inflatable liners may also be used to insulate the cryogenic fluid during delivery into the balloon to protect the surrounding tissue structures which are not to be ablated, such as the cervix.

In controlling the ablative treatments described above, the treatment assembly may be integrated into a single cooling system contained entirely within the handle assembly or it may be separated into components, as needed or desired. In either case, the cooling system may generally comprise a microcontroller for monitoring and/or controlling parameters such as cavity temperature, cavity pressure, exhaust pressure, etc.

A coolant reservoir, e.g., nitrous oxide canister, may be fluidly coupled to the handle and/or elongate shaft via a coolant valve which may be optionally controlled by the microcontroller. The coolant reservoir may be in fluid communication with the cooling probe assembly and with the interior of the balloon. Additionally, an exhaust lumen in communication with the elongate probe and having a back pressure valve may also include a pressure sensor where one or both of the back pressure sensor and/or valve may also be in communication with the microcontroller.

Another example of an exemplary tissue treatment system includes a handle having a housing; an elongate probe extending from the housing and having a distal tip and a flexible length; a liner expandably enclosing the probe; at least one infusion lumen positioned through or along the elongate probe, wherein the infusion lumen defines one or more openings along its length; and a controller configured to deliver a non-ablative fluid into the interior of liner to expand the liner; monitor a condition of the liner; deliver an ablative fluid into an interior of the liner via the infusion lumen; evacuate the ablative fluid from the liner.

An example of a method of treating tissue, comprises positioning an elongate probe into a body lumen to be treated; expanding a liner enclosing the probe into contact against the body lumen using a non-ablative fluid; monitoring a fluid condition of the liner; and infusing an ablative fluid through a delivery lumen such that the fluid passes into an infusion lumen and into the liner to contact an interior of the liner.

In another variation, a method of ablating tissue under the present disclosure can include positioning an elongate probe into a body lumen to be treated; delivering a non-ablative gas into the a liner enclosing the probe to expand the liner into contact against a tissue surface of the body lumen; monitoring a condition of the liner; infusing an ablative fluid in a liquid state through an infusion lumen along the probe and through one or more openings defined along a length of the infusion lumen; spraying the ablative fluid against a wall of the liner such that the ablative fluid transforms a state upon ablating tissue to a gas state upon cooling tissue in contact with the wall of the liner; and evacuating the ablative fluid in the gas state from the liner.

BRIEF DESCRIPTION OF THE DRAWINGS

For the purposes of the drawings and preferred embodiments, applications to the esophagus and uterus will be shown. However, the apparatus and methods may be applied to any body cavity/lumen which may be visualized with an endoscope or other visualization mechanism.

FIGS. 13A and 13B show another example of a single balloon device for ablation treatment within the uterus and/or endometrial lining.

FIG. 15 shows another example of an external cervical os occluding device.

FIG. 16 shows another example of an internal cervical os occluding device.

FIG. 21A shows a side view of an integrated treatment assembly.

FIG. 21B shows an example of the assembly advanced through the cervix and into the uterus where the sheath may be retracted via the handle assembly to deploy the balloon.

FIGS. 23A and 23B show perspective and side views, respectively, of another example of a cooling probe assembly having a flat wire integrated through the probe.

FIGS. 25A and 25B show end views of a cross-section of the cooling probe and the distal end of the probe.

FIGS. 26A to 26L show perspective views of various tubular members which may be used for the cooling probe assembly.

FIG. 34 shows a side view of another variation of a spring body having one or more cooling lumens attached directly to the spring.

FIG. 35 shows a side view of another variation of a spring body having the one or more insert members.

FIG. 36 shows a side view of another variation of a spring body having the one or more cooling lumens and a secondary lumen.

FIGS. 38A and 38B show perspective views of another variation of the cooling probe utilizing a main delivery line and at least two side delivery lines.

FIG. 38C shows a detail view of the side delivery line having an adjustable mandrel slidably positioned within.

FIG. 63 shows a side view of another example where expandable foam may be deployed via the outer sheath.

FIG. 64 shows a side view of another example where a heating element may be located along the inner or outer surface of the elongate shaft.

FIGS. 74A and 74B show cross-sectional side views of another variation of an outer sheath having a reconfigurable distal end.

FIG. 78 shows a side view of another variation of an outer sheath having a radially expandable portion.

FIGS. 79A and 79B show cross-sectional side views of variations of the locking mechanism for the expandable portion.

FIG. 82 shows a cross-sectional side view of the one or more cam members deployed in their expanded configuration and secured against the cervical tissue.

FIG. 83 shows a cross-sectional side view of another variation where the cammed distal end positioned on a tapered outer sheath.

FIG. 84 shows a side view of an example of how the outer sheath may be initially deployed and secured and the cooling probe assembly advanced separately.

FIG. 89 shows an exemplary schematic illustration of the treatment assembly integrated into a single cooling system.

DETAILED DESCRIPTION OF THE INVENTION

Figure 1:
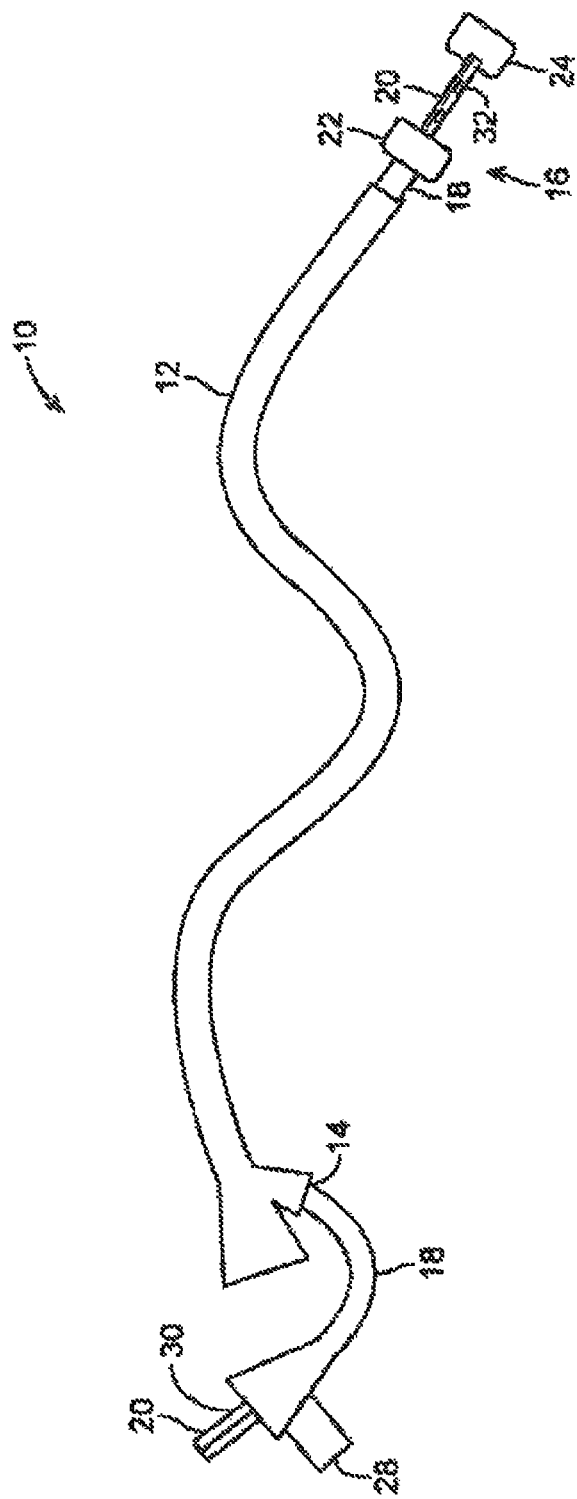
FIG. 1 shows an example of a device advanced through an endoscope, e.g., a nasally or orally inserted scope.

FIG. 1 shows a perspective view of one example of the treatment assembly 10 positioned within a working channel 14 of an endoscope 12 (e.g., orally or nasally insertable scope). In this example, the treatment device 16 itself may utilize a first catheter 18 having an inflatable or expandable balloon member 22 and a second catheter 20 that may slide freely with respect to the first catheter 18 and also having an inflatable balloon member 24 at its distal end. The first catheter 18 as well as second catheter 20 may have a liquid and/or gas tight seal 30 formed at the proximal end of the catheters. The inflatable and/or expandable members 22, 24 (shown in this example as inflated balloons) may be pressurized to effectively and safely occlude the lumen. The balloons may be filled with chilled or room temperature fluid to prevent possible damage caused by balloon rupture or seepage around the balloon. Pressure within the inflatable or expandable balloon members may also be monitored to ensure that a tight seal has been formed within the lumen or body cavity.

Additionally, the liquid may be introduced into the treatment area through a liquid and/or gas port 28 and into the lumen of the catheter which terminates with the proximal balloon 22 and leaves the catheter through perforations or holes 32 within the second catheter 20 which terminates in the distal balloon 24, although this flow path may easily be reversed if necessary. Alternatively, one or more ports can be designed into the lumen between the distal 24 and proximal 22 balloons, such that the heated or cooling fluid exits one or more ports 32 in the lumens near the distal balloon 24, and is then evacuated in a port or ports designed within the lumen of the first catheter 18 nearest the proximal balloon 22. In this variation, the endoscope 12 may insulate the catheters allowing the catheters to be much smaller than would be otherwise possible and allowing it to fit within the working channel 14 of a standard endoscope 12. One or more pressure sensors may be used to detect both inflation pressures of the balloons and/or the pressure seen by the body cavity/lumen that is exposed to the treatment liquid/vapor. In the manner, liquid/vapor flow may be controlled by the pressure sensing elements within the body cavity/lumen to ensure that safe pressures are never exceeded. Manual controls may be used for creation and/or maintenance of these pressures (e.g. syringes with stopcocks) or automated and/or semi-automated systems can be used as well (e.g. pumps with PID loops and pressure sensing interconnectivity. Although the liquid and/or gas for tissue treatment may be heated or chilled prior to introduction into the treatment area in contact with the tissue, the liquid and/or gas may alternatively be heated or chilled after introduction into the treatment area and already in contact with the tissue.

Figure 2:
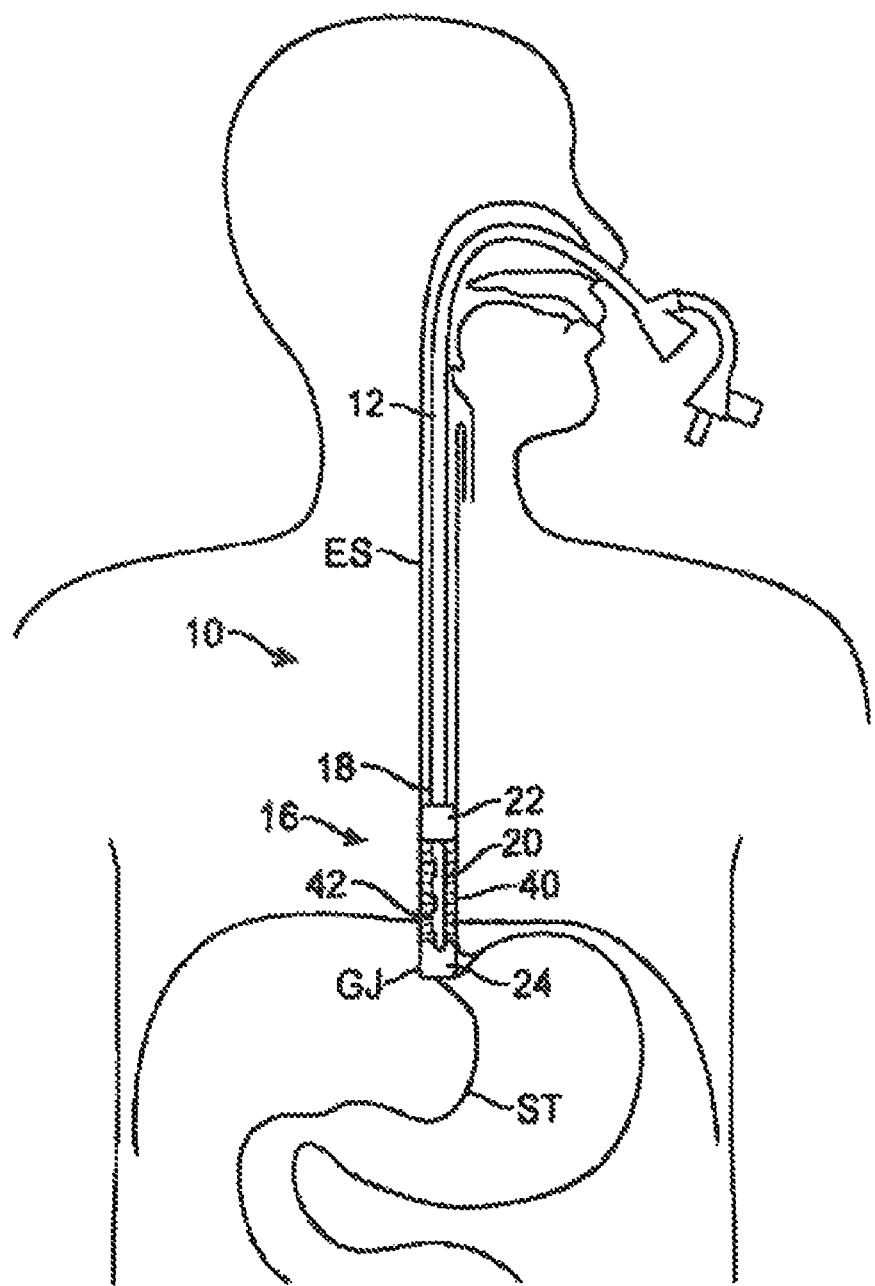
FIG. 2 shows an example of a device advanced through the working channel of nasal endoscope.

FIG. 2 shows an example where the second catheter 20 and distal balloon member 24 is slidable relative to the proximal balloon 22. This examples illustrates the endoscope inserted through the nasal cavity and advanced through the esophagus ES where the catheters 18, 20 may comprise single or multi-lumen catheters having inflation lumens for the distal 24 and proximal 22 inflatable/expandable elements, infusion port and extraction port. At least one of the catheters may be fitted with either a pressure transducer 42 or a lumen to carry the pressure signal from the treatment area back to the controller or dial gauge. Pressure sensing may be accomplished through a small, air capsule proximal to the distal balloon 24, but within the treatment area. Both of the balloons 22, 24 may be inflated along the esophagus ES in the proximity to the gastroesophageal junction GJ proximal to the stomach ST to create a treatment space 40 which encompasses the tissue region to be treated.

In an alternative embodiment, an extraction lumen may be omitted as a preset dose of heated liquid and/or gas may be delivered, allowed to dwell and then either extracted through the same lumen or rendered harmless with the infusion of cold fluid. This treatment algorithm would provide an even simpler therapy and would rely on the exclusion of a certain area and exposure of that area to a liquid or vapor with the desired energy. Infusion of the liquid or vapor may be controlled to ensure that the treatment area is not exposed to excessive temperatures.

Figure 3:
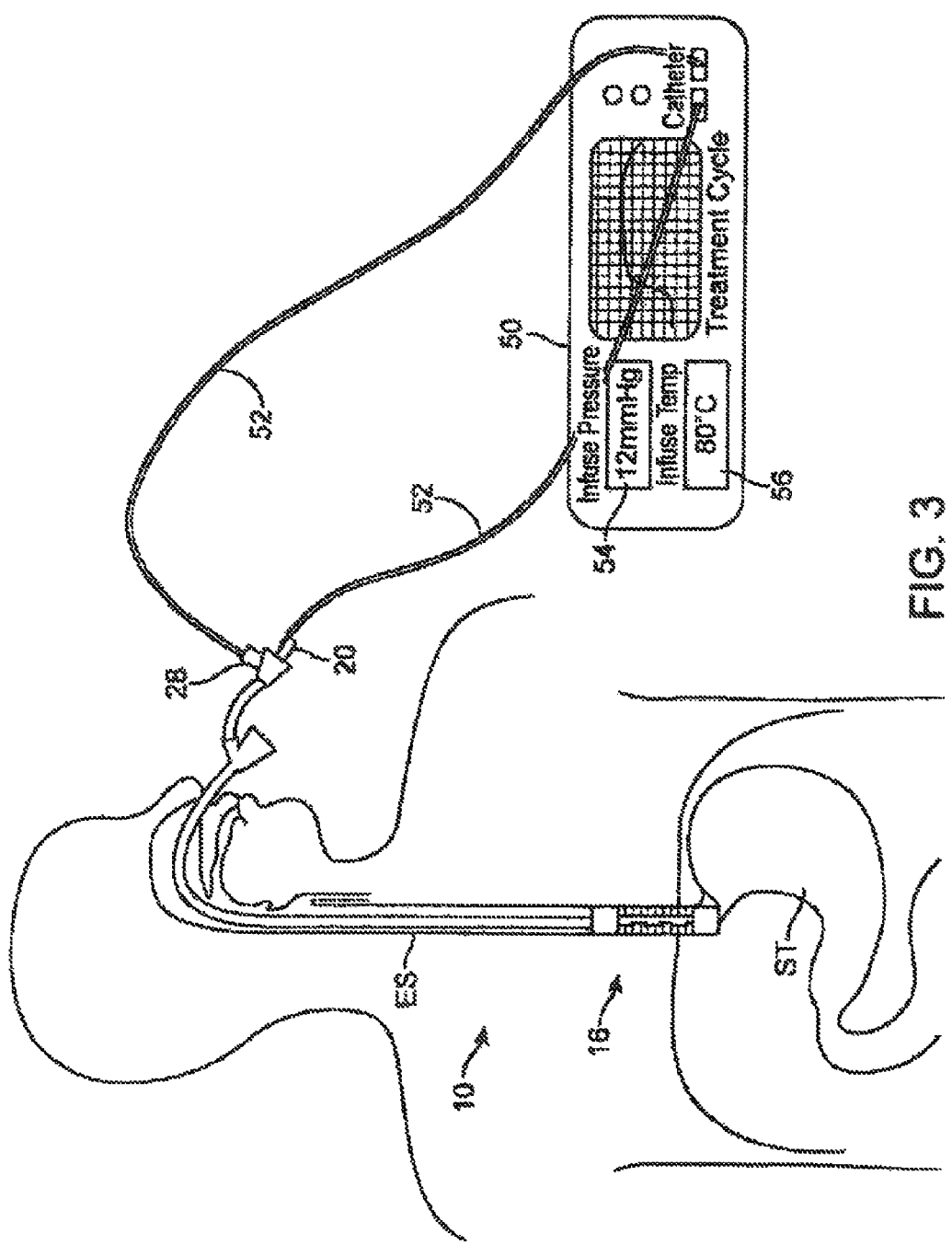
FIG. 3 shows an example of a device attached to a logic controller.

FIG. 3 shows another example where the treatment assembly 10 may be in communication with a controller 50, such as a logic controller. Controller 50 may control certain parameters such as infusion pressure 54 of the fluid as well as fluid temperature 56 and it may be coupled to the assembly by one or more cables 52. The pressure in the treatment area, the elapsed time, the temperature of the fluid, and the extraction rate may also be monitored and controlled.

Figure 4:
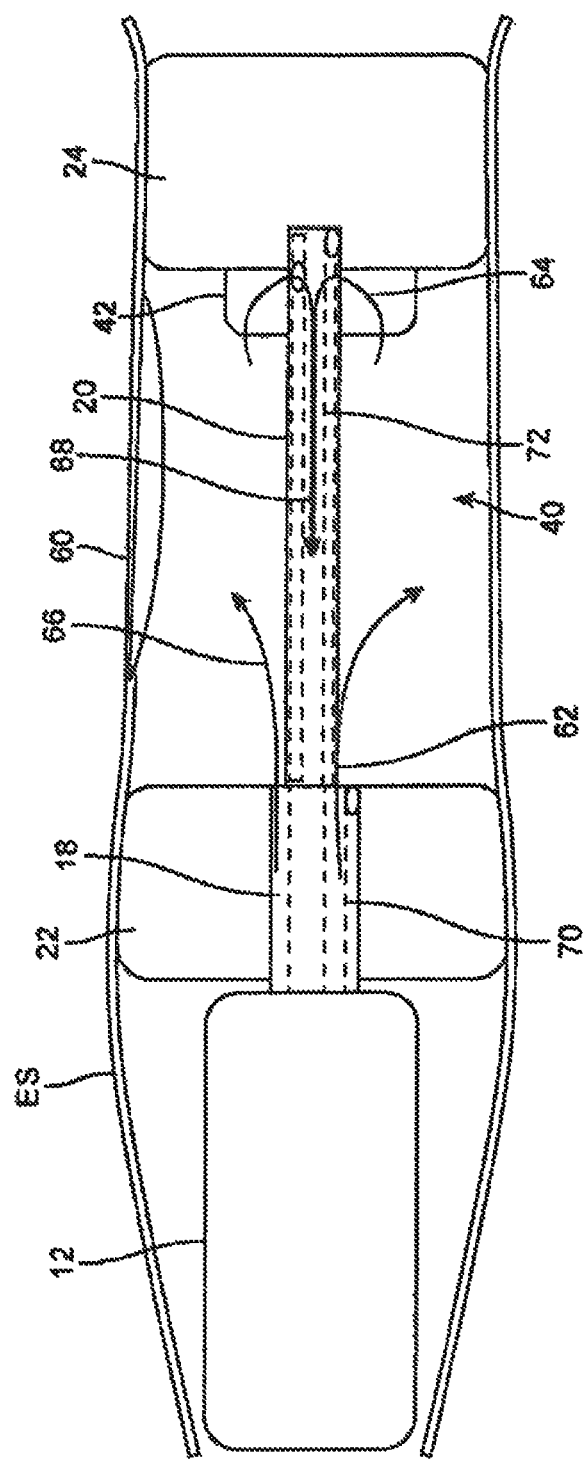
FIG. 4 shows an example of a device placed through working channel of nasal endoscope and deployed within an esophagus for treatment.

FIG. 4 shows a detail view of the treatment area 40 defined, in this case, by two balloons 22, 24. The first catheter 18 may open into the lumen just after the proximal balloon 22 and this catheter 18 may be inserted along with or prior to insertion of the second catheter 20. The first catheter 18 internal diameter is greater than the outer diameter of the second catheter allowing for liquid (and/or vapor) to be infused or extracted around the outer diameter of the second catheter 20. The second catheter 20 a first lumen for balloon inflation and a second lumen for evacuating the treatment region 40. With the balloons inflated into contact against the esophagus ES, the treatment area 40 may encompass the tissue region to be treated, e.g., a lesion 60 such as Barrett's esophagus or esophageal cancer lesion and the distal end of the endoscope 12 may be positioned into close proximity to proximal balloon 22 and the treating liquid and/or gas 66 may be infused through the annular lumen 70 defined through first catheter 18 and between second catheter 20 such that the fluid 66 may enter through opening 62 into the treatment region 40 while contained by the balloons. Once treatment has been completed, the fluid may be evacuated 68 through one or more openings 64 located along the second catheter 20 proximal to distal balloon 24 and proximally through the second catheter 20 through the evacuation lumen 72. As previously mentioned, a pressure sensor 42 (e.g., pressure measuring air capsule) may be positioned along either the first 18 and/or second 20 catheter for sensing the various parameters. Additionally, the treatment liquid and/or gas may include any number of liquids, vapors, or other chemically active (e.g., chemotherapeutic) or inactive compounds for additional treatments to the tissue.

In the event that the treatment is provided by a simple timed dwell, the extraction 72 and infusion 70 lumens may not both be utilized. The pressure sensing element 42 (solid-state, piezoelectric, or other method) may be located on either the first or second catheters and the second catheter and may comprise a simple slidable balloon. A pressure sensor for the treatment may be omitted so long as the pressure can be controlled by other mechanisms, e.g., a check valve or a simple gravity fluid column. An active pressure measurement, though, may ensure that safe pressures are not being exceeded.

The second catheter 20 may fit easily within the first catheter 18 and may be slid inside the first catheter 18 until its distal balloon 24 is distal to the first balloon 22. The distal balloon 24 may then be inflated just beyond the distal portion of the treatment area 40 and the endoscope 12 may be pulled back. The most proximal extent of the lesion 60 may then be identified and the proximal balloon 22 may be inflated proximal to this area. Once the treatment area 40 has been enclosed (which may be verified by infusing liquid 66 and/or vapor under visualization and observing the seal around the balloon, balloons and/or expandable member) the lumen or body cavity may then be filled with the treatment liquid and/or vapor to a safe pressure. The liquid and/or vapor may also contain active agents (e.g. chemotherapeutic and/or anesthetic agents) and comprise more than simply an inactive liquid and/or vapor. Options would be for the active agents to be delivered prior to, during and/or post treatment of the heating (or cooling) liquid and/or vapor.

As the treatment assembly 16 does not contain the treatment liquid or vapor within a balloon(s) or expandable member and allows it to freely flow over the treatment area, the therapy may be applied consistently leaving no areas left untreated (as is frequently seen with balloon infusion-based or RF therapies). Additionally, treatment may be accomplished with a heated liquid (rather than a high energy electrode or excessively hot vapor) or a more controlled treatment can be achieved through the use of a relatively cooler liquid with a longer treatment time. In addition, the esophagus ES is a fluid transport type organ (lumen) and may be more compatible to fluid based therapies than with RF-based therapies. It is also believed that the safety margin of such treatments may be better than with an RF-based therapy.

Figure 5:
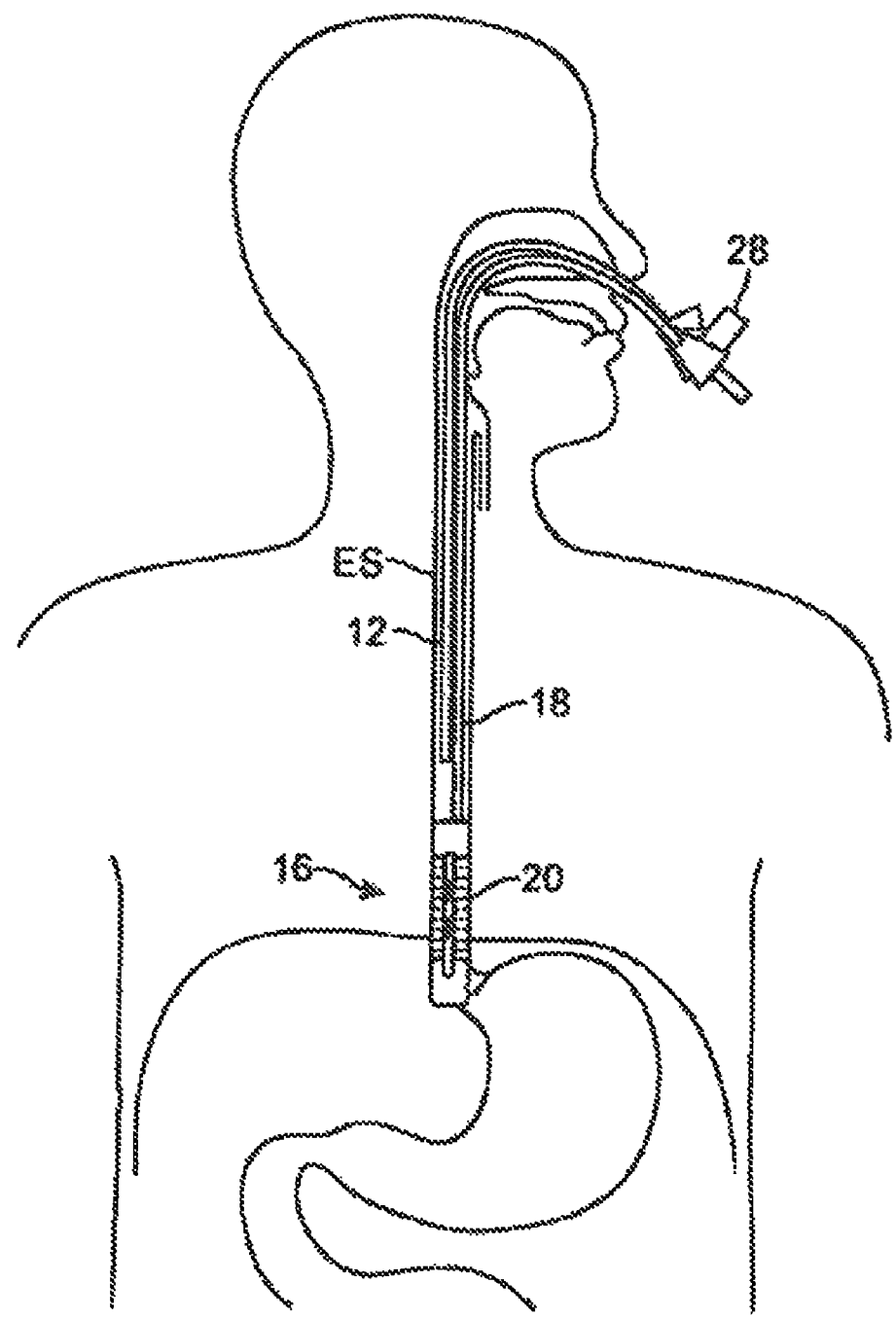
FIG. 5 shows an example of a device advanced alongside an endoscope.

FIG. 5 shows an alternative embodiment of the device in which the first catheter 18 and second catheter 20 of the treatment assembly 16 may be inserted alongside an endoscope 12 which may be used to provide for visualization. Due to the small size of the catheters, this embodiment is feasible.

Figure 6A:
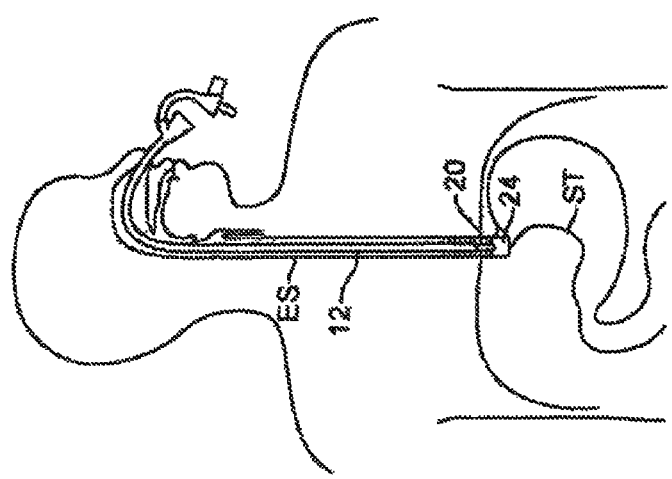
FIGS. 6A to 6C show a device being introduced through an endoscope and deployed for treatment within the esophagus.
Figure 6B:
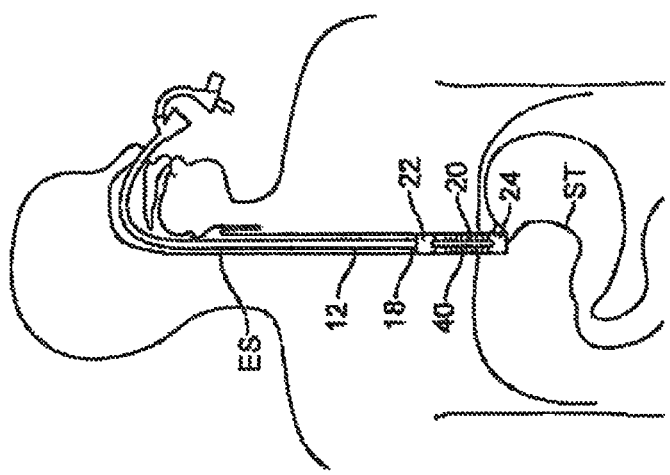
Figure 6C:
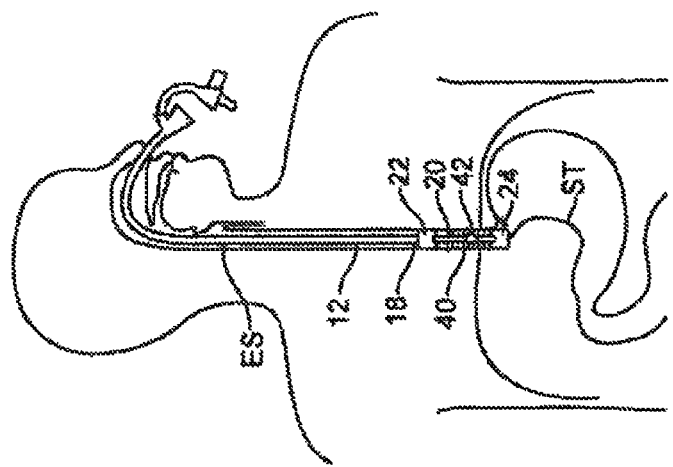

FIGS. 6A to 6C illustrate an example for a placement procedure for the assembly for the treatment of a body lumen such as the esophagus ES. The catheters may be inserted simultaneously or separately through the working channel of the endoscope 12. In one example, the larger first catheter 18 may be inserted first followed by insertion of the second catheter 20 within the lumen of the first catheter 18. Once both single or multi-lumen balloon catheters have been inserted and after the endoscope 12 has been advanced through the esophagus ES and into proximity to the tissue treatment region, the distal balloon 24 may be advanced to define the distal end of the treatment area and inflated (e.g., with chilled, room or body temperature fluid) while under visualization through the endoscope 12, as shown in FIG. 6A. The endoscope 12 may then be pulled back until the proximal end of the desired treatment area has been identified and the proximal balloon 22 may be slid over the shaft of the second catheter 20 and inflated (e.g., with chilled, room or body temperature fluid) at a site just proximal to the most proximal portion of the lesion, as shown in FIG. 6B.

With the treatment area 40 now enclosed by these balloons, an optional pressure capsule 42 (e.g., solid state, piezoeletric or other pressure sensing method) may be inflated and the treatment may proceed, as shown in FIG. 6C. The treatment session then exposes the lumen or body cavity to fluid pressurized to a positive pressure in the range of, e.g., 5-100 cmH2O (although this pressure may be maintained at a level below an inflation pressure of the inflation balloons) at temperatures between, e.g., 50 and 100 degrees Celsius, for a period of, e.g., 1 second to 10 minutes. Additionally and/or alternatively, the treatment area 40 may be lavaged for a period of time with an anesthetic (e.g., lidocaine or bupivicaine) to reduce pain with the procedure prior to the application of thermal energy or other active compounds. Accordingly, ablation may be accomplished at a consistent depth of, e.g., about 0.5 mm, throughout the esophagus ES.

Figure 7C:
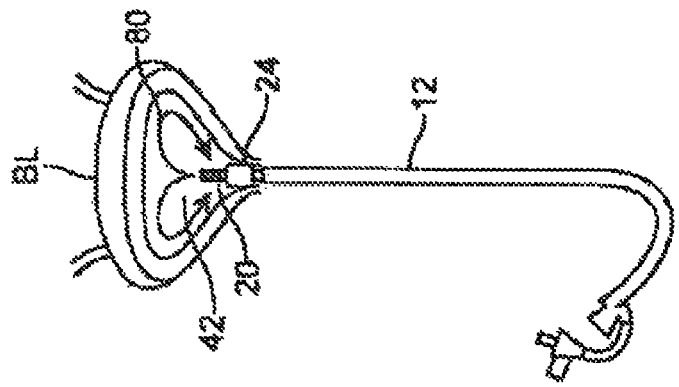
FIGS. 7A to 7C show examples of a device introduced through an endoscope for insertion within a bladder.
Figure 7B:
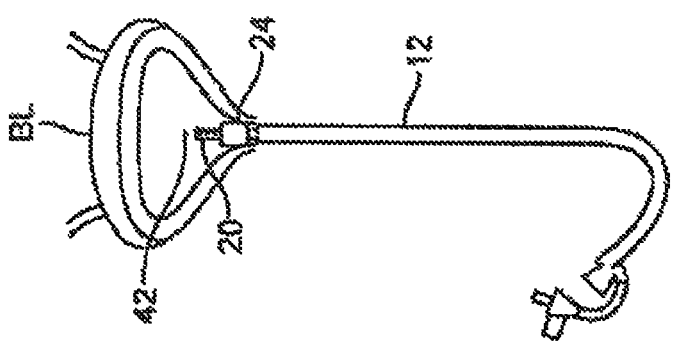
Figure 7A:
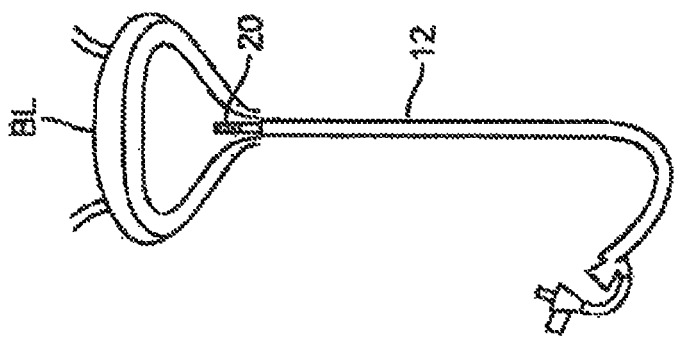

FIGS. 7A to 7C illustrate another example for treatment of an enclosed body cavity (shown here as a bladder BL). In this example, a single balloon may be used to effect infusion and extraction of the treatment fluid. Pressure may be monitored to ensure that the therapy is safe and a relatively lower temperature fluid may be used (e.g., 42-100 C) so that the entire cavity may see a controlled, uniform thermal load. The order or catheter placement may vary as may the sequence for balloon inflation or exposure to active or inactive liquid or vapors in this or any embodiment of the device. As shown in FIG. 7A, an endoscope (or cystoscope) 12 may be inserted into the target organ BL then fluid catheter 20 may be advanced into the lumen. With the endoscope 12 inserted and occlusion balloon inflated 24 (e.g., with unheated fluid) to seal the organ, a pressure sensor 42 may also be optionally inflated to measure pressure, as shown in FIG. 7B. Optionally, an anesthetic or pre-treatment medication may be delivered into the bladder BL, if so desired. Then, a high or low temperature fluid 80 may be circulated within the bladder BL under pressure adequate to safely distend the organ to ensure complete treatment, as shown in FIG. 7C.

Figure 8C:
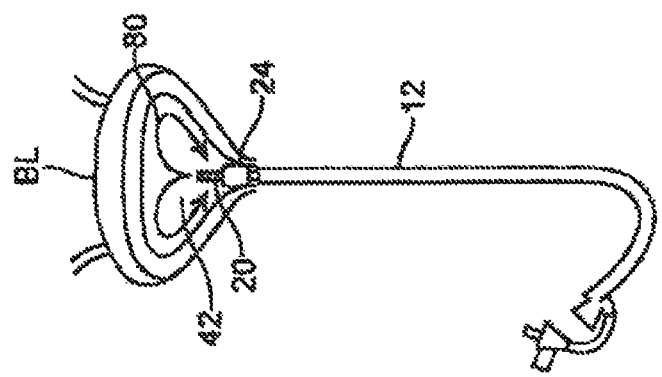
FIGS. 8A to 8C show examples of a device preparing the treatment area with a pre-treatment lavage prior to treatment.
Figure 8B:
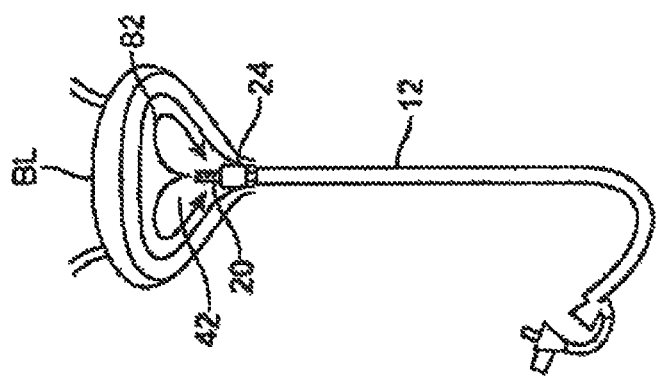
Figure 8A:
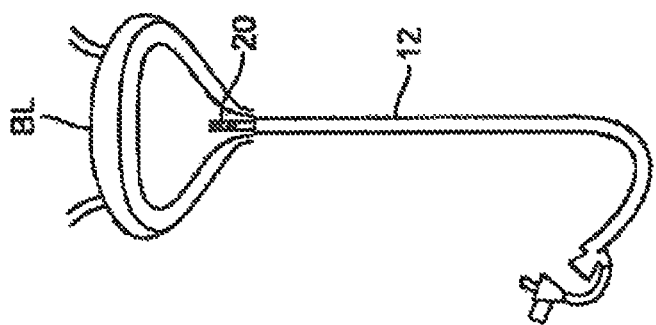

FIGS. 8A to 8C illustrate another example for treatment where the use a fluid lavage to prepare the treatment area (here shown as the bladder BL) may be accomplished prior to application of thermal (or cooling) energy and/or active compounds. As previously described, the endoscope 12 and catheter 20 may be introduced into the bladder BL and subsequently sealed with the occlusion balloon 24, as shown in FIGS. 8A and 8B. Preparation of the treatment area may involve use of an anesthetic to decrease pain during therapy or the use of an arterial constrictor to reduce blood flow to the organ or lumen. Alternatively, other pre-treatment fluids 82 may include, e.g., anesthetic, vascular constrictor, chilled fluid, active component antidote, etc. The pre-treatment fluid 82 may be evacuated (or left within the bladder BL) and the lavage with the treatment fluid 80 may be introduced into the bladder BL for treatment, as shown in FIG. 8C.

Alternatively, the pre-treatment fluid 82 may also be chilled (or heated) to cool (or warm) the lumen or organ prior to treatment so that the thermal (or cooling) energy may be applied to the internal surface of the lumen or body cavity with minimal transmission or conduction of the elevated (or cooling) temperatures to the submucosal tissues (or tissues lining the body organ or lumen). Utilizing the pre-treatment of the area may avoid damage to the underlying tissues to thereby avoid many of the complications of therapy. For example, strictures and/or stenosis (or tightening) of the tissue can be avoided by controlling the depth of penetration which may be controlled by pre-treating the area with a chilled fluid so that the submucosa can absorb significant amounts of heat without reaching damaging temperatures.

The depth of penetration may also be controlled through the use of a lower temperature fluid for thermal ablation so that the submucosa can cool itself with its robust vascular circulation (which is less robust in the mucosa and epithelium). In the event that an active compound is used, as well, an antidote to this compound may be delivered to the patient (either systemically or as a local pre-treatment) so that the underlying tissues and submucosa are not damaged. One example of this is the use of powerful antioxidants (systemically or locally) prior to lavage of the esophagus with, e.g., methotrexate. The methotrexate may have a powerful effect on the tissues to which it is directly exposed in the lumen or body cavity, but the anti-oxidants may prevent deeper penetration of the methotrexate. The neutralizing compound may also be placed within the balloon or in the lumen of surrounding lumens or body cavities to prevent exposure of these areas in the event of balloon rupture.

Figure 9:
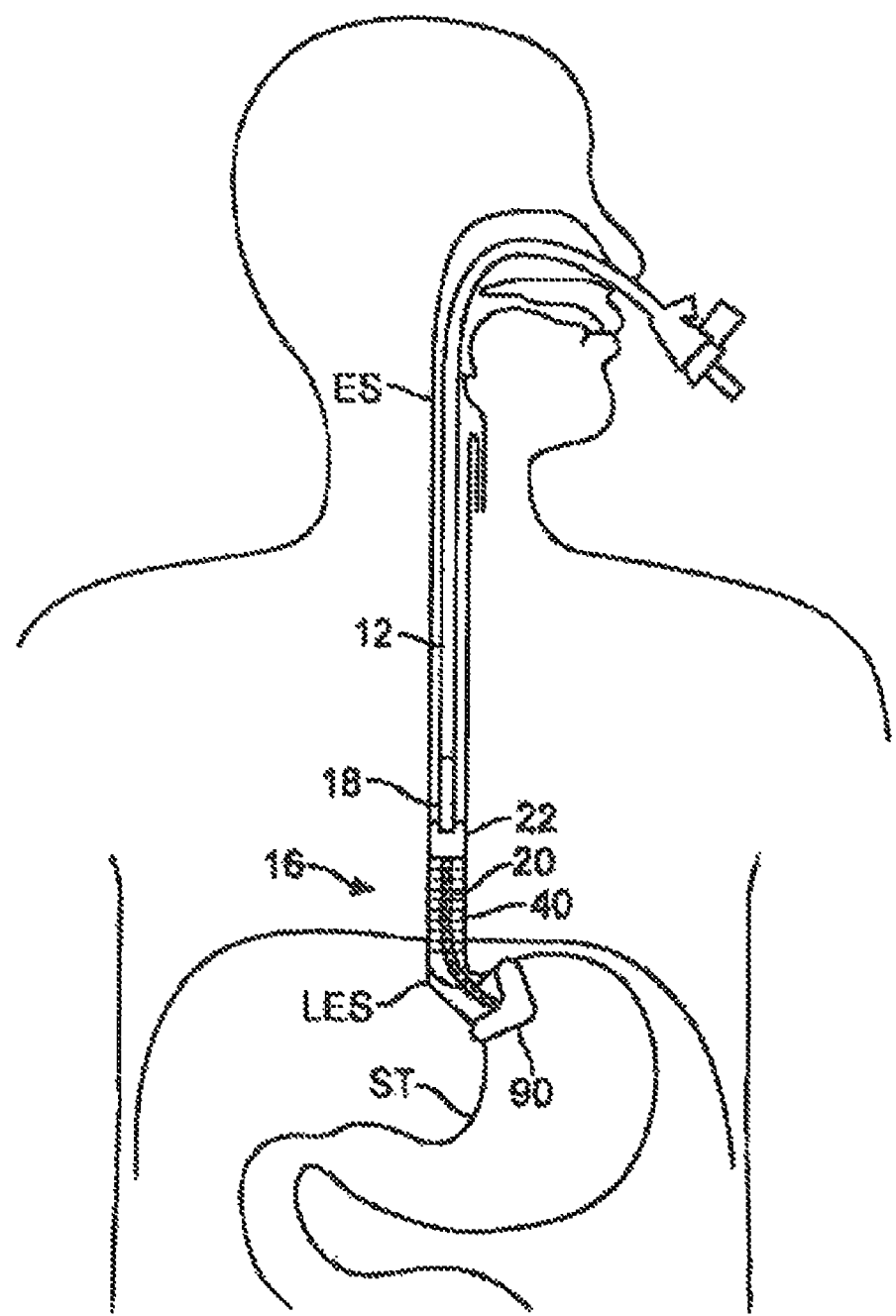
FIG. 9 shows an example of a distal occlude having an umbrella-like shape deployed in proximity to a gastroesophageal junction for treatment.

FIG. 9 shows another example where the distal occlusion member may be configured into an umbrella-like element 90 which may be expanded in the stomach ST and placed over a tissue region which is typically difficult to occlude by a balloon. For instance, such a shape may allow for ablation of the lower esophageal sphincter LES at the gastroesophageal junction (or other sphincter region if used elsewhere). The expandable, umbrella-like structure 90 may form a firm seal at this site while allowing the ablation fluid (hot or cold) to contact the entire gastroesophageal junction. Once expanded, the umbrella-like element 90 may be held firmly against the stomach ST by traction on the endoscope 12 or by a tensioning element on the catheter and balloon itself.

In addition, this element 90 may optionally incorporate a biased or spring-loaded element or other external force mechanism to provide steady pressure and a firm seal against the stomach lining. Alternative structures may also incorporate a more complex, nitinol cage (or other rigid material) connected by a thin, water-tight film. For example, nitinol may be used to decrease the overall profile of the obstruction element and increase its strength and durability.

Figure 10:
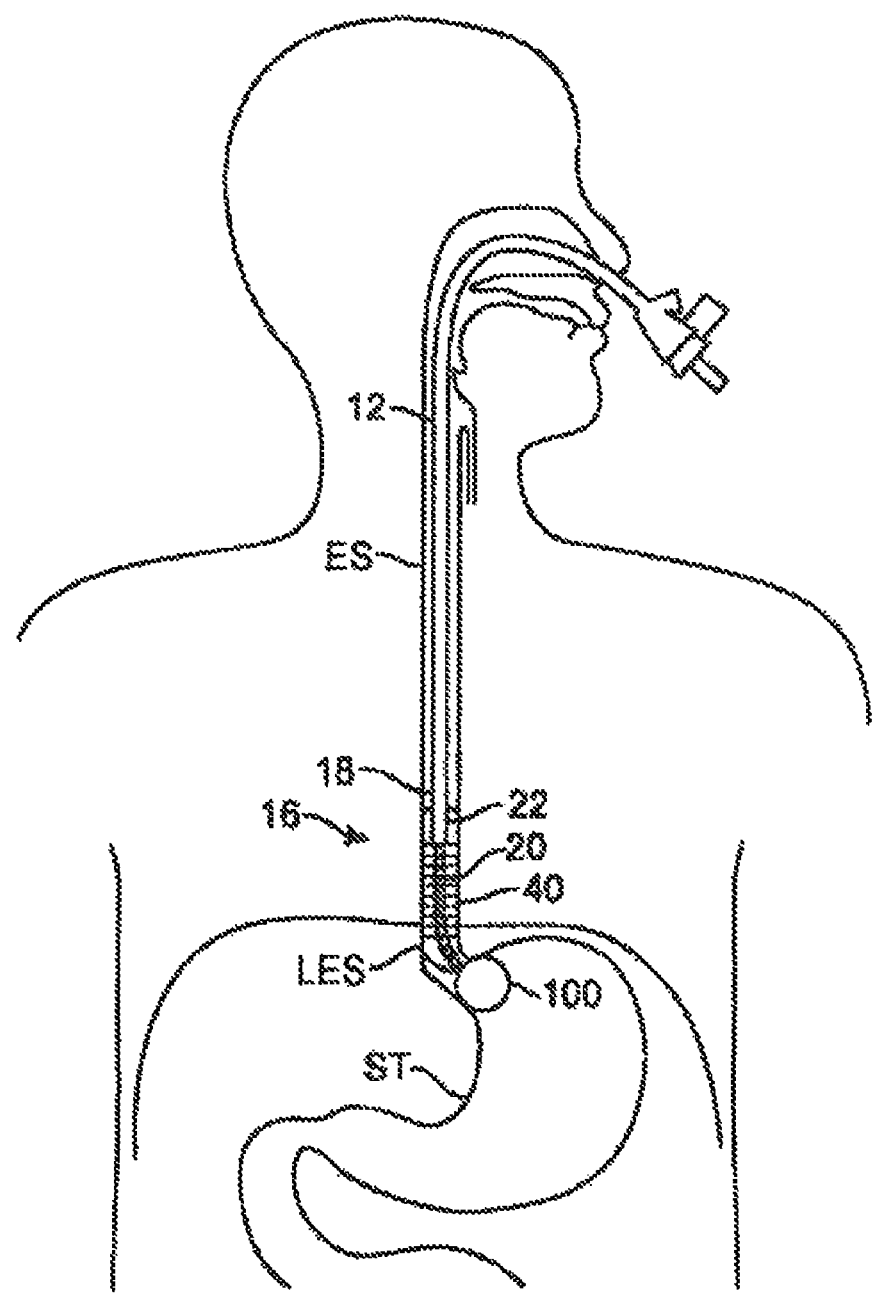
FIG. 10 shows another example of an endoscopic balloon sheath having a distal occluder expanded distal to gastroesophageal junction for treatment.

FIG. 10 shows another example which utilizes an endoscopic balloon sheath utilized as a distal occluder allowing for exposure and treatment of the distal gastroesophageal junction. In this embodiment, the second catheter 20 may have a distal occlusion balloon 100 which may be passed through the working channel of the endoscope 12 or through a channel incorporated into the balloon sheath itself (outside of the actual endoscope). Once expanded into an enlarged shape, the balloon 100 may be retracted to fit entirely over the lower esophageal junction LES to form the distal seal by traction on the endoscope 12 or by a tensioning element on the catheter and balloon itself. This gastric occlusion balloon may allow for exposure of the gastroesophageal junction while preventing fluid flow into the stomach ST. The balloon 22 may be configured to be saddle-shaped, circular, wedge-shaped, etc. It may also be self-expanding and non-inflatable.

Additionally, the proximal balloon 22 may be configured to be part of sheath that is placed over the tip of the endoscope 12 or it may be formed directly upon the endoscope tip itself. An inflation lumen may run inside the endoscope 12 or it may run alongside the endoscope 12 in a sheath or catheter. The balloon sheath may also incorporate a temperature sensor, pressure sensor, etc. Moreover, the proximal occlusion balloon 22 may optionally incorporate a temperature or pressure sensing element for the therapy and it may be positioned either through the working channel(s) of the endoscope 12 or alongside the endoscope 12 within the endoscopic balloon sheath.

In yet another embodiment, in order to reduce the risks associated with fluid flow and lavage, a fluid or gel may be infused into the esophagus between the balloons then heated or frozen in situ in order to provide the desired ablative effect without circulating any fluid or gel. In one example of this configuration, a gel may be infused into the esophagus and pressurized to a safe level (e.g., 30-100 mmHg) which may be then rapidly chilled using, for example, a compressed gas and/or a Peltier junction-type cooling element. The gel may freeze at a temperature below that of water and allow for rapid transmission of the ablative temperature to the tissues being treated. This gel may also be a liquid with a freezing point below that of water in which case the treatment zone may be lavaged with this fluid prior to treatment to remove free water and prevent crystal formation during therapy. Once the therapy has been completed, the gel or liquid may be removed or left in the esophagus to be passed into the stomach. In the event that a Peltier cooling or heating element is used, the polarity may be reversed once therapy is complete in order to reverse the temperature and terminate the ablation session.

The distance from the lower end of the distal most portion of the catheter can be on the order of about 150 mm. The distance between the proximal and distal balloons are adjustable by the operator but can be adjusted, e.g., from as small as 0 mm to as large as 25 cm. The treatment zone may have a range of, e.g., 3 to 15 cm.

In yet an additional embodiment, an energy generator (e.g., a RF electrode or hot wire or other energy source) may be advanced into the treatment area in a protective sheath (to prevent direct contact with body tissues) and energy may be applied to the treatment fluid to heat it to the desired temperature. Once the fluid is adequately heated and enough time has passed to achieve a controlled ablation, the fluid may then be evacuated or neutralized with the influx of colder fluid. This embodiment would allow for a very low-profile design and would not require any fluid heating element outside of the body.

In another variation, the cavity or lumen may be exposed to the hot water at a temperature of less than, e.g., 100 degrees Celsius, but greater than, e.g., 42 degrees Celsius, to allow for easier control of the treatment due a longer treatment period. Ranges for optimal hyperthermic treatment include temperatures between, e.g., 42 and 100 C and exposure periods ranging from, e.g., 15 seconds to 15 minutes. In this embodiment, treatment may be effected with an active (e.g., Methotrexate) or inactive fluid at a temperature of, e.g., 90 degrees C., for a period of, e.g., 5-60 seconds, depending on the depth of penetration desired.

Figure 11:
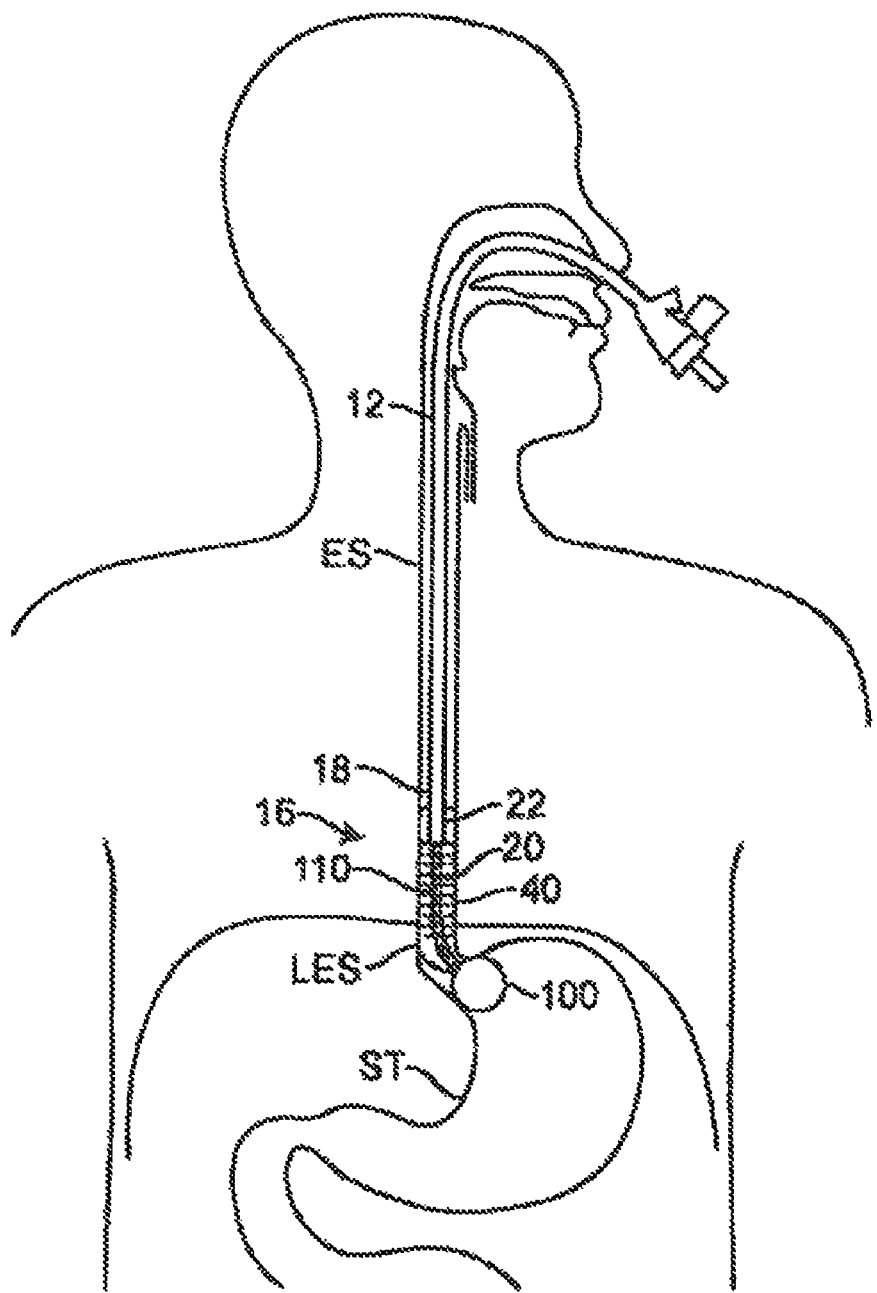
FIG. 11 shows another example where the treatment fluid is introduced between the deployed balloons for treatment.

FIG. 11 shows another example of an endoscopic balloon sheath which may be used to provide proximal occlusion of the treatment area 40 and may house one or more of the temperature and pressure sensors. This variation may incorporate a stirring/agitating or recirculation mechanism 110 incorporated into the device which may actuated within the treatment area 40 once the treatment fluid has been introduced to allow for even cooling/heating. The distal occlusion balloon 100 may be inflated within the stomach ST and pulled proximally with controlled traction against the gastric portion of the lower esophageal sphincter LES, as previously described.

In this example, a chilled liquid lavage (or vapor infusion) may then be initiated and the tissue ablated via freezing. A pre-treatment lavage, e.g., a hypertonic, hyperosmotic saline solution, may be introduced with above freezing temperatures followed by a sub-zero temperature lavage to ablate the tissues within the treatment area 40. The hypertonic, hyperosmotic fluid may achieve temperatures down to, e.g., −40 degrees C., without creating ice crystals in the treatment area 40 due to the pre-treatment lavage removing any free water. The treatment fluid following the pre-treatment lavage may have temperatures of, e.g., −2 degrees C. to −40 degrees C., for ablation or more particularly a temperature range of, e.g., −5 degrees C. to −20 degrees C. This temperature range may allow for freezing and crystal formation in the exposed tissues without damaging the underlying submucosa (which is protected by the circulation of body temperature blood that prevents freezing). This temperature range can also be easily achieved with hypersalination of aqueous fluid using sodium chloride and may inhibit any undesired damage to tissues with brief contact. Also, the use of a heavily salinated or other sub-zero solution lavage may provide optimal sealing of the occluding balloons in that any sub-zero temperatures outside of the pre-lavaged treatment zone may form an impaction of ice crystals and prevent any further fluid flow outside of the treatment zone. This hypersalinated water solution is but one freezing solution, though, and any aqueous or non-aqueous liquid or vapor that can be infused and extracted at this temperature could be used. Alternatively, cryoablative fluid can simply comprise nitrous oxide ($N_2O$) or be formed by cooling ethanol or another aqueous or lipophilic fluid with subzero cooling temps with compressed gas or dry ice. In another alternative, compressed $CO_2$ or dry ice may be introduced into the fluid (e.g., ethanol, butylenes glycol, propylene glycol, etc) to cool it to, e.g., −50 degrees C. or below.

Despite the potential for toxicity, ethanol may be used for a liquid lavage since ethanol resists freezing down to −118 C and is relatively biocompatible although ethanol is dose dependent for toxicity. A liquid lavage with about 75% to 99.9% ethanol concentrations may be utilized to good effect and have been demonstrated to show that a freeze layer develops very rapidly which also inhibits further ethanol absorption. For instance, a concentration of 95% ethanol may be introduced at a temperature of about, e.g., −80 to −50 degrees C., for a treatment time of about, e.g., 5 minutes, utilizing 0.25 to 0.5 liters of the cryogenic fluid. An ethanol copper composition may also be very useful since ethanol resists freezing whereas aqueous fluids will freeze and expand thereby moving the metal particle out of direct contact with the tissue.

In the event that nitrous oxide is used as the cryogenic fluid, the nitrous may be introduced through a nozzle or spray at a pressure of, e.g., 600-800 psi, at a temperature of about −88 degrees C. Such a temperature and pressure may be utilized for a treatment time of about, e.g., 3 minutes.

The use of a subzero solution within this range may also allow for fine control of the treatment depth as tissue damage would not begin to occur until a temperature differential of about 37 degrees C. is achieved (assuming a body temperature of 37° C.), but once this threshold is reached tissue damage occurs rapidly due to ice crystal formation. In contrast, tissue damage is on a continuous spectrum with hyperthermia and damage may begin to occur at a temperature differential of, e.g., 5 degrees C. Thus, the ability of the vasculature to protect the underlying tissues from damage is greatly reduced due to the small difference between the temperature of protective blood versus the temperature of the ablating fluid. With hypothermic lavage, the protective blood may differ by, e.g., 37 degrees C., in temperature and may thus allow for control of ablation depth based on the temperature of the fluid lavage and the time of exposure.

Figure 12:
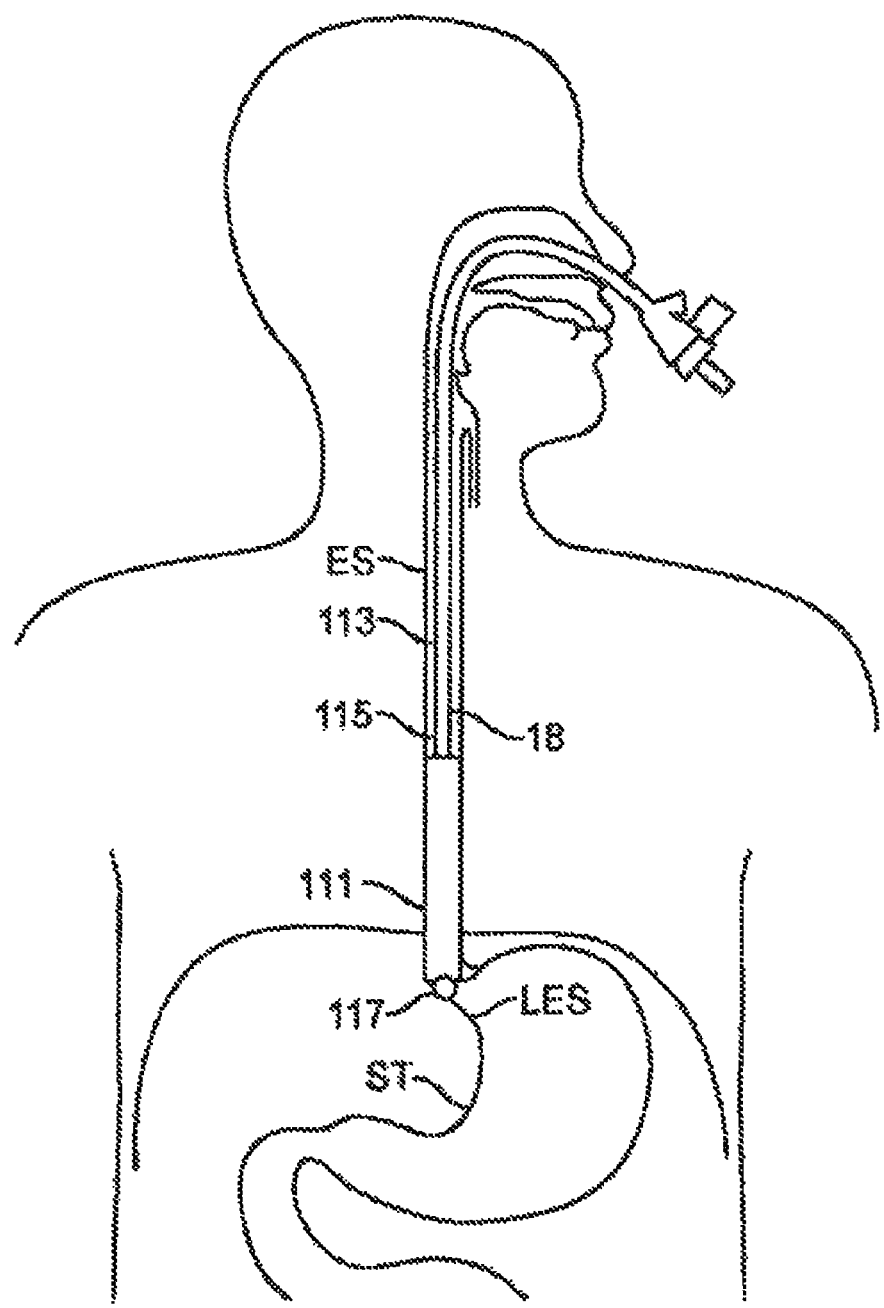
FIG. 12 shows another example of an adjustable size balloon device for treatment of the esophagus.

FIG. 12 illustrates another variation where a conforming balloon 111 having an adjustable size in diameter as well as in length may be positioned along or near the distal end of the catheter 18. The conforming balloon 111 may be advanced within the esophagus (shown here in the esophagus but applicable to any cavity) in a collapsed state. Once the balloon 111 has been desirably positioned along the length of the esophagus ES to be treated, the catheter 18 may optionally utilize a vacuum which may be drawn along the entire length of the balloon 111 through perforations or openings in the balloon 111 to serve as a safeguard to prevent migration of ablation liquid, gas, and/or conductive material in the event of balloon rupture. The vacuum may also be utilized to remove air, fluids or particulate between the outer wall of the balloon 111 and the tissue to improve contact and thermal transfer from the hyperthemic or cryogenic fluid and to the tissue. Additionally and/or alternatively, a distal vacuum may be drawn through a distal port 117 distal to the balloon 111 either alone or in conjunction with a proximal vacuum port 115 proximal to the balloon 115.

With the catheter 18 and balloon 111 desirably positioned for treatment, an insulating sheath 113 may be advanced over the catheter 18 and over the length of the balloon 111 to vary an inflation length of the balloon 111 emerging from the insulating sheath 113. The variable length of the inflated balloon 111 may be adjusted to allow for treatment of any varying lengths of the esophagus ES during a single ablation treatment. Such a design may prevent dangerous ablation overlap zones of ablated tissue.

The balloon 111 itself may be comprised of a compliant or non-compliant material but in either case be capable of directly contacting the tissues to be ablated. The balloon 111 may accordingly be filled with a hyperthemic or cryogenic material and/or may use liquid, gas, and/or conductive solids, as described herein.

Although illustrated esophageal therapy, this therapy could be used in any body cavity/lumen for therapeutic purposes including, but not limited to, gastrointestinal therapy, stomal tightening (e.g., post bariatric surgery), urogynecologic uses (treatment of cervical pre-cancers or cancers, endometrial lining treatment, stress incontinence therapy), prostate therapy, intravascular therapy (e.g., varicose veins) or treatment of any other body cavity/lumen. In the event that an entire body cavity is being treated (e.g., the entire uterus) a single balloon system may suffice to exclude the entire cavity. The fluid cycling or dwell may then be accomplished with use of a pressure-controlled exposure of the cavity or lumen.

FIGS. 13A and 13B show another example of how the system may be introduced into, e.g., a uterus UT, through the cervix for treatment via the lavage catheter 20. In this example, the catheter 20 may have a diameter of about, e.g., 8 mm, or in other examples, a diameter of about, e.g., less than 6 mm. Infusion of the lavage fluid may fully distend or partially distend the uterine walls. Optionally, catheter 20 may incorporate a tip 120 to perform one or more functions including, e.g., an expandable cage or scaffold to prevent direct exposure of a cryoprobe to the tissue walls of the uterus UT, an agitator or recirculator to ensure even distribution of cryoablation effect, etc. As previously described, the system may be used with lavage or with infusion then cryoprobe chilling of fluid. In an alternate embodiment, infusion of an antifreeze fluid and insertion of the cryprobe may be done separately with chilling of the anti-freeze done after the cryoprobe insertion.

In this and other examples, the therapy may be guided by time/temperature tracking or visualization (e.g., hysteroscope, endoscope, ultrasound, etc.). Pressure may be regulated by a pressure sensor in line with the infusion or extraction lumen or a dedicated pressure lumen in a multi-lumen catheter. Additionally, pressure may also be regulated by limiting infusion pressure (e.g., height of infusion bag, maximum pressure of infusion pump, etc.). Any organ, body cavity or lumen may be treated using the described lavage and/or infusion/cryoprobe technique described here for the uterus.

Figure 14A:
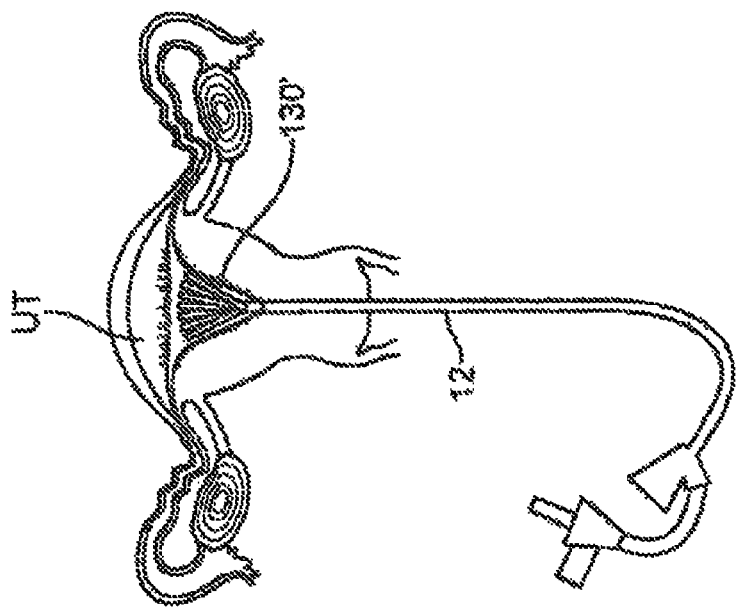
FIGS. 14A and 14B show yet another example of conductive lattice/cage deployed for cryoablative treatment.
Figure 14B:
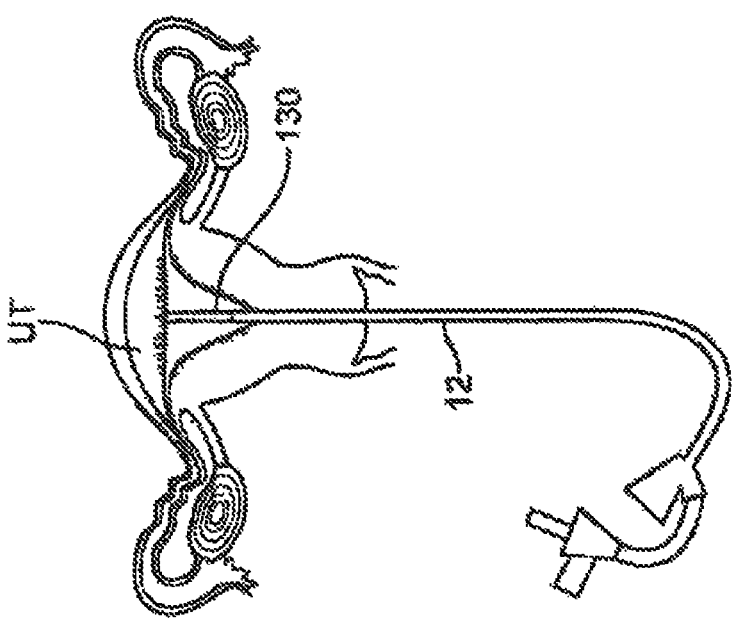

FIGS. 14A and 14B illustrate another variation of a treatment system which utilizes a thermally conductive array of fibers, cage, or lattice 130 which may be deployed within the uterus UT. In this variation, the endoscope 12 may be advanced through the cervix and at least partially into the uterus UT where the array of fibers or lattice 130 may be deployed from the endoscope 12 distal end where the array 130 may be positioned in a compressed state for delivery, as shown in FIG. 14A. The array 130 may be advanced into the uterus UT where it may then be expanded into a deployed configuration 130', as shown in FIG. 14B. The individual cryogenic probes of the expanded array 130' may be in fanned out relative to the distal end of the endoscope 12 in various directions to come into direct contact or close proximity to the tissue to be treated.

Following deployment, the deployed array 130' may be cooled rapidly to transmit the heat within the uterine walls to the array 130' to provide a consistent cryoablative effect throughout the body cavity or lumen. The members of the array 130' may be cooled either via conductive cooling or by an infusion of a cooling fluid (as described herein) through the members of the array 130'. Similar to the conductive fluid, the cooled array 130' may provide for the consistent ablation of the entire lumen with a single application of the array 130'. The individual members of the array 130'

Additionally and/or alternatively, the array 130' may be used in conjunction with a fluid infusion and/or lavage in order to optimize therapy. One or more sizes and shapes of the array 130' may be available depending on the size and shape of the cavity to be treated. Moreover, the array 130' may be formed from any material so long as it has a thermal conductivity greater than, e.g., 2 W/m-K, such as a metal with a relatively high thermal conductivity.

FIG. 15 shows another variation of a device which may utilize cryogenic lavage treatment within the uterus UT. In this example, the distal end of the endoscope 12 may be advanced through the cervix CV and into the uterus UT where a cryoprobe 140 may be deployed, as shown. One or more inflatable balloons 144 may be expanded, e.g., within the external os, or a balloon 142 along the outer surface of the endoscope 12 may be inflated within the length of the os itself. Alternatively, a single balloon (e.g., having an hour-glass or dumbbell shape) may be inflated to block both the external os and the length of the os itself. With the uterus UT obstructed, the cryogenic treatment or lavage may be performed within the uterine lumen.

Another variation is illustrated in FIG. 16 which shows endoscope 12 advanced through the cervix CV with the distal end 156 positioned within the uterine lumen. An optional balloon 152 located near the endoscope distal end may be inflated within the uterus UT and then pulled proximally against the internal os with a fixed amount of tension to obstruct the opening. Additionally and/or alternatively, a proximal balloon 154 positioned along the endoscope 12 proximally of where the cervix CV is located may also inflated to further provide for obstruction of the entire os. Then external cervical engagement portion, e.g., proximal balloon 154, may be fixed in place relative portion of the endoscope 12 spanning the cervical os to provide consistent tension. The proximal balloon 154 may also have a spring-type function to provide for consistent tension regardless of tissue relaxation and accommodation.

With the uterus UT obstructed, the endoscope 12 may then be used to provide for the cryogenic treatment or lavage. Optionally, the endoscope 12 may also incorporate one or more vacuum ports along the length of the shaft to seal and provide a safeguard against fluid flow out of the uterus UT.

Optionally, the uterine cornu may be temporarily obstructed to block the openings of one or both Fallopian tubes prior to the cryogenic treatment. The occlusive element(s) 158A, 158B may comprise, e.g., balloons, inserts, energy-based ablation to contract the aperture, hydrophilic or hydrophobic gel-based solutions, or any other modality that is capable of reversibly or irreversibly sealing the Fallopian tube. The optional Fallopian tube occlusion may be temporary or permanent (if sterility is desired).

Once the cryogenic procedure has been completed, the occlusive elements 158A, 158B may be removed or allowed to passively erode. Alternatively, they may be left occluded for those desiring sterility. Occluding the uterine cornu prior to a lavage may allow for greater fluid pressure and fluid flow within the uterus UT.

Figure 17B:
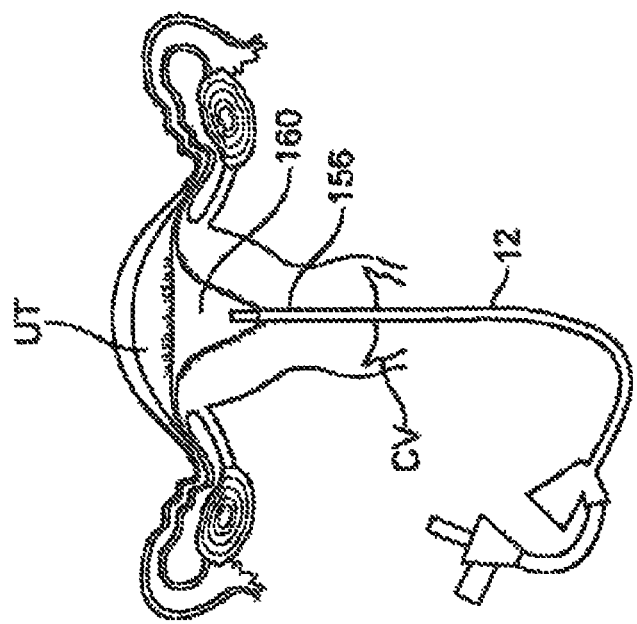
FIGS. 17A and 17B show another example of a device having a deployable low-pressure conforming balloon used for cryogenic treatment of the uterus.
Figure 17A:
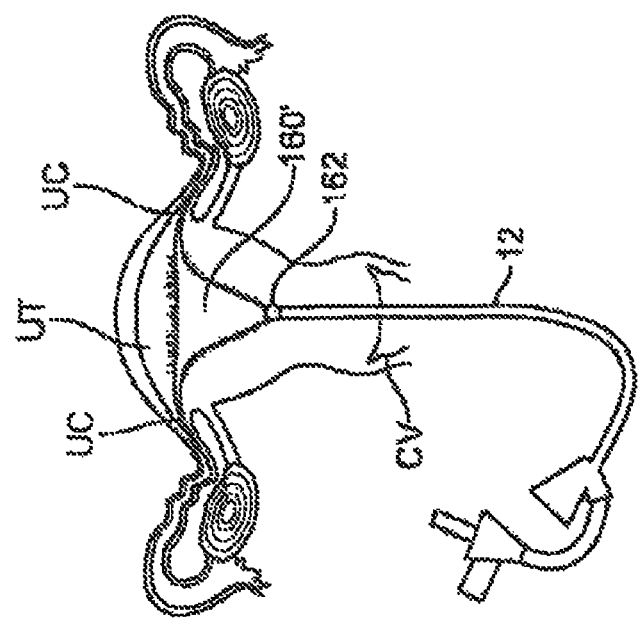

FIGS. 17A and 17B illustrate another variation of a low-pressure conforming balloon. In this variation, a conforming balloon 160 may be deployed from the distal end 156 of the endoscope 12 and then inflated with the cryogenic liquid/gas (as described herein) while in uterus UT. The balloon 160 may be formed to resist rupture at low and high temperatures and may be further configured to conform well to the anatomy of the uterus UT. For example, the balloon 160 when inflated may have a shape which approximates the lumen in which it is inflated and/or come in various sizes to accommodate different patient anatomies. In the present example, the expanded balloon 160' may be formed to taper and have two portions rounded portions for expanding into intimate contact at the uterine cornu UC, as shown, without painful deformation or distention of the uterus UT at a pressure, e.g., less than 150 mmHg.

Moreover, the expanded balloon 160' may have a wall which is relatively thin (e.g., 0.040 in. or less) to facilitate thermal conduction through the balloon. The balloon 160 may also be sufficiently thin such that folding of the balloon 160 on itself does not create a significant thermal barrier allowing for an even ablation in the event that a non-compliant balloon is used. For treatment, the expanded balloon 160' may be filled with the cryogenic liquid, gas or a thermally conductive compound (as described above) to subject the contacted tissue to either cryogenic and/or hyperthermic injury (e.g., steam, plasma, microwave, RF, hot water, etc).

Additionally and/or alternatively, the balloon 160' may also be used to transmit photodynamic therapy light to the uterus UT or esophagus ES. This modality may be used to achieve ablation of any body cavity or lumen.

Additionally, one or more vacuum ports may be used anywhere along the length of the shaft to seal and provide a safeguard against fluid flow out of the uterus UT in the event of balloon rupture. Additionally, one or more inflatable os balloon 160 may also be used to block the internal or external os, as also described above.

Figure 18B:
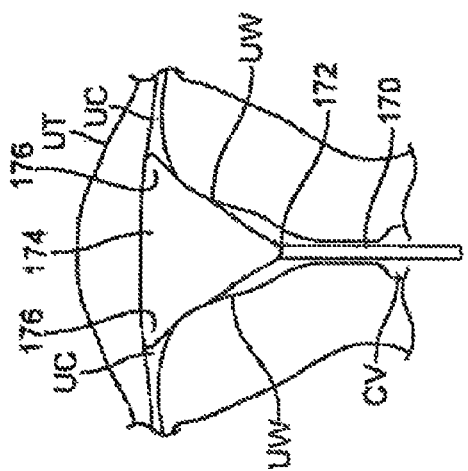
FIGS. 18A to 18D show another example of a conforming balloon which may also be filled partially or completely with a conductive material for cryoablative treatment.
Figure 18D:
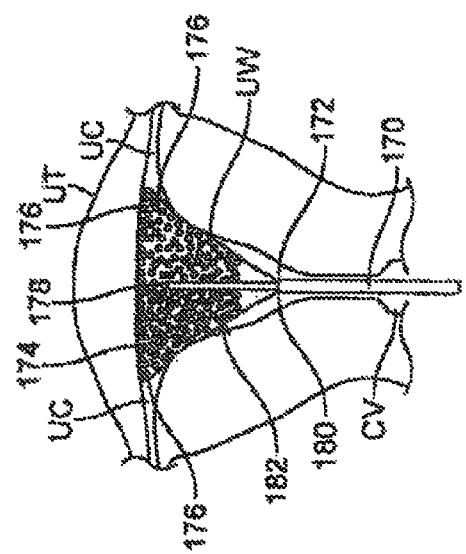
Figure 18A:
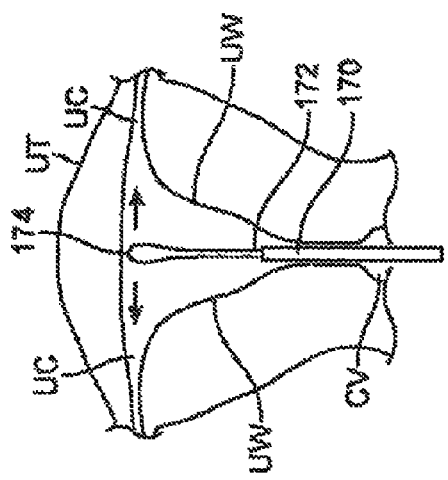

In another variation, to facilitate the balloon expanding and conforming readily against the tissue walls of the uterus UT, the balloon may be inflated with a gas or liquid. Alternatively, as shown in FIGS. 18A to 18D, the balloon may be filled partially or completely with a conductive material. As shown in FIG. 18A, once the elongate shaft 170 has been introduced through the cervix CV and into the uterus UT, the distal opening 172 of the shaft 170 may be positioned distal to the internal os and balloon 174 may be deployed either from within the shaft 170 or from an external sheath (described below in further detail). The balloon may be deployed and allowed to unfurl or unwrap within the uterus UT, as shown in FIG. 18B. The cooling probe 178 may be introduced through the shaft 172 and into the balloon interior (or introduced after insertion of the conductive elements).

Because the balloon 174 is used to contact the tissue and thermally conduct the heat through the balloon, the balloon material may be comprised of various materials such as polyurethane, fluorinated ethylene propylene (FEP), polyether ether ketone (PEEK), low density polyethylene, polyethylene terephthalate (PET), polyvinylidene fluoride (PVDF), or any number of other conformable polymers. Moreover, the balloon material may have a thickness which remains flexible and strong yet sufficiently thermally conductive, e.g., about 0.0005 to 0.015 in. Such a thickness may allow for the balloon to remain supple enough to conform desirably to the underlying tissue anatomy and may also provide sufficient clarity for visualizing through the material with, e.g., a hysteroscope.

Figure 18C:
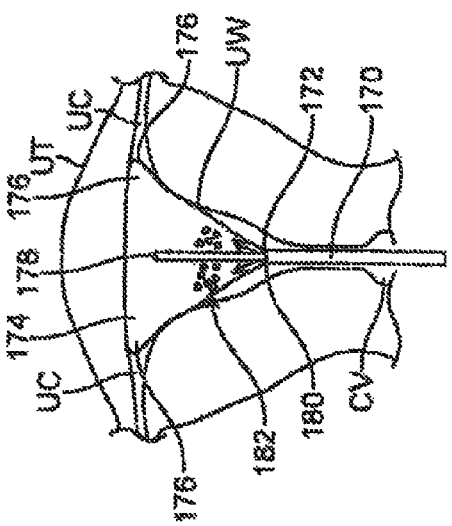

The conductive elements 182 may be introduced into the balloon interior through an annular opening 180 within the distal end 172 of the shaft, as shown in FIG. 18C, until the balloon 174 is at least partially or completely filled with the elements 182. The conductive elements 182 may generally comprise any number of thermally conductive elements such as copper spheres or some other inert metal such as gold. These conductive elements 182 may be atraumatic in shape and are small enough to fill the balloon interior and conform the balloon walls against the uterine walls UW to ensure consistent contact with the tissue, e.g., about 20 ml in volume of the elements 182. The conductive elements 182 may also help to fill any air pockets which may form particularly near the tapered portions 176 of the balloon and insulate the tissue from the ablative effects of the cryoablative fluid. For instance, the conductive elements 182 may be formed into spheres having a diameter of, e.g., 0.8 mm to 4 mm or larger. To ensure that conductive elements 182 are fully and evenly dispersed throughout the balloon interior, the elements 182 may be introduced through the shaft 170 via an ejector or push rod, auger, compressed air, etc. In particular, the conductive elements 182 may fill the tapered portions 176 of the balloon 174 to ensure that the balloon is positioned proximate to and in contact with the uterine cornu UC to fully treat the interior of the uterus UT, as shown in FIG. 18D.

With the conductive elements 182 placed within the balloon 174, the cryoablative fluid may be introduced within and through the balloon 174 such that the conductive elements 182 facilitate the thermal transfer from the contacted uterine walls UW. Once the cryoablative treatment has been completed, the conductive elements 182 may be removed through the shaft 170 via a vacuum force or other mechanical or electromechanical mechanisms and the balloon 174, once emptied, may also be withdrawn from the uterus UT.

Figure 19:
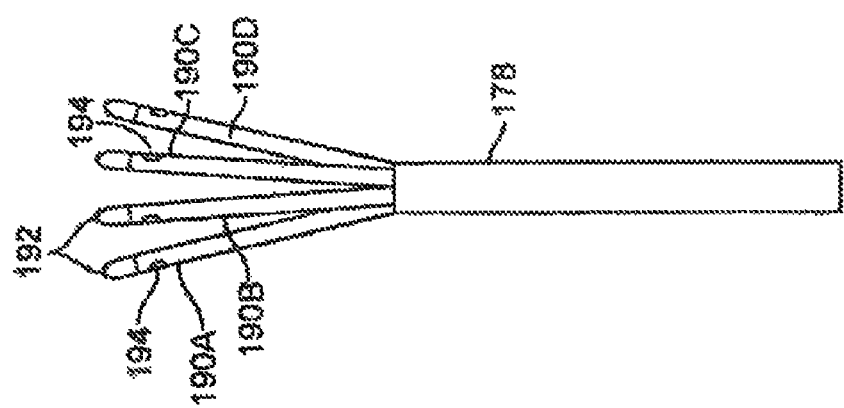
FIG. 19 shows another example of a cooling probe having one or more cooling members projecting from the distal end of a shaft.

The cooling probe 178 introduced into the interior of the balloon 174 may comprise a number of different configurations which facilitate the introduction of the cryoablative fluid into the balloon 174. One such variation, similar to the variation shown above in FIG. 14B, is illustrated in the detail view of FIG. 19. In this variation, the shaft 178 may have one or more cooling members 190A, 190B, 190C, 190D which project from the distal end of the shaft 178 at various angles. Although illustrated with four cooling members extending from the shaft 178, any number of cooling members may be used at a variety of different angles and lengths as desired. Moreover, the cooling members may be fabricated from a number of materials, e.g., polyimide, Nitinol, etc., which are sufficiently strong and temperature resistant for the relatively low temperature of the fluid. Each of the cooling members 190A, 190B, 190C, 190D in this example may each have an occluded tip 192 and at least one opening 194 defined along the side of the cooling member. The cryoablative fluid may be flowed through the shaft 178 and into each cooling member where the fluid may then be sprayed or ejected through the respective openings 194 for distribution throughout the interior of the balloon for cooling the contacted uterine tissue.

Figure 20:
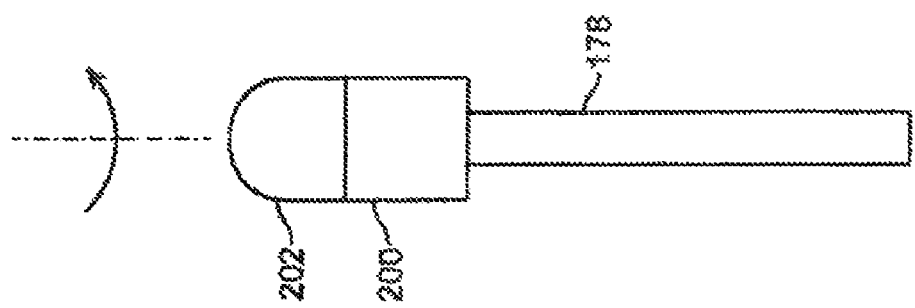
FIG. 20 shows another example of a cooling probe having a rotatable base and spray member.

Another variation of the cooling probe is illustrated in the detail view of FIG. 20 which shows elongate shaft 178 having a rotating base 200 and spray member 202 positioned upon shaft 178. The spray member 202 may have a surface which is meshed, latticed, perforated, etc. such that the cryoablative fluid introduced through the shaft 178 may enter the rotating base 200 and spray member 202 where it may be evenly dispersed through the spray member 202 and into the interior of the balloon 174 for treatment. The pressure of the fluid may rotate the base 200 about its longitudinal axis, as shown, to further facilitate the distribution of the cryoablative fluid within the balloon 174.

The cooling probe 178 as well as the balloon assembly may be variously configured, for instance, in an integrated treatment assembly 210 as shown in the side view of FIG. 21A. In this variation, the assembly 210 may integrated the elongate shaft 170 having the balloon 174 extending therefrom with the cooling probe 178 positioned translatably within the shaft 170 and balloon 174. A separate translatable sheath 212 may be positioned over the elongate shaft 170 and both the elongate shaft 170 and sheath 212 may be attached to a handle assembly 214. The handle assembly 214 may further comprise an actuator 216 for controlling a translation of the sheath 212 for balloon 174 delivery and deployment. The sheath 212 may be configured to have a diameter of, e.g., 5.5 mm or less, to prevent the need for dilating the cervix.

With the sheath 212 positioned over the elongate shaft 170 and balloon 174, the assembly 210 may be advanced through the cervix and into the uterus UT where the sheath 212 may be retracted via the handle assembly 214 to deploy the balloon 174, as shown in FIG. 21B. As described above, once the balloon 174 is initially deployed from the sheath 212, it may be expanded by an initial burst of a gas, e.g., air, carbon dioxide, etc., or by the cryogenic fluid. In particular, the tapered portions of the balloon 174 may be expanded to ensure contact with the uterine cornu. The handle assembly 214 may also be used to actuate and control a longitudinal position of the cooling probe 178 relative to the elongate shaft 170 and balloon 174 as indicated by the arrows.

Figure 21C:
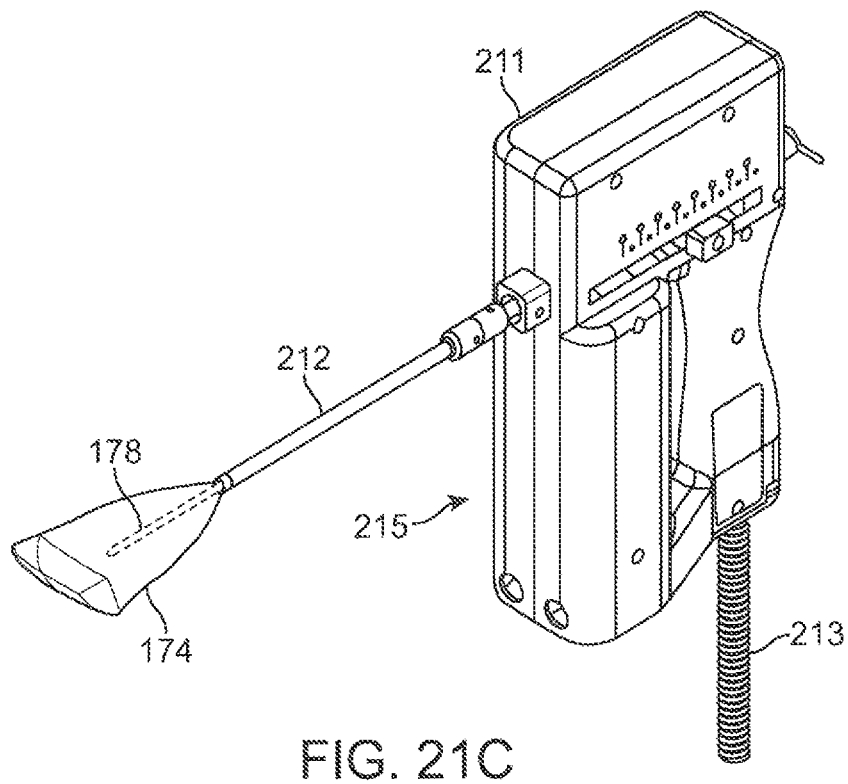
FIG. 21C shows a perspective view of a cryoablation assembly having a handle assembly which may integrate the electronics and pump assembly within the handle itself.

In another variation of the treatment assembly, FIG. 21C shows a perspective view of a cryoablation assembly having a handle assembly 211 which may integrate the electronics and pump assembly 215 within the handle itself. An exhaust tube 213 may also be seen attached to the handle assembly 211 for evacuating exhausted or excess cryoablative fluid or gas from the liner 174. Any of the cryogenic fluids or gases described herein may be utilized, e.g., compressed liquid-to-gas phase change of a compressed gas such as nitrous oxide ($N_2O$), carbon dioxide ($CO_2$), Argon, etc. The cooling probe 178 may be seen extending from sheath 212 while surrounded or enclosed by the balloon or liner 174. Hence, the handle assembly 211 with coupled cooling probe 178 and liner 174 may provide for a single device which may provide for pre-treatment puff-up or inflation of the liner 174, active cryoablation treatment, and/or post-treatment thaw cycles.

The handle assembly 211 may also optionally incorporate a display for providing any number of indicators and/or alerts to the user. For instance, an LCD display may be provided on the handle assembly 211 (or to a separate control unit connected to the handle assembly 211) where the display counts down the treatment time in seconds as the ablation is occurring. The display may also be used to provide measured pressure or temperature readings as well as any number of other indicators, symbols, or text, etc., for alerts, instructions, or other indications. Moreover, the display may be configured to have multiple color-coded outputs, e.g., green, yellow, and red. When the assembly is working through the ideal use case, the LED may be displayed as a solid green color. When the device requires user input (e.g. when paused and needing the user to press the button to re-start treatment) the LED may flash or display yellow. Additionally, when the device has faulted and treatment is stopped, the LED may flash or display a solid red color.

Figure 21D:
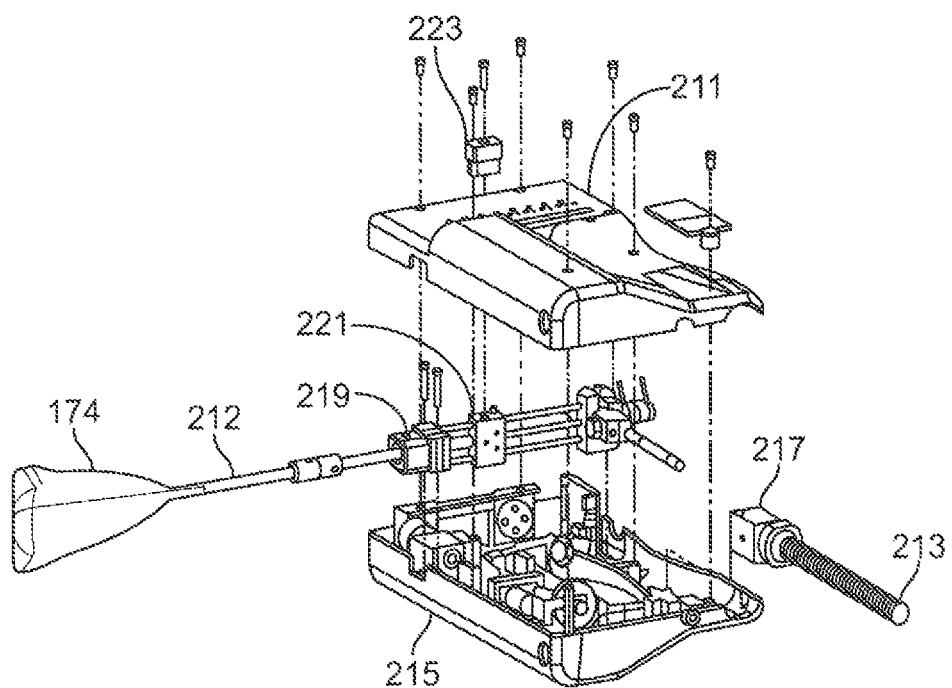
FIG. 21D shows the handle assembly in a perspective exploded view illustrating some of the components which may be integrated within the handle.

FIG. 21D shows the handle assembly 211 in a perspective exploded view to illustrate some of the components which may be integrated within the handle 211. As shown, the liner 174 and sheath 212 may be coupled to a sheath bearing assembly 219 and slider base block assembly 221 for controlling the amount of exposed treatment length along the cooling probe 178 (and as described in further detail below). An actuatable sheath control 223 may be attached to the slider base block assembly 221 for manually controlling the treatment length of the cooling probe 178 as well. Along with the electronics and pump assembly 215 (which may optionally incorporate a programmable processor or controller in electrical communication with any of the mechanisms within the handle 211), an exhaust valve 217 (e.g., actuated via a solenoid) may be coupled to the exhaust line 213 for controlling not only the outflow of the exhausted cryoablation fluid or gas but also for creating or increasing a backpressure during treatment, as described in further detail below.

Figure 21E:
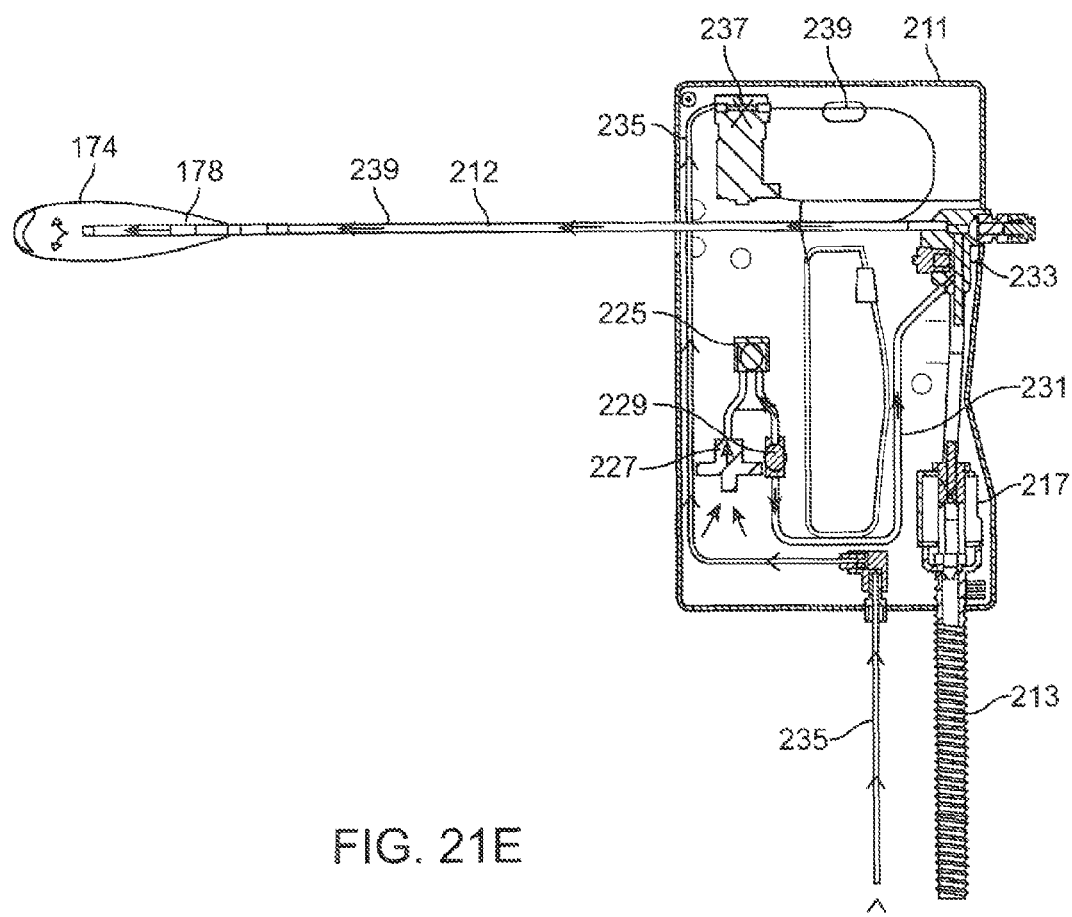
FIG. 21E shows an example of the system operation during a pre-treatment puff up process.
Figure 21F:
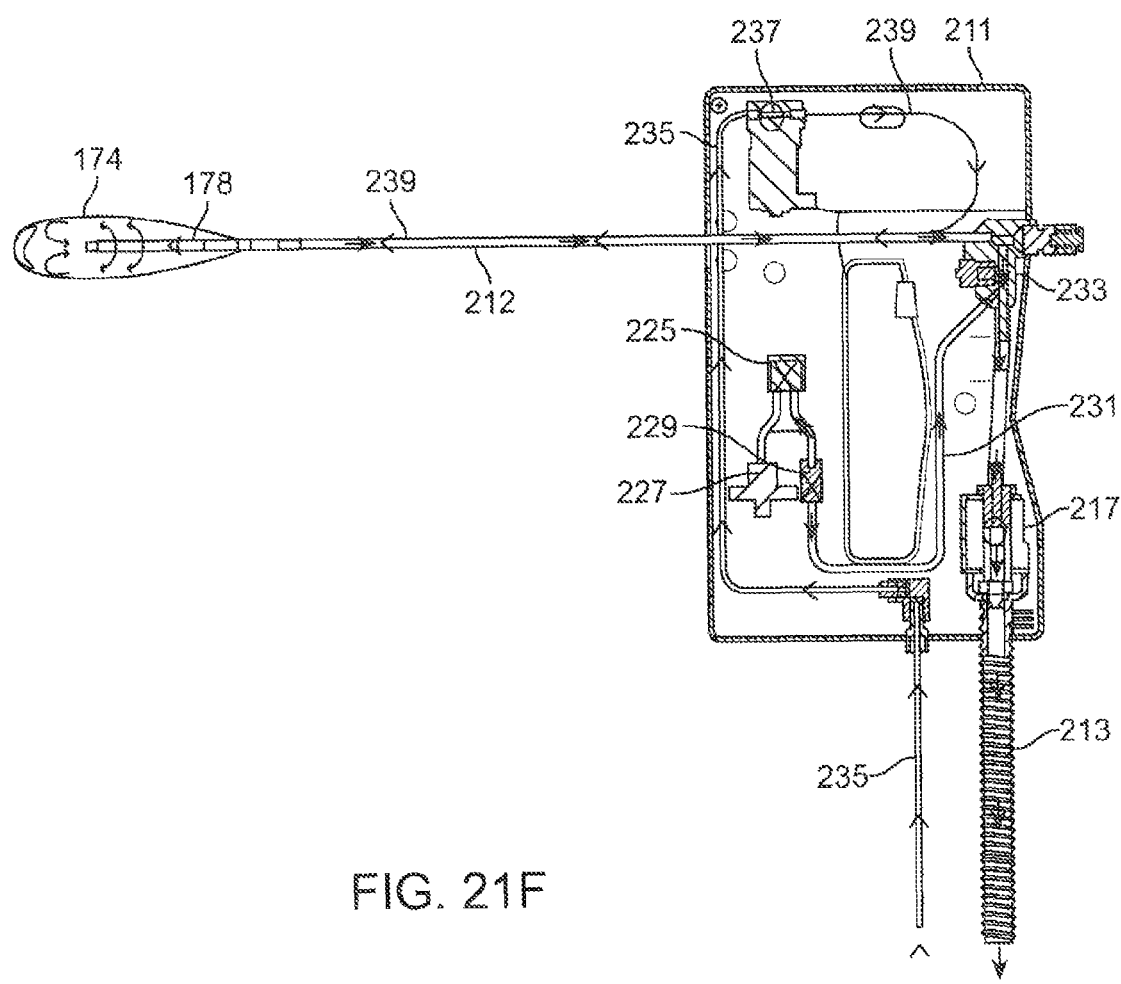
FIG. 21F shows an example of the system operation during a treatment process.
Figure 21G:
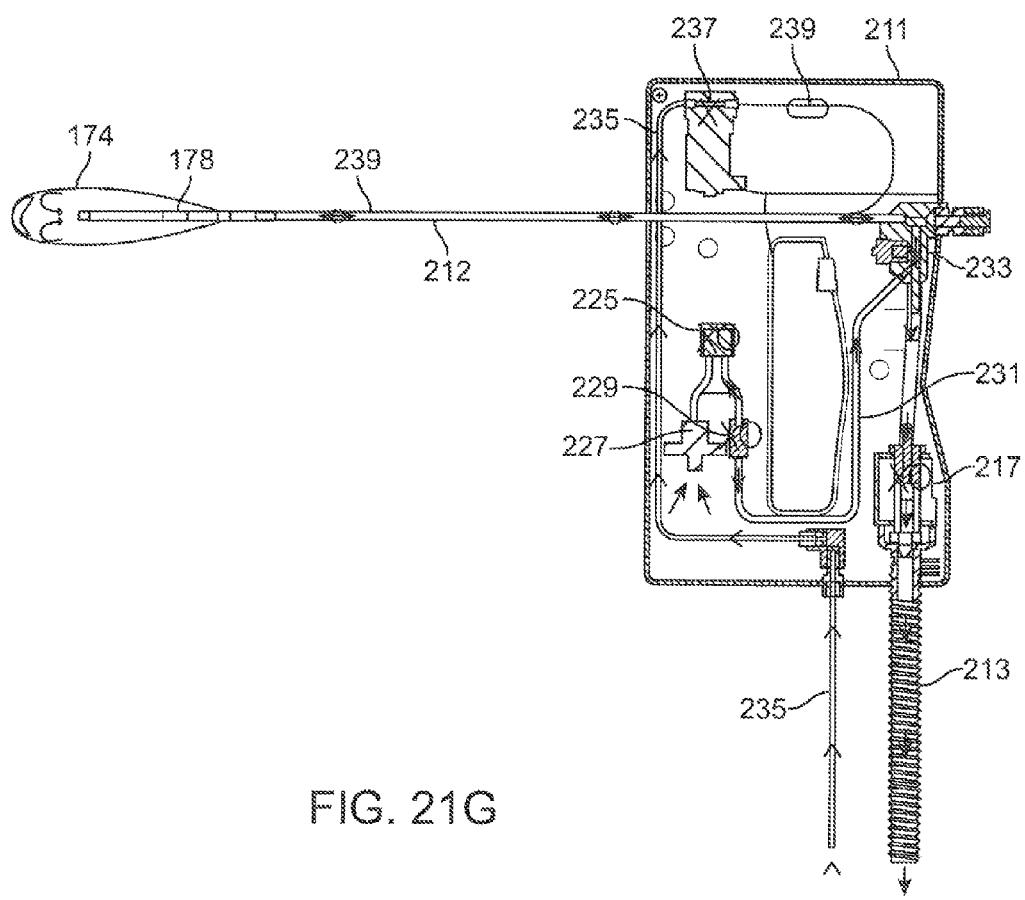
FIG. 21G shows an example of the system operation during a thawing and venting process.

In one example of how the handle assembly 211 may provide for treatment, FIGS. 21E to 21G illustrate schematic side views of how the components may be integrated and utilized with one another. As described herein, once the sheath 212 and/or liner 174 has been advanced and initially introduced into the uterus, the liner 174 may be expanded or inflated in a pre-treatment puff up to expand the liner 174 into contact against the uterine tissue surfaces in preparation for a cryoablation treatment. As illustrated in the side view of FIG. 21E, a pump 225 integrated within the handle assembly 211 may be actuated and a valve 229 (e.g., actuatable or passive) fluidly coupled to the pump 225 may be opened (as indicated schematically by an "O" over both the pump 225 and valve 229) such that ambient air may be drawn in through, e.g., an air filter 227 integrated along the handle 211, and passed through an air line 231 within the handle and to an exhaust block 233. The exhaust block 233 and air line 231 may be fluidly coupled to the tubular exhaust channel which extends from the handle 211 which is further attached to the cooling probe 178. As the air is introduced into the interior of the liner 174 (indicated by the arrows), the liner 174 may be expanded into contact against the surrounding uterine tissue surface.

A cryogenic fluid line 235 also extending into and integrated within the handle assembly 211 may be fluidly coupled to an actuatable valve 237, e.g., actuated via a solenoid, which may be manually closed or automatically closed (as indicated schematically by an "X" over the valve 237) by a controller to prevent the introduction of the cryoablative fluid or gas into the liner 174 during the pre-treatment liner expansion. An infusion line 239 may be fluidly coupled to the valve 237 and may also be coupled along the length of the sheath 212 and probe 178, as described in further detail below. The exhaust valve 217 coupled to the exhaust line 213 may also be closed (as indicated schematically by an "X" over the valve 217) manually or automatically by the controller to prevent the escape of the air from the exhaust block 233.

During this initial liner expansion, the liner 174 may be expanded in a gradual and controlled manner to minimize any pain which may be experienced by the patient in opening the uterine cavity. Hence, the liner 174 may be expanded gradually by metering in small amounts of air. Optionally, the pump 225 may be programmed and controlled by a processor or microcontroller to expand the liner 174 according to an algorithm (e.g., e.g. ramp-up pressure quickly to 10 mm Hg and then slow-down the ramp-up as the pressure increases to 85 mm Hg) which may be stopped or paused by the user. Moreover, the liner 174 may be expanded to a volume which is just sufficient to take up space within the uterine cavity. After the initial increase in pressure, the pressure within the liner 174 may be optionally increased in bursts or pulses. Moreover, visualization (e.g., via a hysteroscope or abdominal ultrasound) may be optionally used during the controlled gradual expansion to determine when the uterine cavity is fully open and requires no further pressurization. In yet another variation, the liner 174 may be cyclically inflated and deflated to fully expand the liner. The inflations and deflations may be partial or full depending upon the desired expansion.

In yet another alternative variation, the system could also use an amount of air pumped into the liner 174 as a mechanism for detecting whether the device is in a false passage of the body rather than the uterine cavity to be treated. The system could use the amount of time that the pump 225 is on to track how much air has been pushed into the liner 174. If the pump 225 fails to reach certain pressure levels within a predetermined period of time, then the controller may indicate that the device is positioned within a false passage. There could also be a limit to the amount of air allowed to be pushed into the liner 174 as a way to detect whether the probe 178 has been pushed, e.g., out into the peritoneal cavity. If too much air is pushed into the liner 174 (e.g., the volume of air tracked by the controller exceeds a predetermined level) before reaching certain pressures, then the controller may indicate the presence of a leak or that the liner 174 is not fully constrained by the uterine cavity. The liner 174 may also incorporate a release feature which is configured to rupture if the liner 174 is not constrained such that if the system attempts to pump up the liner 174 to treatment pressure (e.g., 85 mmHg), the release feature will rupture before reaching that pressure.

Once the liner 174 has been expanded sufficiently into contact against the uterine tissue surface, the cryoablation treatment may be initiated. As shown in the side view of FIG. 21F, the air pump 225 may be turned off and the valve 229 may be closed (as indicated schematically by an "X" over the pump 225 and valve 229) to prevent any further infusion of air into the liner 174. With the cryogenic fluid or gas pressurized within the line 235, valve 237 may be opened (as indicated schematically by an "O" over the valve 237) to allow for the flow of the cryogenic fluid or gas to flow through the infusion line 239 coupled to the valve 237. Infusion line 239 may be routed through or along the sheath 212 and along the probe 178 where it may introduce the cryogenic fluid or gas within the interior of liner 174 for infusion against the liner 174 contacted against the surrounding tissue surface.

During treatment or afterwards, the exhaust valve 217 may also be opened (as indicated schematically by an "O" over the valve 217) to allow for the discharged fluid or gas to exit or be drawn from the liner interior and proximally through the cooling probe 178, such as through the distal tip opening. The fluid or gas may exit from the liner 174 due to a pressure differential between the liner interior and the exhaust exit and/or the fluid or gas may be actively drawn out from the liner interior, as described in further detail herein. The spent fluid or gas may then be withdrawn proximally through the probe 178 and through the lumen surrounded by the sheath 212, exhaust block 233, and the exhaust tube 213 where the spent fluid or gas may be vented. With the treatment fluid or gas thus introduced through infusion line 239 within the liner 174 and then withdrawn, the cryogenic treatment may be applied uninterrupted.

Once a treatment has been completed, the tissue of the uterine cavity may be permitted to thaw. During this process, the cryogenic fluid delivery is halted through the infusion line 239 by closing the valve 237 (as indicated schematically by an "X" over the valve 237) while continuing to exhaust for any remaining cryogenic fluid or gas remaining within the liner 174 through probe 178, through the lumen surrounded by sheath 212, and exhaust line 213, as shown in FIG. 21G. Optionally, the pump 225 and valve 229 may be cycled on and off and the exhaust valve 217 may also be cycled on and off to push ambient air into the liner 174 to facilitate the thawing of the liner 174 to the uterine cavity. Optionally, warmed air or fluid (e.g., saline) may also be pumped into the liner 174 to further facilitate thawing of the tissue region.

As the spent cryogenic fluid or gas is removed from the liner 174, a drip prevention system may be optionally incorporated into the handle. For instance, a passive system incorporating a vented trap may be integrated into the handle which allows exhaust gas to escape but captures any vented liquid. The exhaust line 213 may be elongated to allow for any vented liquid to evaporate or the exhaust line 213 may be convoluted to increase the surface area of the exhaust gas tube to promote evaporation.

Alternatively, an active system may be integrated into the handle or coupled to the handle 211 where a heat sink may be connected to a temperature sensor and electrical circuit which is controlled by a processor or microcontroller. The heat sink may promote heat transfer and causes any liquid exhaust to evaporate. When the temperature of the heat sink reaches the boiling temperature of, e.g., nitrous oxide (around −89° C.), the handle may be configured to slow or stop the delivery of the cryogenic fluid or gas to the uterine cavity.

The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

Additionally and/or optionally, the handle 211 may incorporate an orientation sensor to facilitate maintaining the handle 211 in a desirable orientation for treatment. One variation may incorporate a ball having a specific weight covering the exhaust line 213 such that when the handle 211 is held in the desirable upright orientation, the treatment may proceed uninterrupted. However, if the handle 211 moved out of its desired orientation, the ball may be configured to roll out of position and trigger a visual and/or auditory alarm to alert the user. In another variation, an electronic gyroscopic sensor may be used to maintain the handle 211 in the desired orientation for treatment.

Figure 22A:
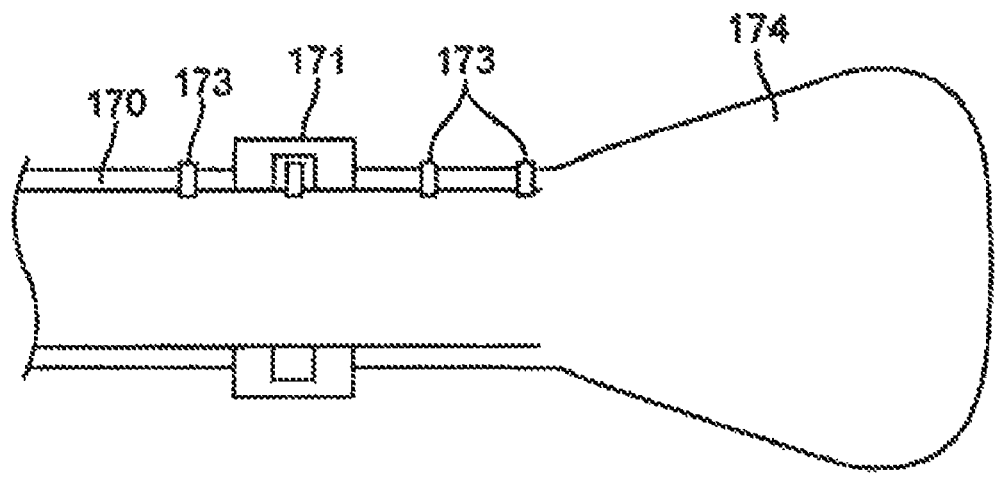
FIG. 22A shows a side view of a system which allows for adjustably setting a length of the balloon along the shaft.
Figure 22B:
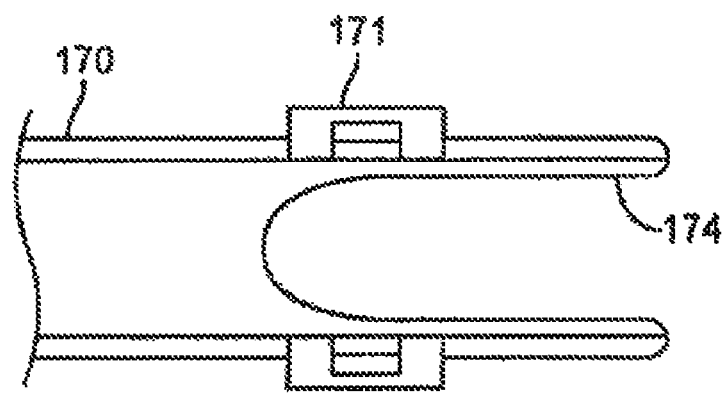
FIG. 22B shows a side view of the balloon everted within the shaft lumen for delivery.

FIG. 22A shows an example of one variation of a design of a system which may be used to deploy the balloon 174 into the uterus UT after properly setting the depth of the uterine cavity (or some other anatomical measurement). The elongate shaft 170 may have the balloon 174 attached along or near the distal end of the shaft 170 via a clamp or O-ring 171 placed along the outside of the shaft 170. One or more indicators 173 along the outer surface of the cannula may correspond to clinical measurements of the uterine length which may be measured by the clinician prior to a cryoablative procedure. With the measured uterine cavity known, the balloon 174 may be adjustably clamped along the length of the shaft 170 at any one of the indicators 173 which may correspond to the measured cavity length. With the balloon 174 suitably clamped in place, it may be pushed into the shaft lumen, as shown in FIG. 22B, using a pusher or some other instrument for delivery into the uterus UT. The elongate shaft 170 and balloon 174 may then be introduced into the uterus UT where the balloon 174 may be deployed from the shaft 170 and having a suitable length which may correspond to the particular anatomy of the patient.

The cooling probe positioned within the balloon 174 may be variously configured, as described above, and may include further variations. As illustrated in the perspective and side views of FIGS. 23A and 23B, respectively, the cooling probe assembly 220 in this variation may comprise an exhaust catheter 222 which may define a lumen 224 therethrough. While the diameter of the exhaust catheter 222 may be varied, its diameter may range anywhere from, e.g., 4.5 to 4.75 mm. The exhaust catheter 222 may be formed from various materials, such as extruded polyurethane, which are sufficiently flexible and able to withstand the lowered treatment temperatures. The distal end of the catheter 222 may have an atraumatic tip 226 which may be clear and/or which may also define a viewing window or opening through which an imaging instrument such as a hysteroscope 246 may be positioned. One or more supporting members or inserts 228, e.g., made from a polymer such as polysulfone, may be positioned throughout the length of the lumen 224 to provide structural support to the catheter 222 and to prevent its collapse. The inserts 228 have a relatively short length and define a channel therethrough through which a probe support 230 (e.g., flat wire, ribbon, etc.) may extend. The probe support 230 shown in this variation may comprise a flat wire defining one or more notches 232 along either side which may lock with one or more of the inserts 228 via insert supports 240 to stabilize the probe support 230.

The probe support 230 itself may be fabricated from a material such as stainless steel and may have a thickness of, e.g., 0.008 in. The probe support 230 may be supported within the lumen 224 via the inserts 228 such that the probe support 230 separates the lumen 224 into a first channel 242 and a second channel 244 where the cooling lumens 236 may be positioned along the probe support 230 within the second channel 244 while the first channel 242 may remain clear for the optional insertion of a hysteroscope 246. In the event that a hysteroscope 246 is inserted within first channel 242, the hysteroscope 246 may be advanced selectively along the catheter lumen 224 for visualizing the surrounding tissue or the hysteroscope 246 may be advanced through the length of the catheter 222 until it is positioned within a scope receiving channel 238 defined within the catheter tip 226.

Because of the thickness of the probe support 230 relative to its width, the probe support 230 may be flexed or curved in a single plane, e.g., in the plane defined by the direction of flexion 254 shown in FIG. 23B, while remaining relatively stiff in the plane transverse to the plane defined by the direction of flexion 254. This may allow for the probe 220 to be advanced into and through the patient's cervix CV and into the uterus UT while conforming to any anatomical features by bending along the direction of flexion 254 (e.g., up to 90 degrees or more) but may further allow the probe 220 to maintain some degree to rigidity and strength in the transverse plane. Additionally and/or alternatively, the catheter 222 may be actively steered along the direction of flexion 254, e.g., via one or more pullwires, to allow for positioning or repositioning of the catheter 222 within the balloon 174 to facilitate fluid distribution and/or visualization.

The probe 220 may further include one or more cooling lumens 236 which are positioned along the probe support 230 within the second channel 244. In this example, at least two cooling lumens are used where a first cooling lumen may extend through the probe 220 and terminate at a first cooling lumen termination 248 near the distal tip 226 and a second cooling lumen may also extend through the probe 220 adjacent to the first cooling lumen and terminate at a second cooling lumen termination 250 at a location proximal to the first termination 248. The termination points may be varied along the length of the probe 220 depending upon the desired length of the active cooling portion 252 of the probe 220, which may extend from the distal tip 226 to a length ranging anywhere from, e.g., 2 to 14 cm, along the probe length.

The cooling lumens 236A, 236B may be fabricated from any number of materials suitable to withstand the low temperature fluids, e.g., Nitinol, polyimide, etc. Moreover, the internal diameter of the cooling lumens may be made to range anywhere from, e.g., 0.010 to 0.018 in. In certain variations, the cooling lumens may have an outer diameter of, e.g., 0.020 in., and an internal diameter ranging from, e.g., 0.016 to 0.018 in., with a wall thickness ranging from, e.g., 0.002 to 0.004 in.

Because the cooling lumens 236 are located along the second channel 244, as separated by the probe support 230, one or more windows or openings 234 may be defined along the length of the probe support 230 to allow for the passage of any cryoablative fluid to pass through the openings 234 and to then directly exit the catheter 222 through the openings 260 defined along the catheter 222 body (as described below) and into the balloon interior. Alternatively, the cryoablative fluid may instead proliferate through the entire lumen 224 defined by the catheter 222 before exiting the catheter 222 body. These openings 234 may be cut-outs through the probe support 230 and may number anywhere from zero openings to six or more, as shown, and they may be configured in any number of sizes and shapes. Moreover, these openings 234 may be distributed in any spacing arrangement or they may be uniformly spaced, e.g., 0.320 in., depending upon the desired cooling arrangement.

Figure 24:
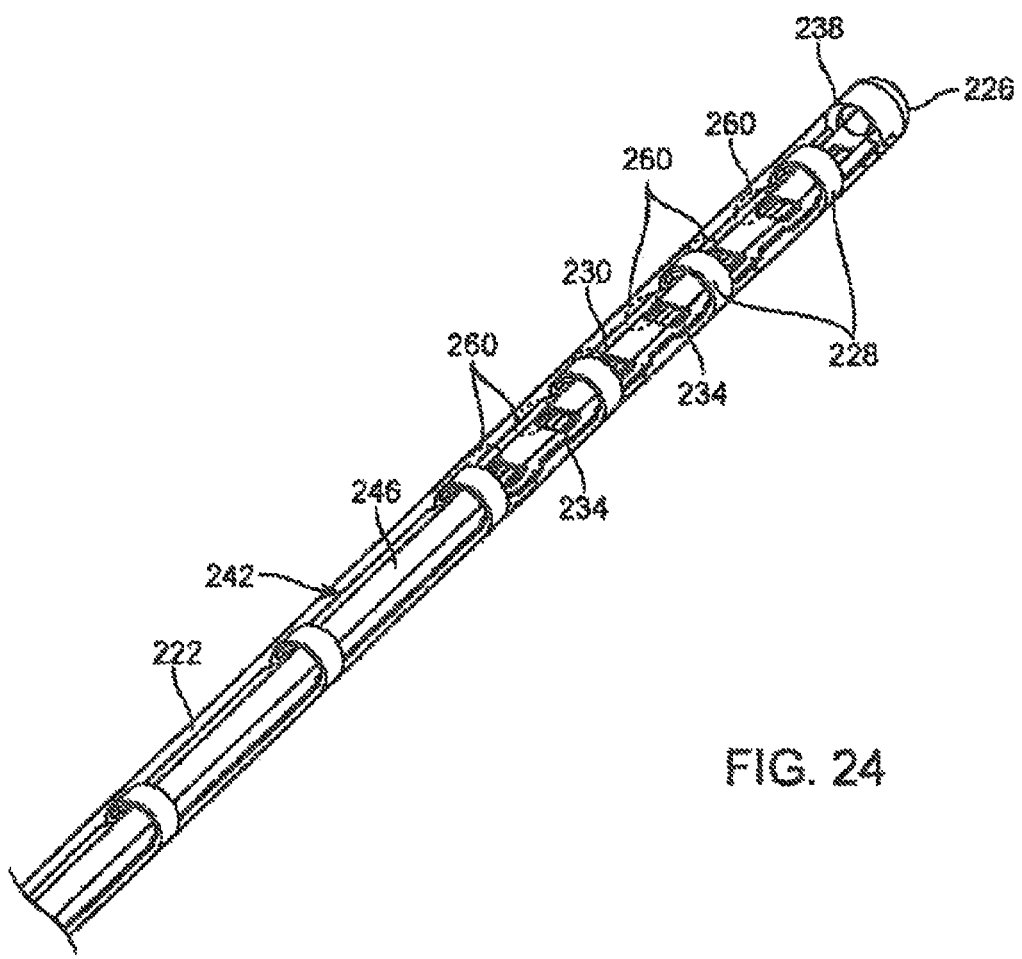
FIG. 24 shows a perspective view of the cooling probe assembly with one or more openings defined along the probe assembly.

The number of cooling lumens 236 may also be varied to number more than three lumens terminating at different positions along the active portion 252. Additionally, the activation of the cooling lumens for spraying or introducing the cryoablative fluid may be accomplished simultaneously or sequentially from each of the different cooling lumens depending upon the desired ablation characteristics. While the cooling lumens may simply define a distal opening for passing the fluid, they may be configured to define several openings along their lengths to further distribute the introduction of the cryoablative fluid. The openings 260 along the catheter body 222 for venting the cryoablative fluid into the balloon 174 are omitted from FIG. 23A only for clarity purposes but are shown in further detail in the following FIG. 24.

As the cryoablative fluid is initially introduced into the catheter lumen 242, the exhaust catheter 222 may also define one or more openings to allow for the cryoablative fluid to vent or exhaust from the catheter interior and into the interior of the balloon 174. As shown in the perspective view of FIG. 24, one or more openings 260 are illustrated to show one example for how the openings 260 may be defined over the body of catheter 222. The openings 260 may be positioned along a single side of the catheter 222 or they may be positioned in an alternating transverse pattern, as shown, to further distribute the cooling fluid throughout the balloon interior. In either case, the positioning of the openings 260 may be varied depending upon the desired cryoablation characteristics.

A cross-sectional end view of the cooling probe assembly 220 is shown in FIG. 25A illustrating the relative positioning of supporting insert 228 attached to the probe support 230 within the catheter 222. The two cooling lumens 236A, 236B are illustrated adjacently positioned along the probe support 230 although they may be positioned elsewhere within the catheter 222 and may also number one lumen or greater than two lumens. Moreover, an optional hysteroscope 246 is also illustrated positioned within the catheter 222 along the probe support 230. An end view of the distal tip 226 is also illustrated in FIG. 25B showing one variation where the distal tip 226 may define a viewing window 270 through which the hysteroscope 246 may be advanced for visualizing within the balloon 174 and uterus UT. In other variations, the viewing window 270 may be omitted and the distal tip 226 may be transparent for allowing visualization directly through the tip 226 by the hysteroscope 246.

With such an arrangement of the cooling probe assembly 220 positioned within the balloon 174 (as illustrated above in FIG. 21B), the assembly 210 may be used to treat the surrounding uterine tissue in close conformance against the balloon 174 exterior surface. Introduction of the cryoablative fluid, e.g., nitrous oxide, through the cooling probe 220 may allow for the ablation of the surrounding tissue to a depth of, e.g., 4 to 8 mm.

One example for a treatment cycle using a two cycle process may include the introduction of the cryoablative fluid for a treatment time of two minutes where the surrounding tissue is frozen. The fluid may be withdrawn from the balloon 174 and the tissue may be allowed to thaw over a period of five minutes. The cryoablative fluid may be then reintroduced and the tissue frozen again for a period of two minutes and the fluid may then be withdrawn again to allow the tissue to thaw for a period of five minutes. The tissue may be visually inspected, e.g., via the hysteroscope 246, to check for ablation coverage. If the tissue has been sufficiently ablated, the assembly 210 may be removed from the uterus UT, otherwise, the treatment cycle may be repeated as needed. In other alternatives, a single cycle may be utilized or more than two cycles may be utilized, as needed, to treat the tissue sufficiently. Furthermore, during the treatment cycle, a minimum pressure of, e.g., 40 to 80 mm Hg, may be optionally maintained by the cryogenic liquid or by a gas (e.g., air, carbon dioxide, etc.) to keep the balloon 174 and uterus UT open.

In yet another alternative, aside from having a catheter 222 made as an extruded lumen, the catheter may be formed into tubing 201 such as a hypotube fabricated from a material such as, e.g., stainless steel, nitinol, etc. A tubing 201 formed from a metal may provide additional strength to the catheter and may remove the need for any inserts to maintain a patent lumen. To increase the flexibility of the tubing 201, one or more slots 203 may be formed or cut along the body of the tubing 201, as shown in the example of FIG. 26A, which illustrates a perspective view of tubing 201 having one or more slots 203 cut transversely relative to the tubing 201. Aside from increased flexibility, the slots 203 may be aligned to provide for preferential bending or curvature along predetermined planes by the tubing while inhibiting the bending or curvature along other planes, e.g., planes transverse to the bending plane, similar to the preferential bending or curvature provided by the probe support 230.

The ends of the slots 203 may be formed to provide a separation 205 between the ends of the slots 203. FIG. 26B shows another variation where each of the transverse slots 203 may have a strain relief feature 207 formed at the distal ends of each slot 203 such that bending of the tubing 201 over the slotted region may occur with reduced stress imparted to the slots 203 and tubing 201. An additional feature may include optional tabs 209 which may be formed along the body of the tubing 201 to extend internally for holding a cooling lumen within the lumen of the tubing 201.

Another variation is shown in FIG. 26C which shows transverse slots 203 formed along the body of the tubing 201 where the slots 203 may be formed in an alternating pattern with respect to one another. FIG. 26D shows yet another variation where angled slots 211 may be formed relative to tubing 201. FIG. 26E shows another variation having one or more serpentine slots 213 for preventing pinching where a distal end of each slot 213 may have a transverse slot 215 formed. FIG. 26F shows another variation where one or more slots 217 having a transverse and longitudinal pattern may be formed along tubing 201.

FIG. 26G shows another variation where a transverse slot 219 may have a longitudinal slot 221 formed at its distal end. FIG. 26H shows yet another variation where one or more tapered slots 223 may be formed along tubing 201. FIG. 26I shows another variation where a transverse slot 219 may have a longitudinal slot 221 formed where each of the longitudinal slots 221 may be aligned longitudinally along the body of tubing 201. FIG. 26J shows another variation where transverse slots 219 may have longitudinal slots 223 aligned adjacent to one another and having rounded ends. FIG. 26K shows another variation where either a curved serpentine slot 225 or an angled slot 227 may be formed along the tubing 201. Alternatively, both curved serpentine slot 225 and angled slot 227 may both be formed. Another variation shows tubing 201 having a plurality of slots 229 formed into a lattice structure over the body of tubing 201.

Figure 27A:
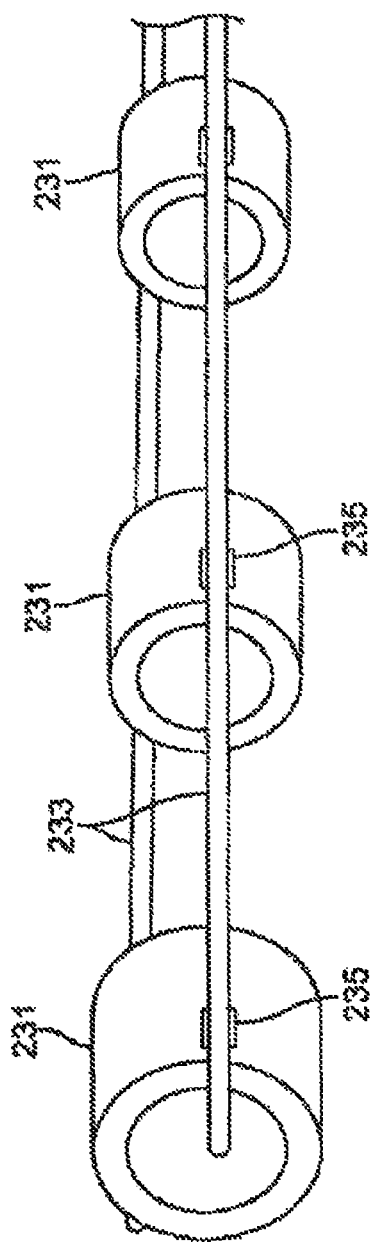
FIGS. 27A and 27B show perspective views of a cooling probe assembly utilizing one or more discrete ring members linearly coupled to one another.
Figure 27B:
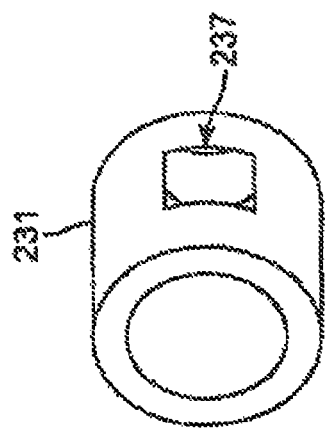

Aside from utilizing a continuous body of tubing 201 for the length of the cooling probe, discrete tubing reinforcing ring 231 may instead be formed from tubing 201. FIG. 27A shows an example where a plurality of reinforcing rings 231 may be separated into discrete ring elements and attached to one another in a linear manner with one or more longitudinal beam members 233 which may be attached to each reinforcing ring 231 at an attachment point 235, e.g., weld, adhesive, etc. One or more of the reinforcing rings 231 may be formed to have, e.g., a bent-in tab 237, for supporting beam 233 rather than utilizing a weld, adhesive, etc., as shown in the detail perspective view of FIG. 27B. The assembly of the reinforcing ring 231 and beams 233 may be covered with a membrane or other covering to form a uniform structure.

Figure 28A:
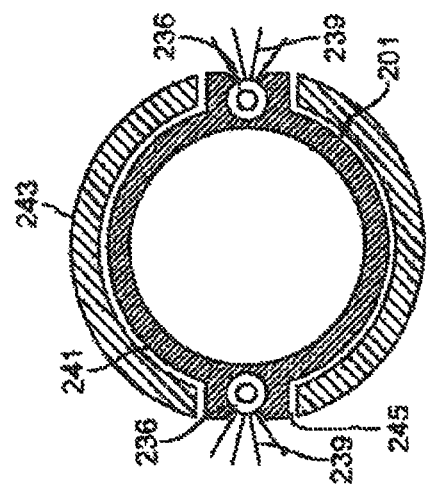
FIGS. 28A and 28B show cross-sectional end views of another variation of a cooling probe assembly coupled via a covering and/or insert members.

An example of a covering which may be used is shown in the end view of FIG. 28A which shows a portion of tubing 201 or reinforcing ring 231 and cooling lumens 236 positioned on either side of tubing 201 or reinforcing ring 231. A heat shrink 241 material may be placed over the probe assembly while maintaining clearance for openings 239 to allow for delivery of the cryoablative fluid.

Figure 28B:
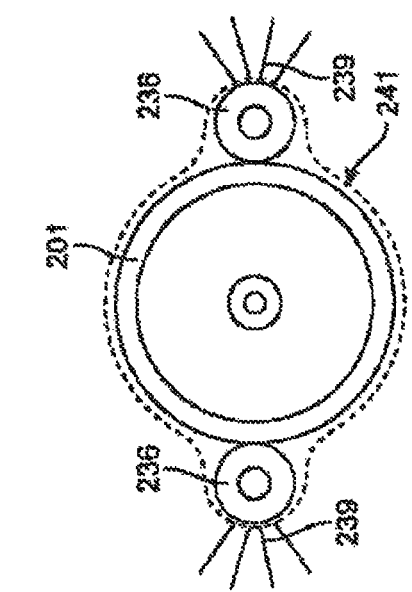
Figure 29:
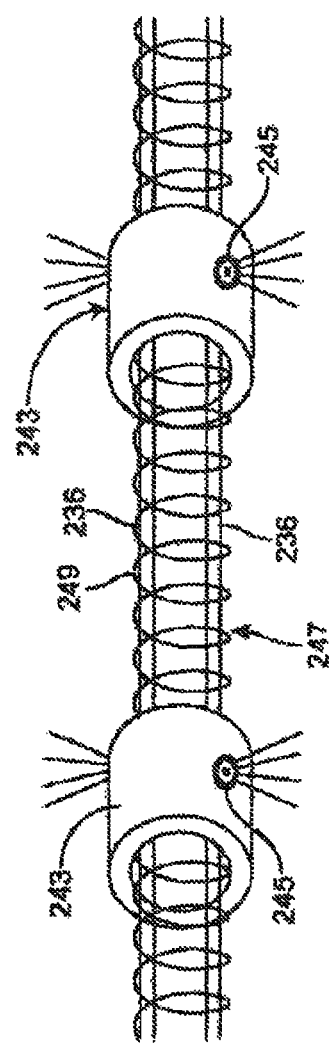
FIG. 29 shows a perspective view of another variation of a cooling probe assembly having one or more insert members coupled along a wound spring body.

Another variation is shown in the cross-sectional end view of FIG. 28B which shows the tubing 201 and respective cooling lumens 236 positioned within an insert 243 which define insert openings 245 for introducing the cryoablative fluid. Yet another variation is shown in the perspective view of FIG. 29 which may incorporate a wound spring 247 which may be tightly wound or packed to provide flexibility and to further provide a lumen 249 for the exhaust. One or more inserts 243 may be positioned longitudinally along the length of the spring 247 and the cooling lumens 236 may be routed through the spring 247 and coupled to each insert 243.

Figure 30A:
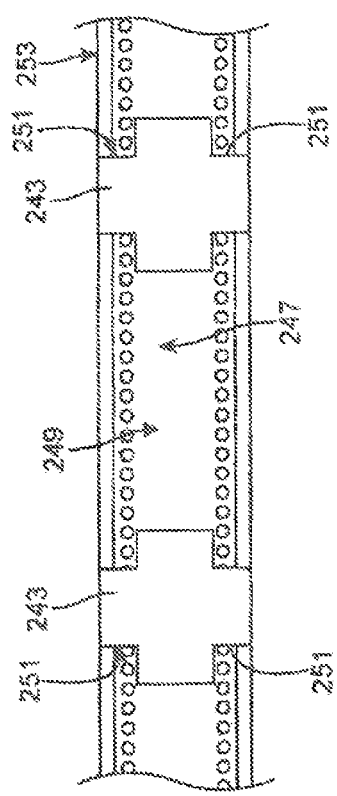
FIGS. 30A and 30B show cross-sectional side views of another variation of insert members supported along a spring body.
Figure 30B:
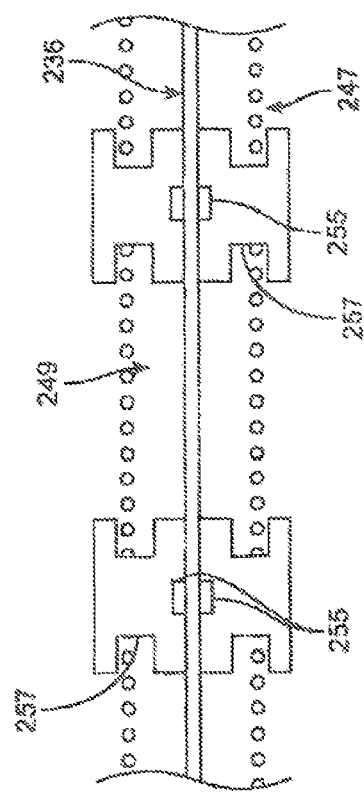

Another variation is shown in the partial cross-sectional side view of FIG. 30A which illustrates how one or more inserts 243 may each define a step 251 for securement to the spring 247. The entire assembly may then be covered by a covering 253, e.g., flexible extrusion. Each of the inserts 243 may remain uncovered by either the spring 247 or covering 253 to ensure that the cryoablative fluid has an unhindered pathway to the balloon interior. FIG. 30B shows another variation where each of the inserts 243 may define a respective receiving channel 257 on either side of the insert 243 for securement to the spring 247. An example of a cooling lumen 236 is shown attached to each of the inserts 243 via an attachment 255, e.g., weld, adhesive, etc.

Figure 31:
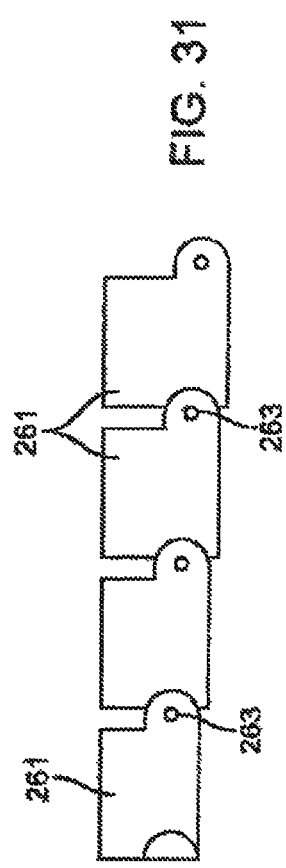
FIG. 31 shows a detail side view of one variation of a pivotable cooling lumen body.

Aside from increasing the flexibility of the tubing or cooling probe, the cooling lumen may be configured to increase its flexibility as well. An example is shown in FIG. 31 which shows a portion of a cooling lumen wall 261 having a plurality of pivoted attachments 263. Such an arrangement may allow for each segment of the cooling lumen wall 261 to pivot such that the cooling lumen cumulatively provides sufficient flexibility to bend and curve as the cooling probe assembly is advanced and positioned within the uterus. Such a cooling lumen may be incorporated into any of the probe variations described herein.

Figure 32:
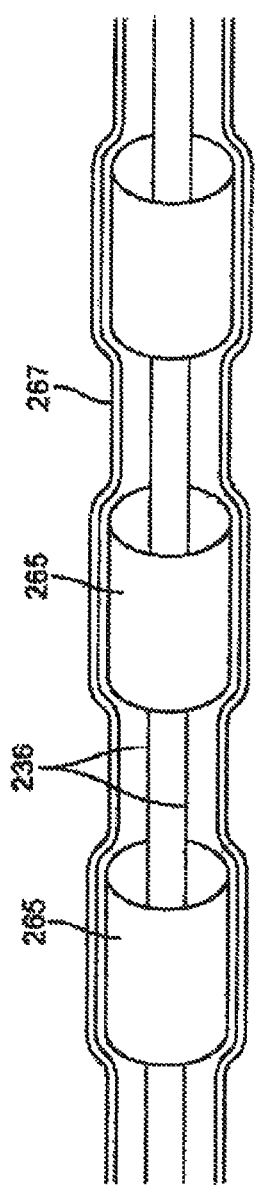
FIG. 32 shows a side view of another variation of one or more insert members having an integrated covering.
Figure 33:
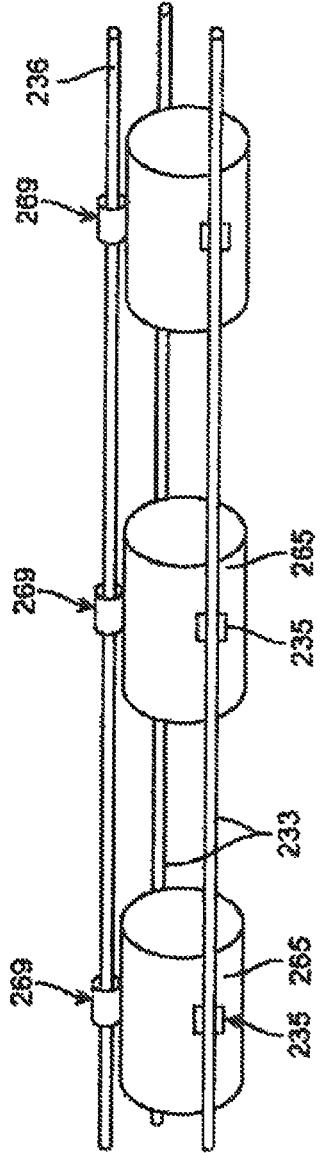
FIG. 33 shows a side view of yet another variation of one or more insert members having a slidable joint attached.

Another example of a cooling probe assembly is illustrated in the perspective view of FIG. 32 which shows discrete embedded insert 265 and one or more cooling lumens 236 attached to each respective insert 265 covered with a covering 267. In this example, the covering 267 may be implemented without any additional features or structures. FIG. 33 shows yet another example where individual inserts 265 may be aligned and coupled with one or more beams 233, as previously described. An additional sliding joint 269 may be attached or integrated along each insert 265 to provide support to one or more cooling lumens 236 which may be translatably positioned through each aligned sliding joint 269.

Yet another variation is illustrated in the side view of FIG. 34 which shows a wound spring element 271 having one or more cooling lumens 236 aligned longitudinally along the spring element 271. The one or more cooling lumens 236 may be attached to the spring element 271 via connectors 273 which may be aligned relative to one another to receive and secure the cooling lumens 236. A covering may be optionally secured over the spring assembly.

FIG. 35 shows another variation where spring element 271 may incorporate one or more respective inserts 243. In this variation, the spring element 271 has the one or more cooling lumens 236 coupled to the spring element 271 itself. FIG. 36 shows yet another variation where the spring element 271 and the one or more cooling lumens 236 (which may be coupled directly to the spring element 271), may have an optional secondary lumen 275 passing through the spring element 271 and optionally attached to the spring itself. The second lumen 275 may be sized for receiving an instrument such as a hysteroscope 246. The second lumen 275 may provide a redundant liquid or gas pathway should the primary lumen become partially or fully obstructed. The redundant pathway may exist between the optional instrument, e.g. hysteroscope, and primary lumen or within the full second lumen 275.

Figure 37:
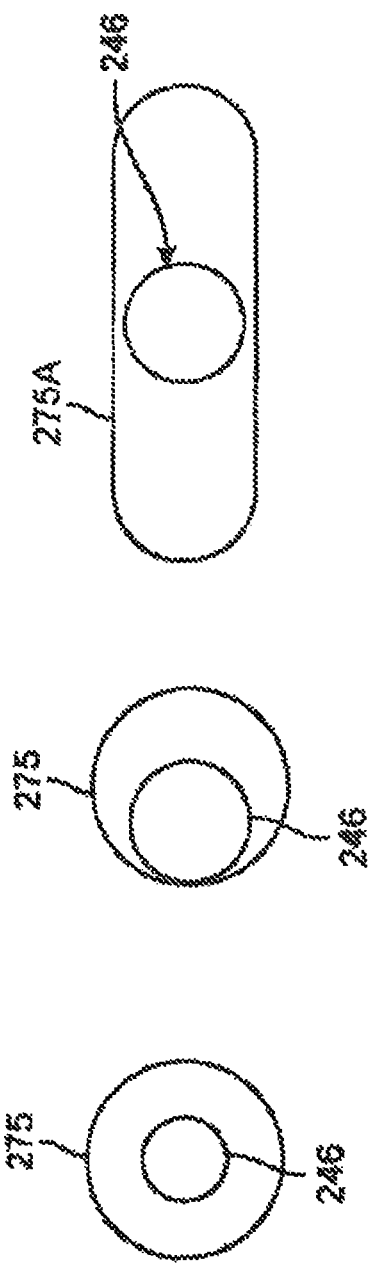
FIG. 37 show cross-sectional end views of variations of the secondary lumen.

The secondary lumen 275 may be shown in various cross-sections in the end views of FIG. 37. A first variation is illustrated shown secondary lumen 275 having a circular cross-sectional area with a hysteroscope 246 passed through a center of the lumen 275. A second variation is illustrated where the hysteroscope 246 may be passed along a side of the lumen 275 and a third variation is illustrated showing a secondary lumen 275A having an elliptical cross-sectional area.

Another variation for a cooling probe assembly is shown in the perspective views of FIGS. 38A to 38C. In this variation, the catheter body 222 is omitted for clarity purposes only but a main delivery line 280 is shown extending through the catheter with at least two side delivery lines 282, 284 positioned near the surface of the catheter body, as shown in FIG. 38A. The main delivery line 280 may be in fluid communication with the side delivery lines 282, 284 via a junction 288, shown in FIG. 38B, near or within the distal tip 226. As the cryoablative fluid is introduced into the main delivery line 280, the fluid in the side delivery lines 282, 284 may be vented through one or more openings 286 defined therealong for venting through and into the catheter and balloon interior. An optional mandrel 290, as shown in FIG. 38C, may be slidingly fitted within each of the side delivery lines 282, 284 and actuated automatically along with the retraction of the sheath 212 or by the user to slide along the interior of one or both side delivery lines 282, 284 to selectively obstruct the openings 286 and thereby control the amount of cryoablative fluid delivered. As shown, one or more obstructed openings 292 may be blocked by the mandrel 290 by selectively sliding the mandrel 290 accordingly. In other variations, rather than using mandrels inserted within the delivery lines 282, 284, a sheath or mandrel placed over the delivery lines 282, 284 may be used instead to achieve the same results.

As described above, the retraction of the mandrel 290 may be optionally actuated to follow along with the retraction of the sheath 212. Accordingly, the retraction of the mandrel 290 may occur simultaneously with the retraction of the sheath 212 but the retraction may optionally occur at different rates as the amount of cryoablative fluid delivered may be related to the length of the uterine cavity to be treated. For instance, a sheath retraction of, e.g., 7 cm, may result in 10 unobstructed openings 286 whereas a sheath retraction of, e.g., 4 cm, may result in, e.g., 6 unobstructed openings 286.

Figure 40A:
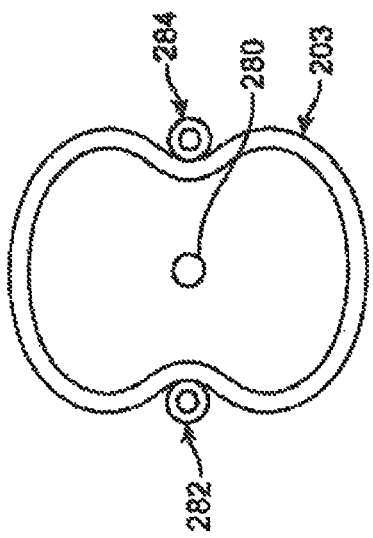
FIGS. 40A and 40B show cross-sectional end views of variations of the exhaust lumen and the respective cooling lumens.
Figure 40B:
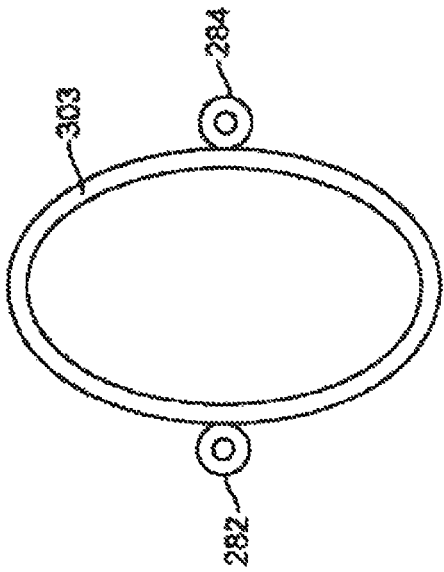
Figure 39:
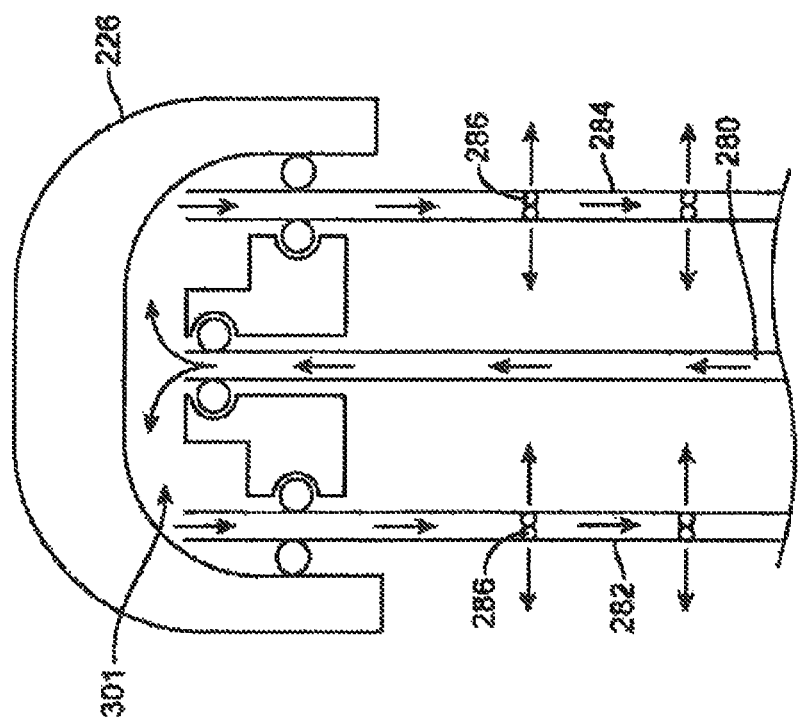
FIG. 39 shows a cross-sectional side view of another variation of the cooling probe assembly where the main delivery line and side delivery lines are in fluid communication through a common chamber.

Another variation of the cooling probe assembly is illustrated in the detail cross-sectional side view of FIG. 39. In this variation, a single main delivery line 280 may pass through and into communication with distal tip 226. Rather than having the side delivery lines 282, 284 coupled directly to the main delivery line 280, each respective line may be coupled to a common chamber 301 defined within the distal tip 226. Such an assembly may be used with alternative variations of the exhaust lumen 303 as shown in one example in the cross-sectional end view of FIG. 40A. In this example, the exhaust lumen 303 may be formed to have an indented cross-sectional area to accommodate the side delivery lines 282, 284. Alternatively, the exhaust lumen 303 may be shaped to have an elliptical cross-sectional area instead, as shown in FIG. 40B.

Figure 42:
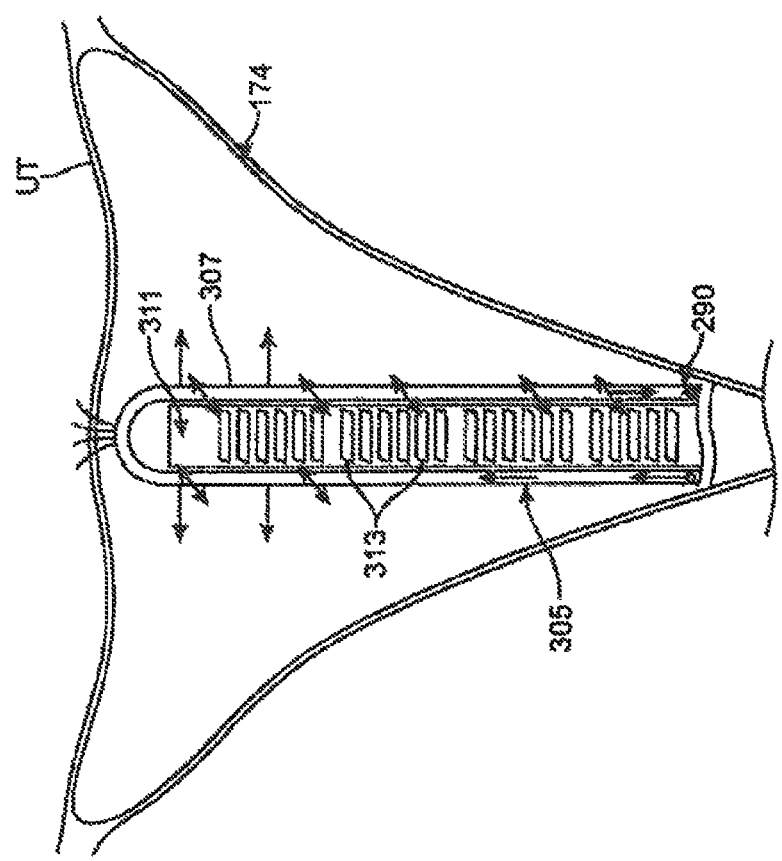
FIG. 42 shows a cross-sectional side view of a cooling probe assembly inserted within a balloon within the uterus.
Figure 41:
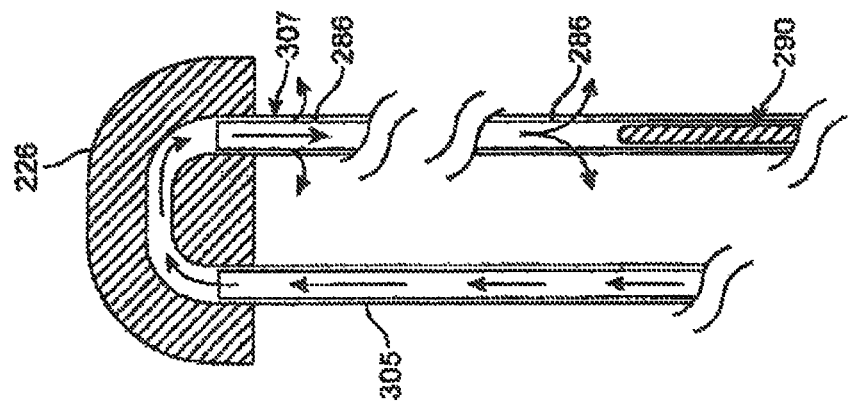
FIG. 41 shows a cross-sectional side view of another variation of a cooling probe assembly having a single introduction line and a single delivery line.

In yet another alternative, the cooling lumens may be formed to have a single introduction or infusion line 305 and a single delivery line 307 where the delivery line 307 may be in fluid communication directly with the introduction or infusion line 305 through the distal tip 226, as shown in the cross-sectional side view of FIG. 41. The infusion line 305 and delivery line 307 may be formed as separate lines or they may formed as a single continuous line where the infusion line 305 enters distal tip 226 and is curved to redirect the ablative fluid proximally through the delivery line 307. In this variation, as in the previous variations, a translatable mandrel 290 may be slidably positioned within the delivery line 307 or optionally along an outer surface of the delivery line 307 to selectively obstruct the openings 286 defined along the line 307. In other variations, one or more openings may also be optionally aligned along the infusion line 305 in addition to the openings 286 along delivery line 307. Moreover, the mandrel 290 may be actuated to slide (either at the same or different rate) along with the retraction of the sheath. FIG. 42 illustrates an example where the cooling probe assembly may be introduced into the interior of balloon 174 when deployed within the uterus UT. Alternatively, the balloon 174 may be attached directly along an outer surface of the cooling probe assembly itself. The expanded length of balloon 174 may be fixed along the outer surface of the cooling probe assembly proximal to the distal tip or it may be optionally adjustable via the positioning of the outer sheath. As shown, the introduction line 305 may introduce the cryoablative fluid along the cooling probe assembly where it may then be flowed proximally along the delivery line 307 for introduction into the interior of the balloon 174. As the cryoablative fluid is introduced, a slotted tube 311 having one or more directional slots 313 may be used to optionally direct the flow of the cryoablative fluid into the balloon interior.

Figure 43A:
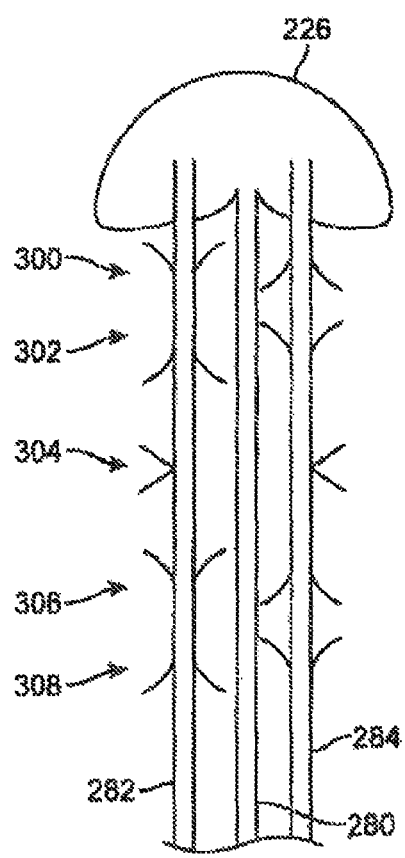
FIGS. 43A and 43B show side views of various examples of side delivery lines having the openings aligned in different directions.
Figure 43B:
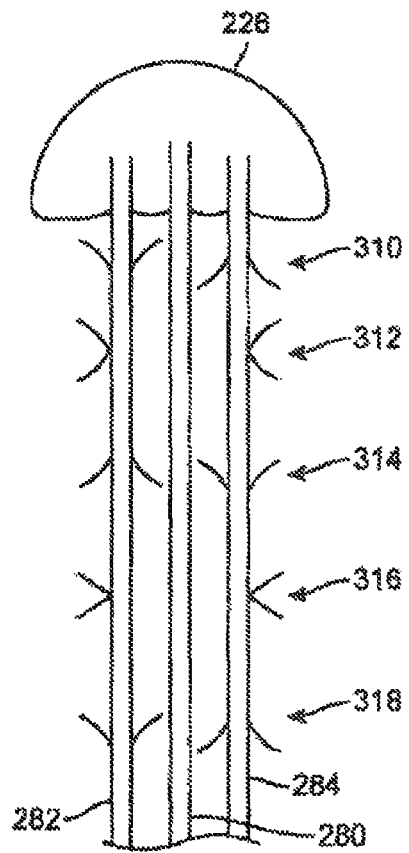

FIGS. 43A and 43B illustrate additional variations for selectively controlling the configuration of the hole directions along the side delivery lines to optionally control appropriate ablation depths and tapering, as needed or desired. In the variation of FIG. 43A, the adjacent side delivery lines 282, 284 from the distal tip 226 may be configured such that openings 300 are configured in an up/down configuration, openings 302 are configured in an down/up configuration, openings 304 are configured in an left/right configuration, openings 306 are configured in an up/down configuration, and openings 308 are configured in an down/up configuration. The hole directions of up/down/left/right are relative to the figures shown and are presented for illustrative purposes.

Likewise, the variation shown in FIG. 43B illustrates how the adjacent side delivery lines 282, 284 may be configured such that openings 310 are configured in an up/down configuration, openings 312 are configured in an left/right configuration, openings 314 are configured in an down/up configuration, openings 316 are configured in an left/right configuration, and openings 318 are configured in an up/down configuration. These variations are illustrated as exemplary variations and other variations of hole directions may be accomplished as desired.

Figure 44:
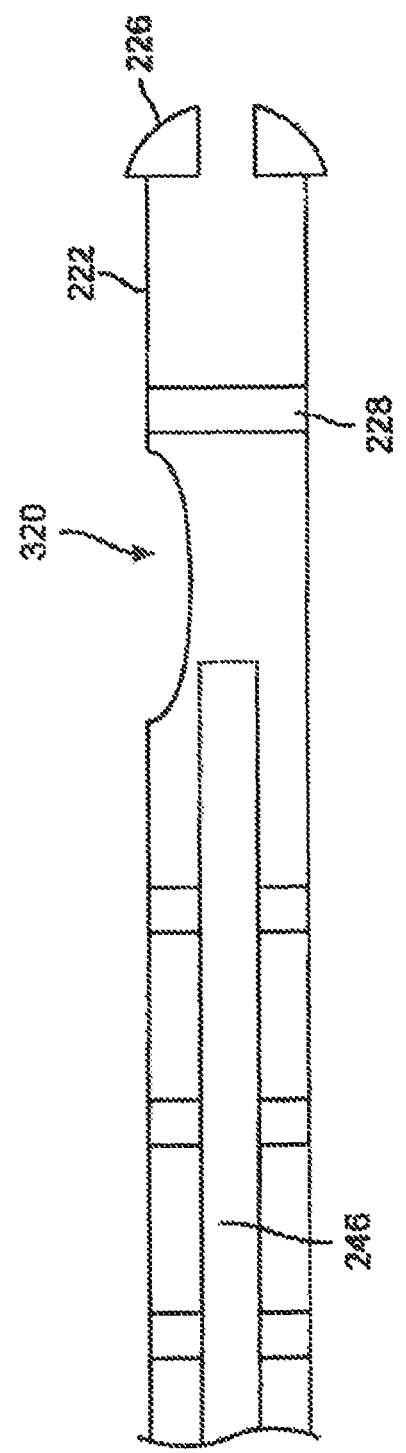
FIG. 44 shows a side view of a cooling probe variation having a skived window for facilitating visualization.

Aside from the positioning of the fluid openings, the catheter body 222 itself may optionally incorporate a skived viewing window 320, as shown in the side view of FIG. 44, to facilitate visualization of the surrounding balloon 174 and tissue by the hysteroscope 246 which may be advanced into proximity to the window 320 or entirely through as desired.

Figure 45:
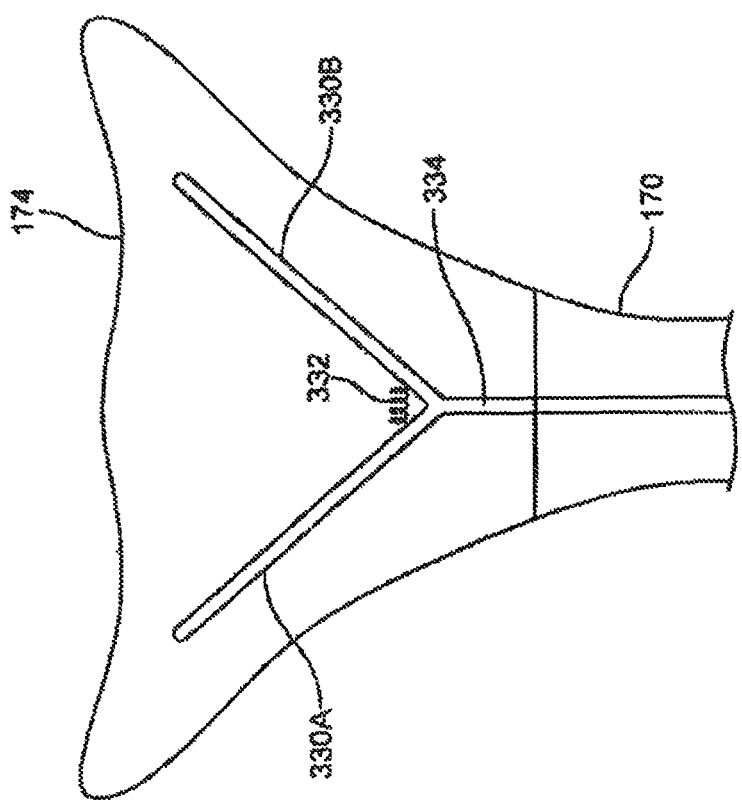
FIG. 45 shows a side view of an example of a balloon having one or more supporting arms extendable within the balloon.

As previously described, the balloon 174 may be expanded within the uterus UT and particularly into the uterine cornu UC by an initial burst of gas or liquid. Other mechanisms may also be used to facilitate the balloon expansion. One variation is shown in FIG. 45 which illustrates a balloon 174 having one or more supporting arms 330A, 330B extending from a support 334 which may be deployed within the balloon 174. The supporting arms 330A, 330B may be variously configured although they are shown in this example in a Y-configuration. Each of the distal ends of the arms may extend from a linear configuration into the expanded Y-configuration, e.g., via a biasing mechanism 332, which may bias the arms to extend once the sheath 212 is retracted. The distal ends of the arms 330A, 330B may extend into the tapered corners of the balloon 174 to facilitate the balloon 174 expansion into the uterine cornu UC and may also help to center the balloon 174 within the uterus UT.

Figure 46:
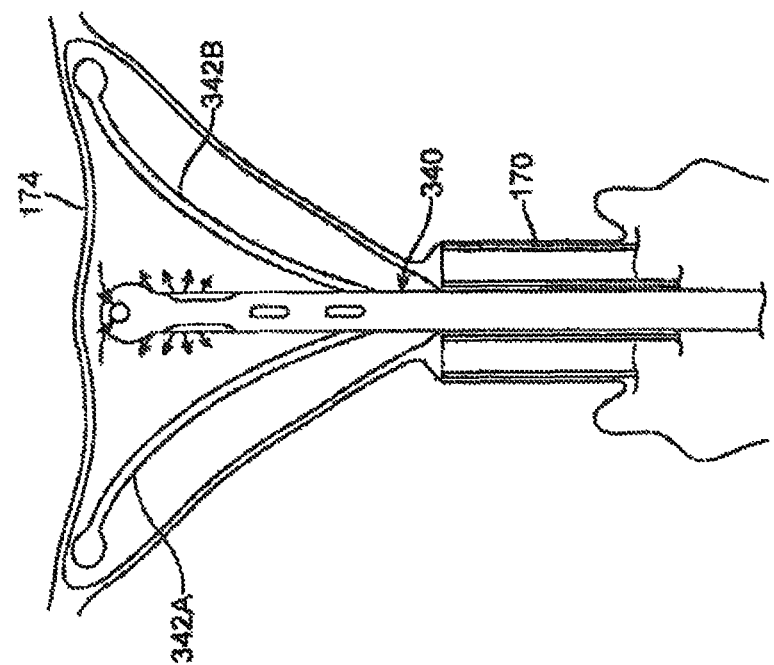
FIG. 46 shows a side view of another example of a balloon having one or more supporting arms attached to the cooling probe assembly.

FIG. 46 shows a partial cross-sectional side view of another variation of an expansion mechanism contained within the balloon 174 where one or more supporting arms 342A, 342B may be mechanically actuated to extend, e.g., via a biasing mechanism, push/pull wires, etc. Moreover, the arms 342A, 342B may be integrated into the design of the cooling probe 340 as an integrated assembly.

Figure 47:
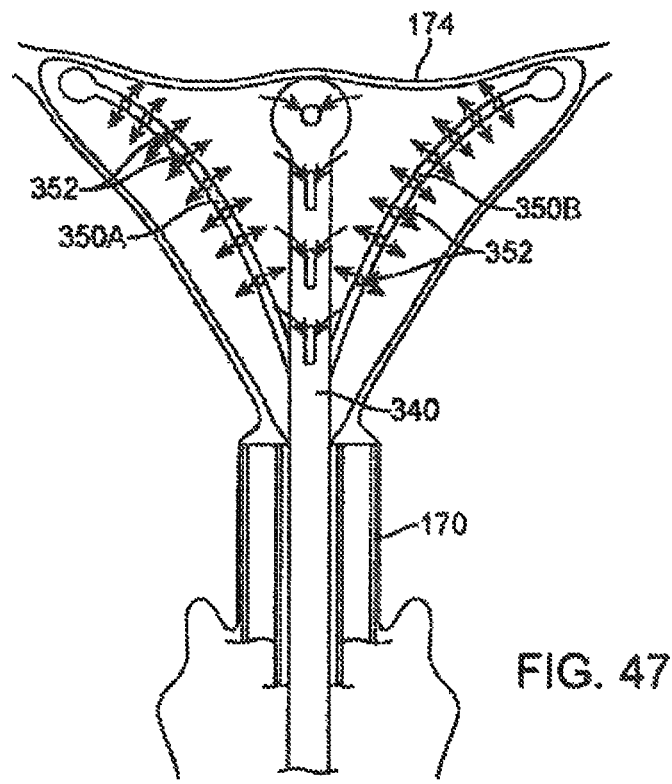
FIG. 47 shows a side view of another example of a balloon having one or more supporting arms also defining one or more openings for delivering the cryoablative fluid.

FIG. 47 shows a partial cross-sectional side view of another variation where the supporting arms 350A, 350B may also integrate one or more openings 352 for the infusion of the cryoablative fluid. In this example the arms 350A, 350B may be integrated with the cooling probe 340 or separated. In either case, the inclusion of the openings 352 may facilitate the distribution of the fluid into the balloon 174 interior.

Figure 48:
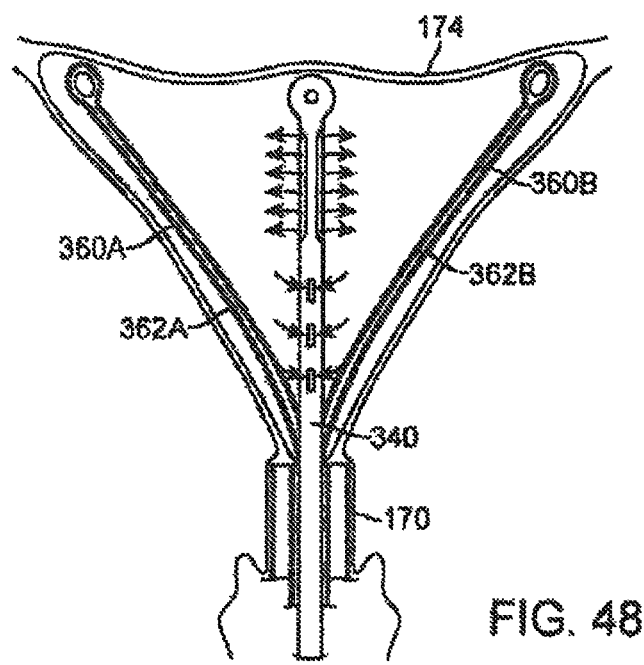
FIG. 48 shows a side view of yet another example of a balloon having the one or more supporting arms positioned within elongate channels along the interior of the balloon.

FIG. 48 shows yet another variation where the supporting arms 360A, 360B may be incorporated into elongate channels or pockets 362A, 362B defined along the balloon 174 itself. In this and other variations shown, the supporting arm members may optionally integrate the one or more openings for cryoablative fluid delivery and may also be integrated into elongate channels as practicable.

Figure 49A:
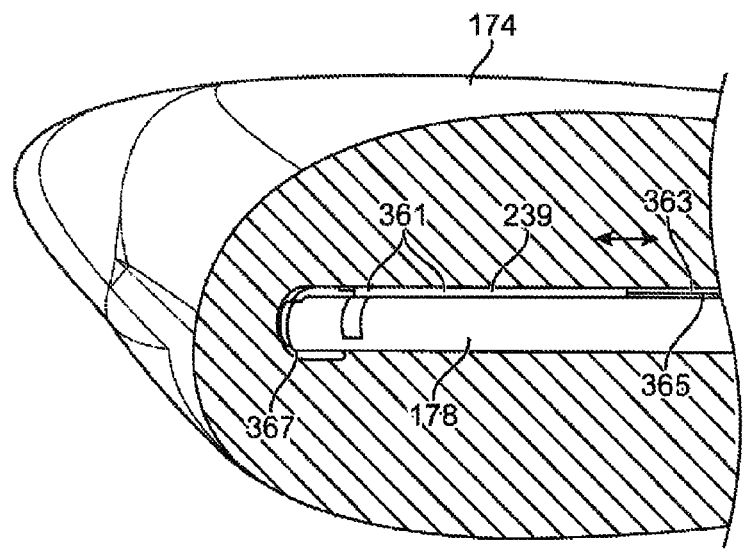
FIGS. 49A and 49B show cross-sectional side views of yet another variation of a cooling probe which utilizes a single infusion line in combination with a translatable delivery line.
Figure 49B:
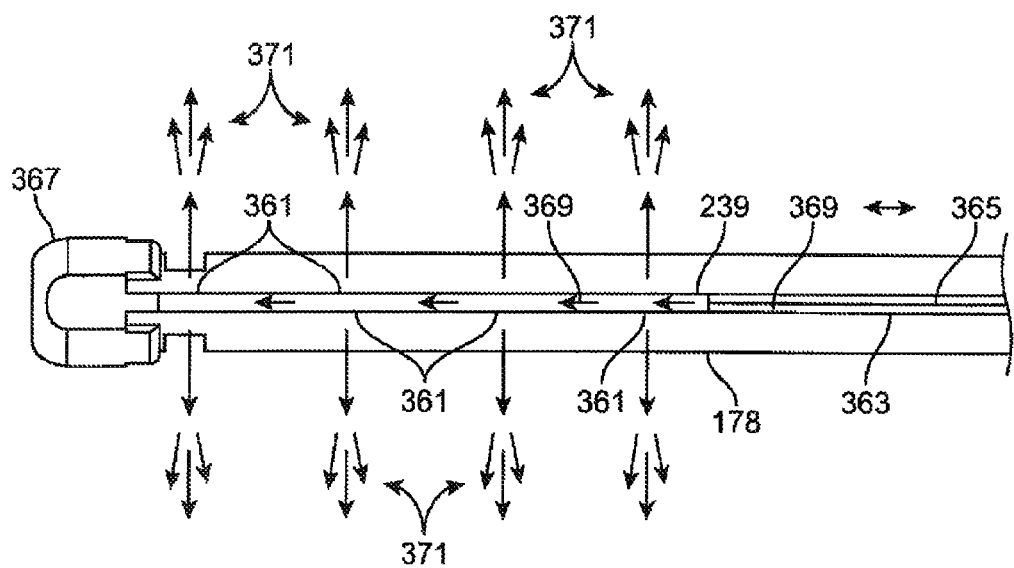

FIGS. 49A and 49B show cross-sectional side views of yet another variation of a cooling probe which utilizes a single infusion line in combination with a translatable delivery line. To accommodate various sizes and shapes of uterine cavities, the cooling probe may have a sliding adjustment that may be set, e.g., according to the measured length of the patient's uterine cavity. The adjustment may move along the sheath along the exhaust tube as well as the delivery line within the infusion line. The sheath may constrain the liner 174 and also control its deployment within the cavity.

In this variation, an infusion line 239 (as described above) may pass from the handle assembly and along or within the sheath and into the interior of liner 174. The infusion line 239 may be aligned along the probe 178 such that the infusion line 239 is parallel with a longitudinal axis of the probe 178 and extends towards the distal tip 367 of the probe 178. Moreover, the infusion line 239 may be positioned along the probe 178 such that the line 239 remains exposed to the corners of the liner 174 which extend towards the cornua. With the infusion line 239 positioned accordingly, the length of the line 239 within the liner 174 may have multiple openings formed along its length which act as delivery ports for the infused cryogenic fluid or gas. A separate translating delivery line 365, e.g., formed of a Nitinol tube defining an infusion lumen therethrough, may be slidably positioned through the length of the infusion line 239 such that the delivery line 365 may be moved (as indicated by the arrows in FIG. 49A) relative to the infusion line 239 which remains stationary relative to the probe 178.

The openings along the length of the infusion line 239 may be positioned such that the openings are exposed to the sides of the interior of the liner 174, e.g., cross-drilled. As the cryogenic fluid or gas is introduced through the delivery line 365, the infused cryogenic fluid or gas 369 may pass through the infusion line 239 and then out through the openings defined along the infusion line 239. By adjusting the translational position of the delivery line 365, the delivery line 365 may also cover a selected number of the openings resulting in a number of open delivery ports 361 as well as closed delivery ports 363 which are obstructed by the delivery line 365 position relative to the infusion line 239, as shown in the top view of FIG. 49B.

By translating the delivery line 365 accordingly, the number of open delivery ports 361 and closed delivery ports 363 may be adjusted depending on the desired treatment length and further ensures that only desired regions of the uterine tissue are exposed to the infused cryogenic fluid or gas 369. Once the number of open delivery ports 361 has been suitably selected, the infused cryogenic fluid or gas 369 may bypass the closed delivery ports 363 obstructed by the delivery line 365 and the fluid or gas may then be forced out through the open delivery ports 361 in a transverse direction as indicated by the infusion spray direction 371. The terminal end of the infusion line 239 may be obstructed to prevent the distal release of the infused fluid or gas 369 from its distal end. Although in other variations, the terminal end of the infusion line 239 may be left unobstructed and opened.

Figure 50A:
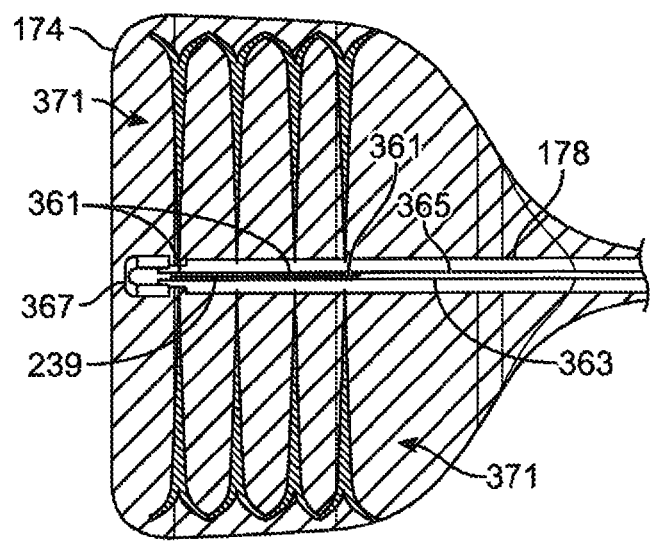
FIGS. 50A and 50B show top and perspective views of the expanded liner with four pairs of the open delivery ports exposed in apposed direction.
Figure 50B:
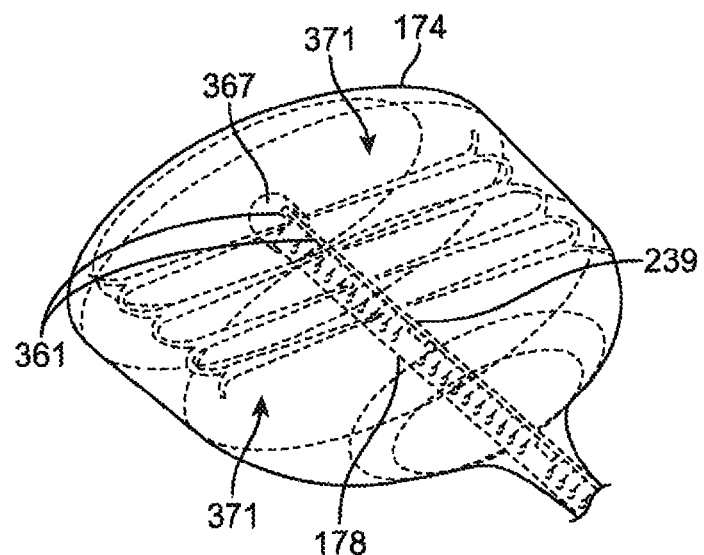

FIGS. 50A and 50B show top and perspective views of the expanded liner 174 with four pairs of the open delivery ports 361 exposed in apposed direction. Because the infused fluid or gas 369 may be injected into the liner 174, e.g., as a liquid, under relatively high pressure, the injected cryogenic liquid may be sprayed through the open delivery ports 361 in a transverse or perpendicular direction relative to the cooling probe 178. The laterally infused cryogenic fluid 371 may spray against the interior of the liner 174 (which is contacted against the surrounding tissue surface) such that the cryogenic liquid 371 coats the interior walls of the liner 174 due to turbulent flow causing heavy mixing. As the cryogenic liquid 371 coats the liner surface, the sprayed liquid 371 may absorb heat from the tissue walls causing rapid cooling of the tissue while also evaporating the liquid cryogen to a gas form that flows out through the cooling probe 178. This rapid cooling and evaporation of the cryogenic liquid 371 facilitates the creation of a fast and deep ablation over the tissue. During treatment, the temperature within the cavity typically drops, e.g., $-89°$ C., within 6-7 seconds after the procedure has started. While the interior walls of the liner 174 are first coated with the cryogenic liquid 371, the cryogenic liquid 371 may no longer change phase as the procedure progresses.

Figure 50C:
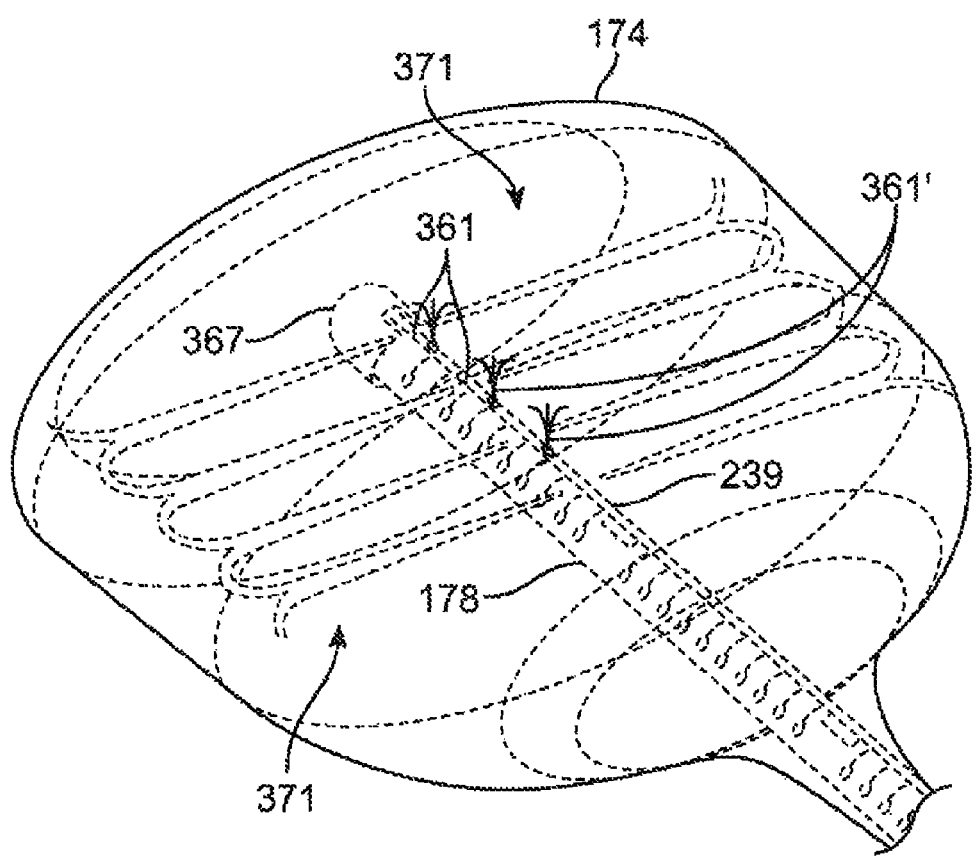
FIG. 50C shows a perspective view of an expanded liner with additional open delivery ports exposed along an anterior portion of the liner.

While four pairs of the open delivery ports 361 are shown, the number of exposed openings may be adjusted to fewer than four pairs or more than four pairs depending on the positioning of the delivery line 365 and also the number of openings defined along the infusion line 239 as well as the spacing between the openings. Moreover, the positioning of the openings may also be adjusted such that the sprayed liquid 371 may spray in alternative directions rather than laterally as shown. Additionally and/or alternatively, additional openings may be defined along other regions of the infusion line 239. For instance, one or more openings 361', e.g., one to three holes or more, may be added along the length of the infusion line 239 such that the openings directly face the portion of the liner 174 placed against the anterior portion of the contacted tissue, as shown in the perspective view of FIG. 50C.

Figure 51A:
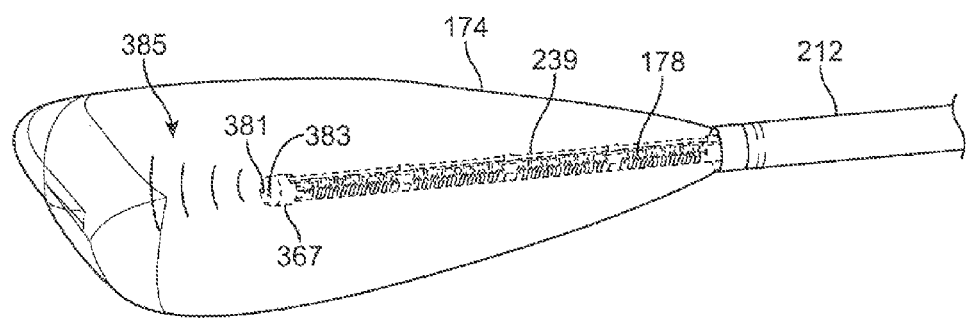
FIG. 51A shows one variation of a probe incorporating a transmitter to facilitate probe positioning within the liner.
Figure 51B:
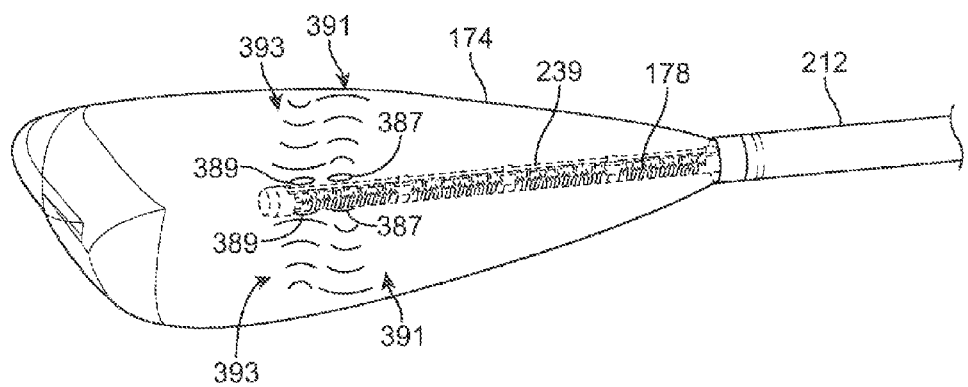
FIG. 51B shows another variation of a probe incorporating one or more transmitters to monitor tissue cavity expansion.

Prior to or during treatment, the positioning of the cooling probe 178 within the interior of the liner 174 and the uterus may be determined through various mechanisms. Visualization may be optionally provided by use of hysteroscopy, endoscopy, fluoroscopy, or ultrasound or other more invasive modalities. However, other variations for determining the cooling probe 178 position may include use of a transmitter 381, e.g., light, ultrasound, etc., which may be placed on the distal tip 367 of the probe 178, as shown in the perspective view of FIG. 51A.

In the event that a light 381 such as an LED light is placed upon the distal tip 367, the user may simply visually monitor the patient for the transmission of the light through the tissue and skin of the patient to determine whether the tip 367 is properly positioned within the uterus or the peritoneal cavity depending on where the light is emitted directly through the body. In another variation, a sensor or receiver 383 may be placed upon the distal tip 367 adjacent to the transmitter 381. As the transmitter 381 emits a light or ultrasound signal 385, the signal 385 may reflect off the surrounding tissue surface (and through the liner 174). Depending on the wavelength of the reflected signals collected by the receiver 383, a processor or microcontroller can be used to determine the general color of the tissue in front of the end of the probe as the inner wall of the uterus, intestine, and bladder should all have distinct color signatures.

In yet another variation, one or more transmitters 387, e.g., light, ultrasound, etc., may be placed along the probe 178 along opposite surfaces to facilitate determining the amount of cavity expansion, e.g., during initial pre-treatment liner expansion. The transmitted signals 391 may be emitted as discrete pulses of light which are returned as reflected signals 393 to corresponding sensors or receivers 389 which are adjacent to the transmitters 387. By measuring the time it takes for the reflected signals 393 to return to the sensors or receivers 389, the processor or microcontroller can determine the amount of cavity expansion which has occurred. The transmitters and/or sensors/receivers may be incorporated in any of the variations of the devices and methods described herein.

Once a cryoablation treatment procedure has been completed and the interior of the liner is vented, the device may be removed from the patient body. To facilitate the removal of the liner 174 from the treated tissue surface, negative pressure may be applied to the interior of the liner 174 to quickly remove the discharged cryogenic fluid or gas as well as to help pull the liner 174 away from the tissue surface. Removing the liner 174 from the tissue surface may be relatively easy when the removal force is normal to the tissue surface. Hence, use of negative pressure or a suction force at the end of an ablation procedure may facilitate the removal or peeling of the liner 174 from the uterine tissue surface.

The pump which is used to introduce air initially into the liner interior may be used to also remove the discharged cryogenic fluid or gas particularly if the pump (such as pump 225 shown above in FIG. 21G) is configured as a reversible pump, e.g., connected to H-bridge circuitry which may allow for the polarity of the voltage on the pump to be reversed which will allow for the reversal of the flow direction of the pump. Another variation may utilize a separate pump which is configured to draw a suction force upon the liner interior separate from the pump used to introduce air into the liner.

Figure 52A:
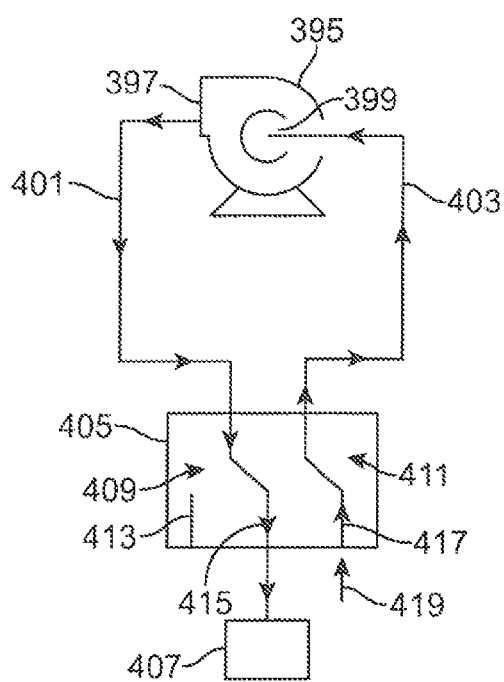
FIGS. 52A and 52B show a schematic illustration of a system utilizing a 5-port, 2 position, 4-way valve.

Yet another variation may utilize a non-reversible pump 395 which is fluidly coupled to a 5-port, 2 position, 4-way valve 405 which allows for the pressured pump output 397 to be connected to the exhaust/liner 407 through output line 401 and through liner line 415 within valve 405. A first switch 409 within the valve 405 may be switched to fluidly couple the output line 401 with the liner line 415. The negative pressure pump input 399 may be opened to the ambient air 419 through ambient line 417 within the valve 405 for initially expanding the liner 174, as shown in the schematic illustration of FIG. 52A. The ambient air 419 may be fluidly coupled to the input line 403 via second switch 411 within the valve 405.

Figure 52B:
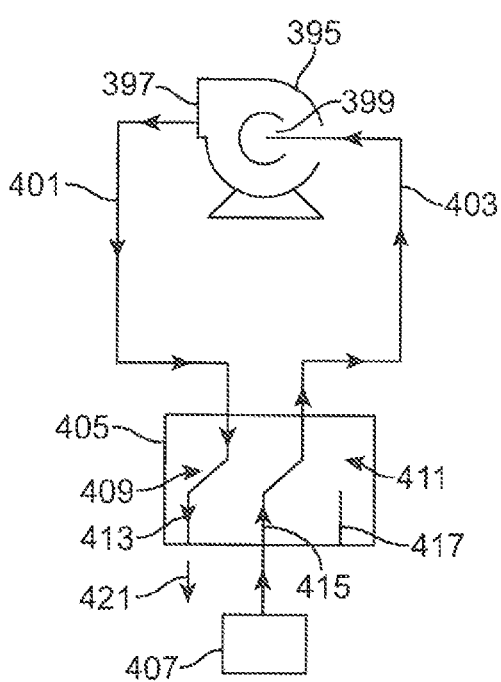

When the ablation procedure has been completed and the liner 407 to be vented and collapsed, the valve 405 may be switched such that first switch 409 fluidly couples output line 401 to ambient line 413 and second switch 411 switches to fluidly couple the liner 407 to liner line 415 and input line 403, as shown in the schematic illustration of FIG. 52B. The fluid and/or gas within the liner 407 may be drawn out by the negative pressure created within input line 403 which may then force the discharged fluid or gas through output line 401, through ambient line 413 within valve 405, and out as exhausted fluid or gas 421. Thus, a single directional pump 395 may be used for both inflation and deflation with the valve 405.

Figure 53A:
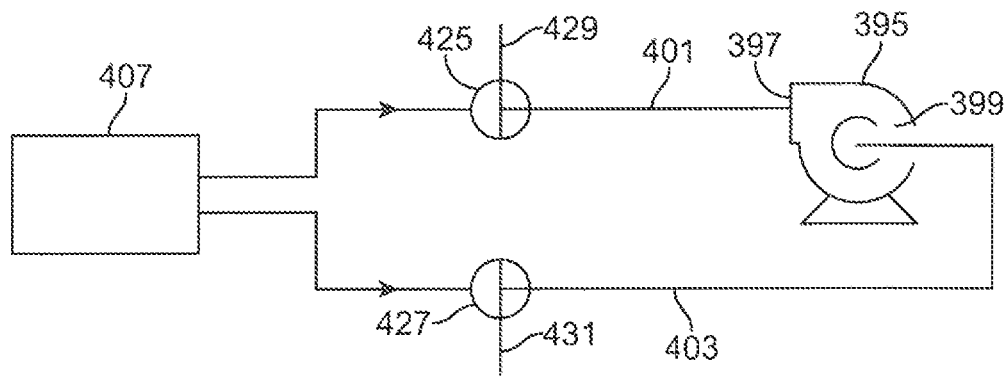
FIGS. 53A to 53C show a schematic illustration of a system utilizing a non-reversible pump for both inflation and deflation.

Yet another variation is shown in the schematic diagrams of FIGS. 53A *to* 53C which also illustrates the use of a non-reversible pump 395 for both inflation and deflation. In this variation, the pump output line 401 may incorporate a first 3-way valve 425 and the pump input line 403 may incorporate a second 3-way valve 427. The first and/or second valves 425, 427 may comprise, e.g., 3-way solenoid valves, which may remain unpowered with both valves 425, 427 connecting the pump 395 to the ambient environment through respective ambient lines 429, 431, as shown in FIG. 53A. The configuration shown may keep any fluid or gas within the liner 407 from being pumped or leaked to the environment.

Figure 53B:
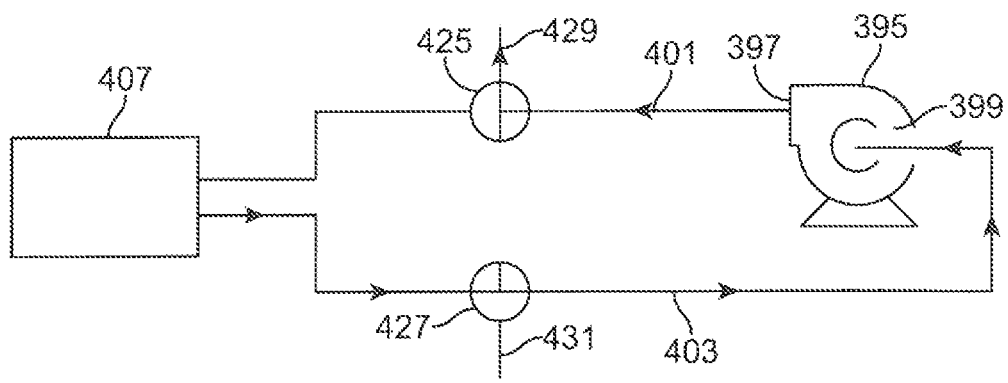

If the liner 407 is to be evacuated, the first valve 425 may be actuated or energized such that the pump output line 401 is fluidly connected to the ambient line 429 and the second valve 427 may be actuated or energized to fluidly couple the liner 407 with the pump input line 403, as shown in FIG. 53B. With the pump 395 actuated, the input line 403 may draw a negative pressure to suction out the fluid or gas within liner 407 while the pump output pushes air or the suctioned fluid or gas out through ambient line 429.

Figure 53C:
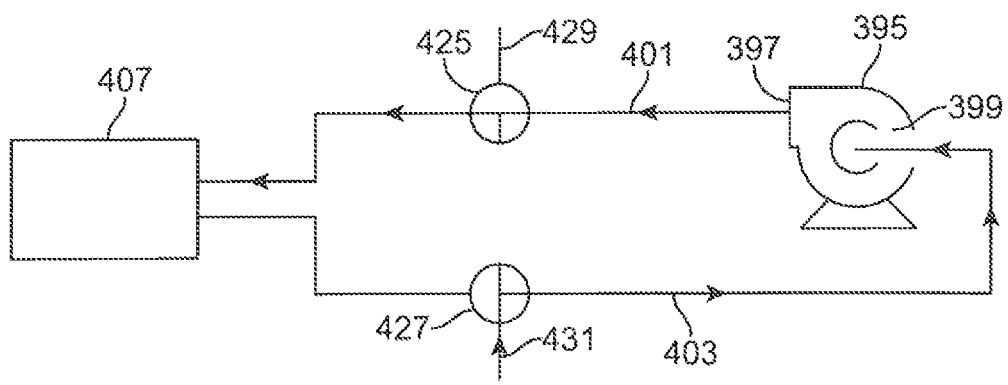

If the liner is to be initially expanded and/or the cryogenic fluid or gas is to be to introduced into the liner 407 for treatment, the first valve 425 may be actuated or energized to fluidly couple the output line 401 from the pump 395 to the liner 407 while the second valve 427 may be actuated or energized to fluidly couple the pump input line 403 with the ambient line 431, as shown in FIG. 53C. Moreover, the actuation of the first and second valves 425, 427 may be coordinated such that simultaneous or individual actuation of the valves is controlled by a processor. Alternatively, one or both valves 425, 427 may be controlled manually by the user. As above, this valve configuration may be used with any of the different liner, probe, handle assembly, or treatment methods described herein.

Figure 54A:
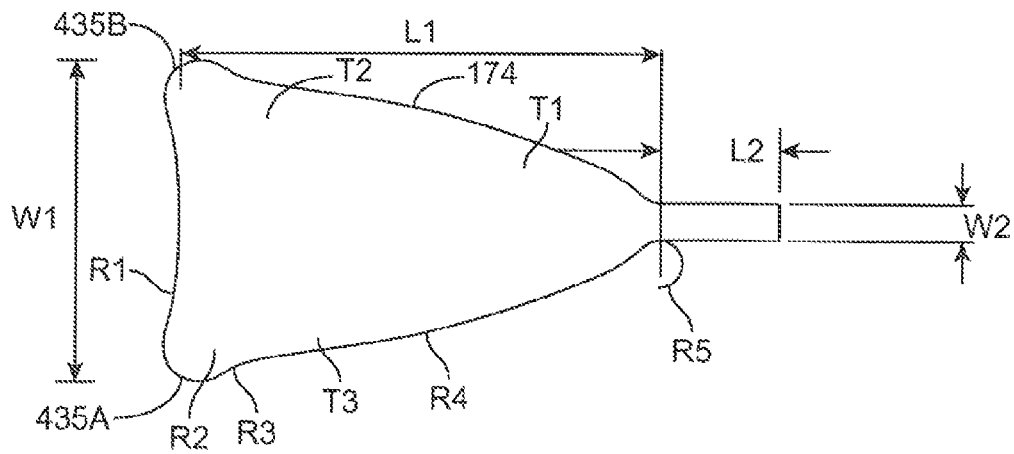
FIGS. 54A and 54B show top and perspective views of a liner illustrating its curved features when flattened and expanded and then deployed in a consistent manner.
Figure 54B:
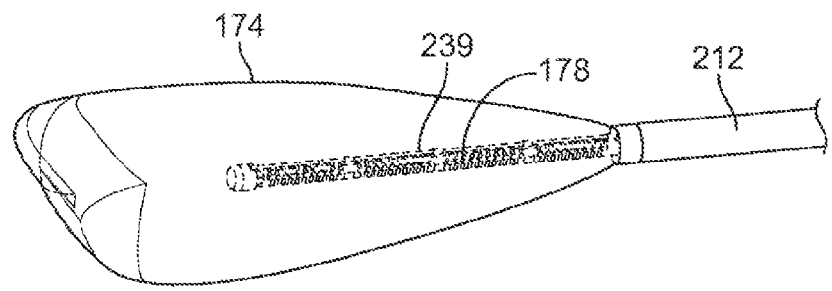

Turning now to the liner itself, the liner may be formed to have, e.g., a nominal 0.0012 in. thick flexible membrane such as pellethane. The liner 174 may be optionally formed as a composite from one or more sheets of material, e.g., two sheets of membrane which are RF welded. When laid out in a flattened shape, the liner 174 may shaped in a manner, as shown in the top view of FIG. 54A, which allows the liner 174 to inflate or expand into a contoured shape which conforms closely to a uterine cavity, as shown in the perspective view of FIG. 54B. FIG. 54A shows one example of a flattened liner 174 which gently tapers from the opening to a curved shape forming a first curved portion 435A and a second curved portion 435B opposite to the first curved portion 435A. The liner 174 may hence taper gently from a first width W1, e.g., about 2.4 in., down to a second width W2, e.g., about 0.3 in., over a length L1 of, e.g., about 3.5 in. The neck may form a length L2, e.g., about 0.9 in.

The region between each of the first and second curved portions 435A, 435B may also be curved to have a radius R1 of, e.g., about 3.5 in., while curved portions 435A, 435B may also be curved to each have a radius R2 of, e.g., about 0.3 in. The portion of the liner proximal to the portions 435A, 435B may also have a radius R3, e.g., about 1.1 in., and an oppositely radiused portion of radius R4, e.g., about 8.0 in. The region between the liner 174 and neck may further have a radius R5, e.g., about 0.2 in.

The liner 174 itself may be formed to have a uniform thickness over the entire liner. Alternatively, different portions of the liner 174 may also be formed to have differing thicknesses depending upon the desired degree of treatment along differing portions of the liner 174. For instance, the liner 174 may have varying regions of thickness T1, T2, T3 along proximal portions of the liner relative to distal portions of the liner.

Figure 54C:
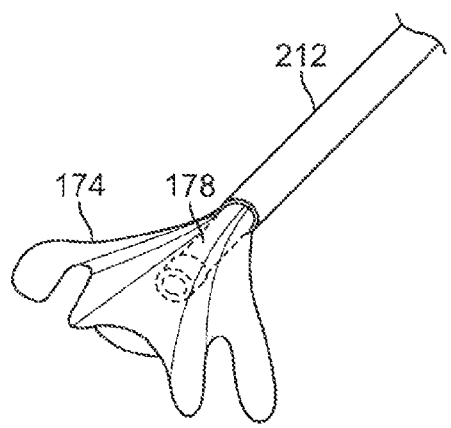
FIG. 54C shows a perspective view of a liner which may be pleated to fold and collapse in a consistent manner.

Moreover, to facilitate smooth retraction of the sheath and consistent deployment, the liner 174 may be pleated to fold and collapse in a consistent manner, as shown in the perspective view of FIG. 54C. The liner 174 may be pleated, e.g., using a fixture during manufacturing.

Figure 55A:
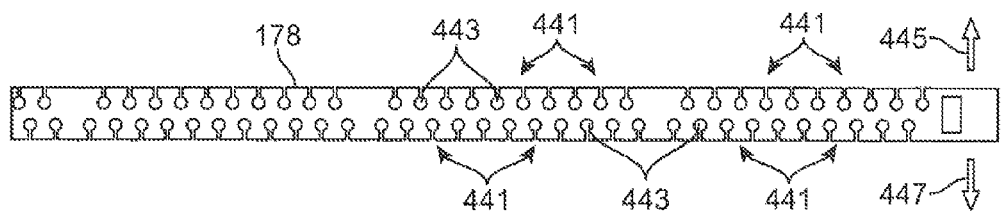
FIGS. 55A and 55B show side and top views of a probe which is configured to flex in the anterior and posterior directions.
Figure 55B:
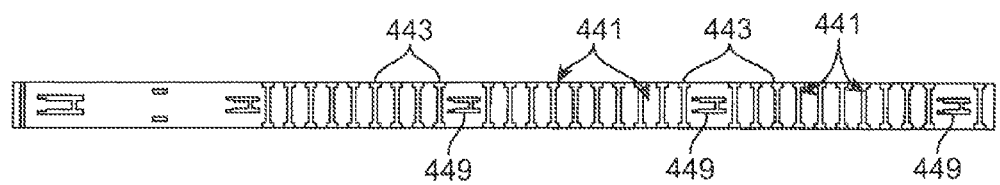

As previously described, the probe 178 may be advanced into and through the patient's cervix CV and into the uterus UT while conforming to any anatomical features by bending along an anterior direction of flexion 445 or posterior direction of flexion 447 (e.g., up to 90 degrees or more) but may further allow the probe 178 to maintain some degree to rigidity and strength in the transverse plane. The probe 178 may accordingly have a plurality of cut patterns 441, e.g., laser-cut, along the anterior and posterior surfaces of the probe 178, as shown in the side and top views of FIGS. 55A and 55B. These cut patterns 441 may be cut partially through the probe 178 along opposing surfaces, e.g., in an alternating manner, and may further define portions of removed material 443 along the ends of each cut pattern 441. In addition to the cut patterns 441, one or more H-slots 449 may also be cut periodically along, e.g., the anterior surface of the probe 178 to allow for anchoring locations for the infusion line 239.

Figure 55C:
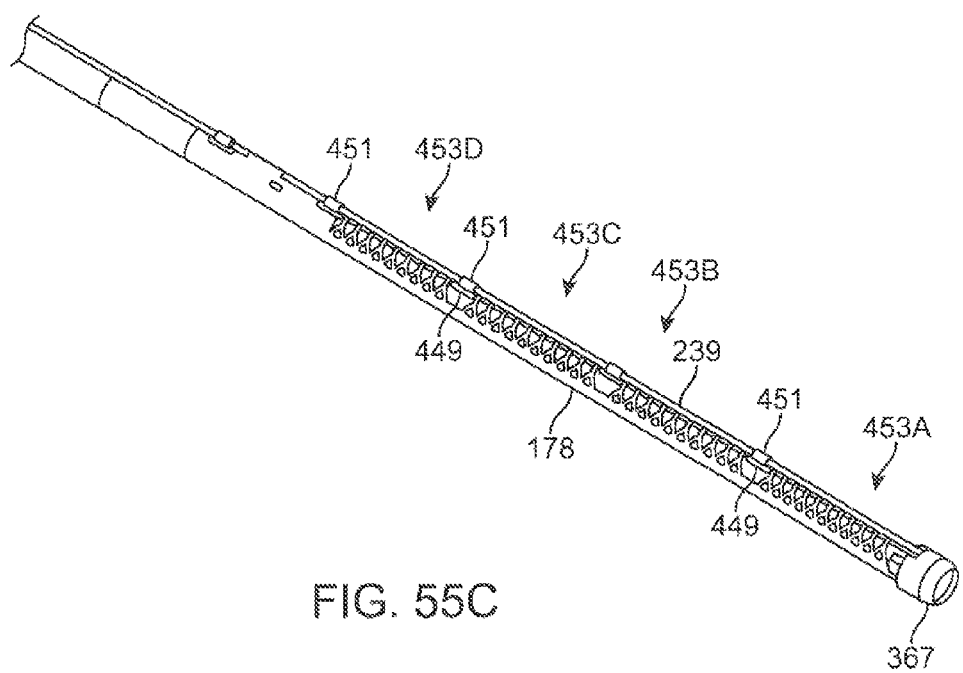
FIG. 55C shows a perspective view of a probe having multiple probe sections (e.g., four sections in this variation) separated by H-slots.

An example is illustrated in the perspective view of FIG. 55C which shows a probe 178 having multiple probe sections 453A, 453B, 453C, 453D (e.g., four sections in this variation) separated by H-slots 449. One or more anchors 451 (e.g., collars, clips, etc.) may couple the infusion line 239 to the probe 178 along its anterior surface via the anchors 451 secured to the H-slots 449, as shown.

Figure 56A:
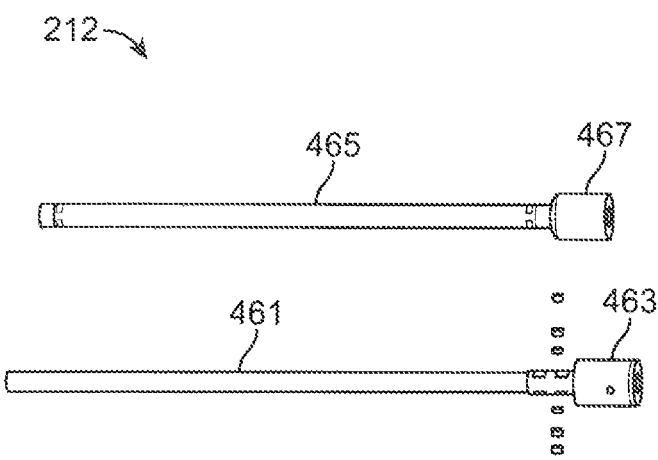
FIGS. 56A and 56B show perspective and detail cross-sectional views of a sheath assembly.

Aside from the liner or balloon itself and the use of balloons for obstructing the os, internal os, and/or external os, as described above, balloons or inflatable liners may also be used to insulate the cryogenic fluid during delivery into the balloon to protect the surrounding tissue structures which are not to be ablated, such as the cervix CV. One variation is illustrated in the perspective assembly view of FIG. 56A which shows a cervical protection assembly having an inner sheath 461 (e.g., PTFE or other polymer) which may be inserted within an outer sheath 465 (e.g., double walled stainless steel). The inner sheath 461 may have an inner sheath hub 463 at its proximal end which may securely contact an outer sheath hub 467 also located at its proximal end. With the inner sheath 461 inserted entirely within outer sheath 465, the inner sheath 461 may prevent the liner 174 from inflating into contact against the outer double walled sheath 465.

Figure 56B:
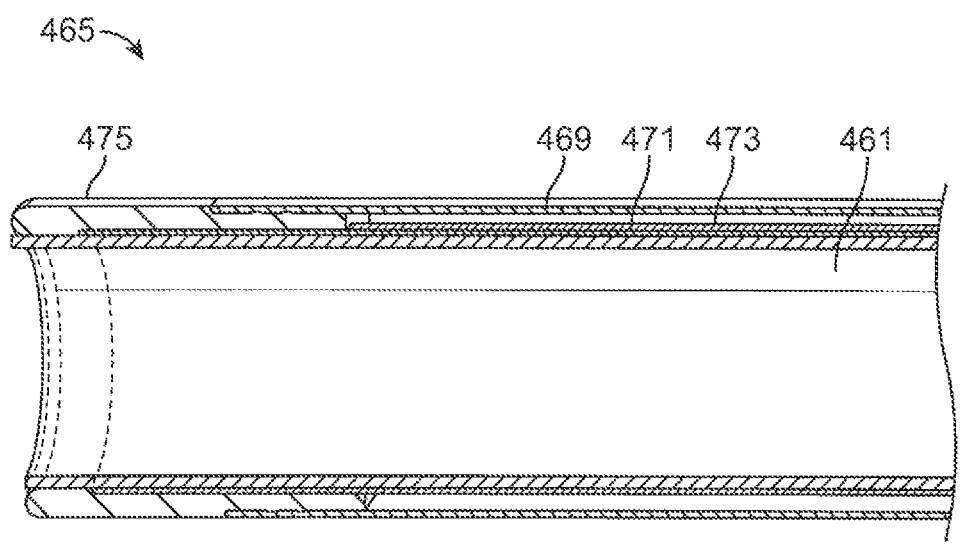

As shown in the cross-sectional perspective view of FIG. 56B, the double walled outer sheath 465 may have an inner tubular member 471 and a surrounding outer tubular member 469 (e.g., stainless steel, polymer, etc.) forming an insulating annular gap or spacing 473 (e.g., 0.0115 in. spacing). In the event that the tubular members 469, 471 are made of a polymer, the tubular members may be made with a wall thickness of, e.g. 0.00025 to 0.003. The distal end of the outer sheath 465 may have distal tip 475 to maintain the spacing between the tubular members of the outer sheath 465. With the annular gap or spacing 473 and the presence of the inner sheath 461, the sheath assembly may provide thermal insulation for the cervical region by insulating the surrounding tissue from the cryogenic fluid or gas passed through the infusion line 239 and from the cryogenic fluid or gas withdrawn through the inner sheath 461 from the liner 174.

While the annular gap or spacing 473 may have air within the spacing function as an insulator, the spacing may alternatively be evacuated of air to provide for a vacuum insulator. In another alternative, active flow of warmed or ambient temperature fluid (air or gas) may be included between the inner and outer tubular members 469, 471 or insulative materials may instead be placed within the gap or spacing (e.g., inflatable balloons, spiral wound balloons, cotton, wool, synthetic fibers, Neoprene, etc.). In yet another alternative, additional tubular members may be incorporated to create multiple annular gaps.

Figure 56C:
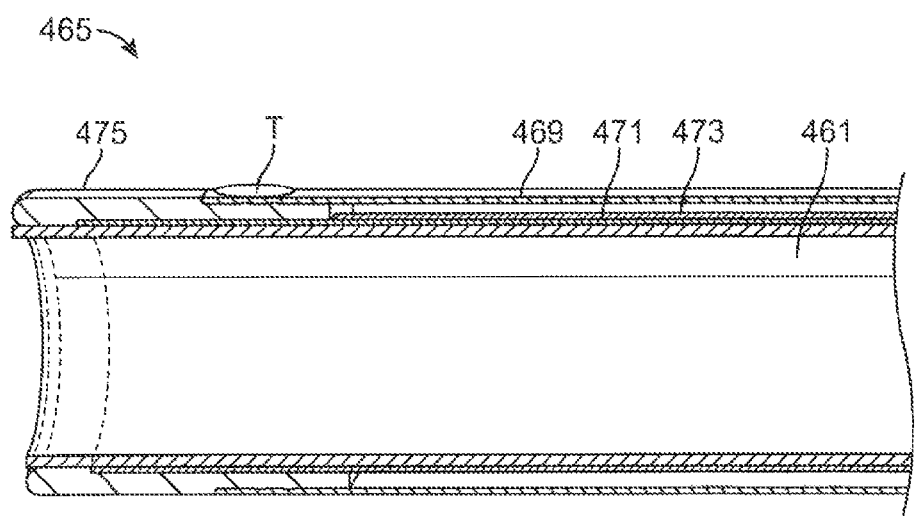
FIG. 56C shows a cross-sectional view of a sheath assembly incorporating a sensor, e.g., temperature sensor.

Additionally and/or optionally, the temperature of the sheath 212 may also be monitored so that the temperature may be provided in a feedback loop to a processor or microcontroller for ensuring the surrounding tissue (e.g., cervix) is maintained at a safe level. Accordingly, one or more temperature sensors T, e.g., thermocouples, may be placed along the sheath 212, as shown in FIG. 56C, and in communication with the processor or microcontroller. The processor or microcontroller may accordingly be programmed with a feedback loop which could start, pause, or stop the delivery of the cryogenic fluid or gas based upon the temperature (e.g. −89.5° C. for nitrous oxide) of the sheath 212.

Figure 57:
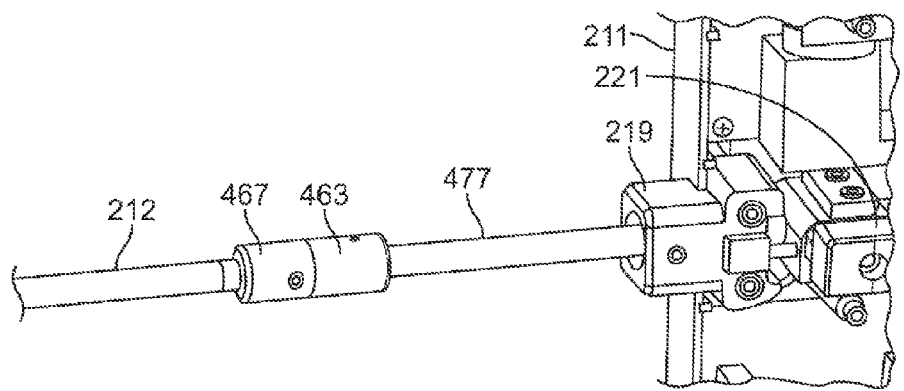
FIG. 57 shows one variation of a sheath bearing tube slidingly passing through a sheath bearing assembly and then attached to a slider base block assembly positioned within the handle assembly.

In actuating and controlling the translation of the sheath 212 and probe 178, the handle assembly 211 may further incorporate a sheath bearing tube 477 coupled to the sheath 212 assembly. FIG. 57 illustrates one variation where the sheath bearing tube 477 slidingly pass through a sheath bearing assembly 219 and then attached to a slider base block assembly 221 which is positioned within the handle assembly 211. The actuatable sheath control 223 may be attached to the slider base block assembly 221 for advancing and retracting the slider base block assembly 221 to control the positioning of the sheath 212 to ensure that the sheath 212 covers the cervical region during a treatment procedure.

Figure 58:
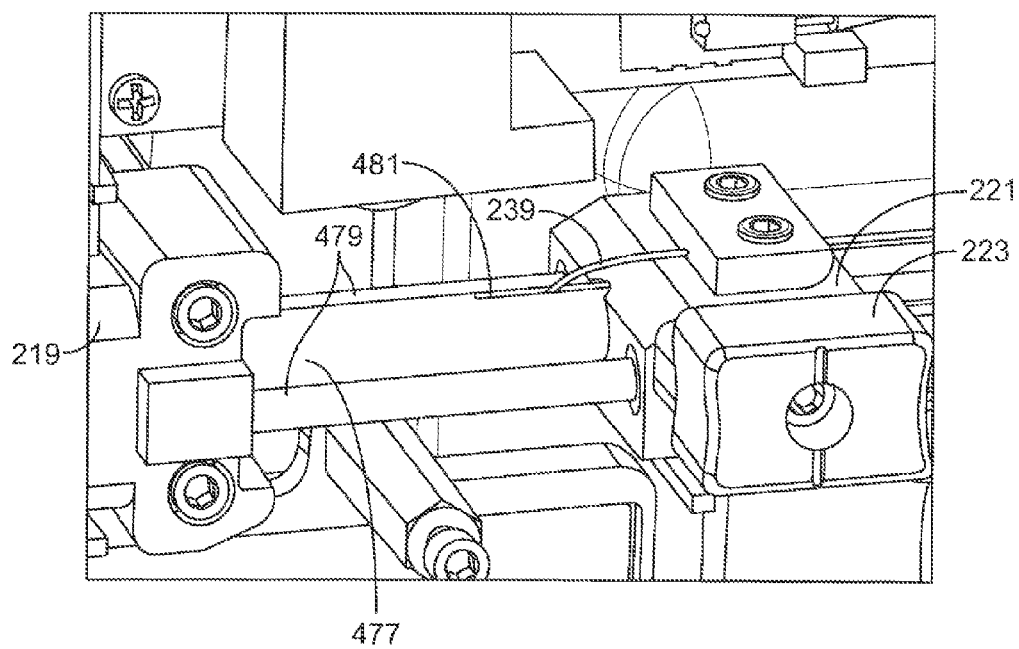
FIG. 58 shows a detail perspective view of the connection between the sheath bearing tube and slider base block assembly.

FIG. 58 shows a detail perspective view of the connection between the sheath bearing tube 477 and slider base block assembly 221. One or two linear rails 479 may be aligned adjacent to the sheath bearing tube 477 within handle 211 to serve as bearing surfaces for the slider base block assembly 221. Additionally, a receiving channel 481 may be defined along the anterior surface of the sheath bearing tube 477 to function as an access channel for the infusion line 239 into or along the sheath assembly. Accordingly, as the slider base block assembly 221 is translated linearly along the rails 479, the sheath bearing tube 477 and infusion line 239 may be advanced distally and/or proximally relative to the probe 178 to control the relative positioning of the sheath 212.

Figure 59A:
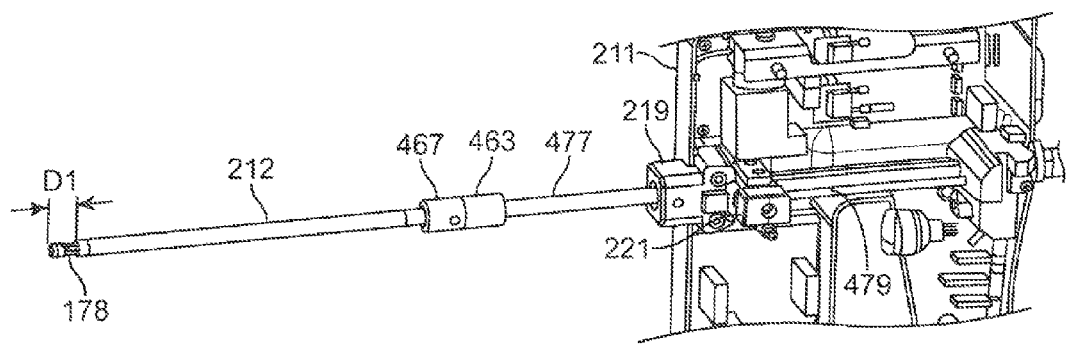
FIGS. 59A and 59B illustrate how the slider base block assembly may be advanced distally or proximally relative to the handle assembly to expose the probe length.
Figure 59B:
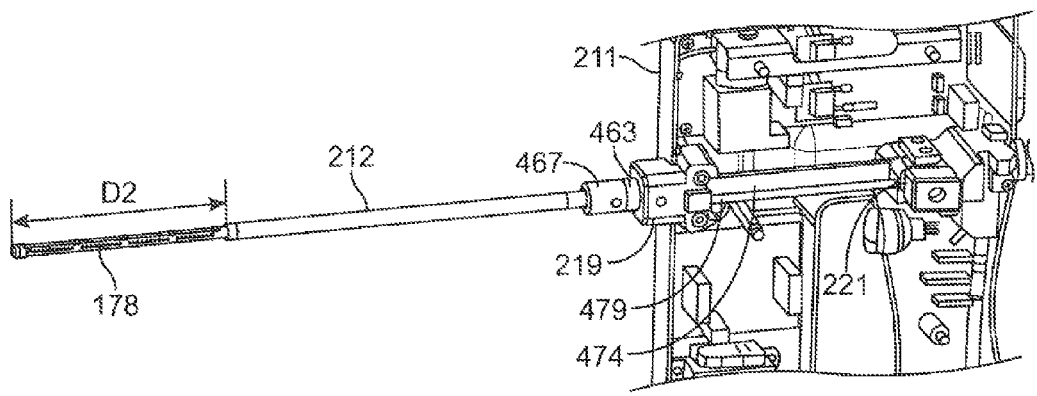

As illustrated in the perspective views of FIGS. 59A and 59B, when the slider base block assembly 221 is advanced distally relative to the handle assembly 211, the sheath 212 may be translated distally such that a nominal exposed length D1 of the probe 178 may be seen. (The liner 174 is not shown for clarity only.) As the slider base block assembly 221 is advanced proximally, the sheath 212 may be accordingly retracted to expose the probe 178 further, as indicated by the exposed length D2. The full travel of the sheath and slider base block assembly 221 may range anywhere from, e.g., 1 cm to 8 cm or more, as measured from the distal end of sheath 212 to the distal end of the tip of probe 178. The positioning of the slider 221 and sheath 212 may be maintained via any number of locking or positioning mechanisms to ensure that the ablation length is maintained during a treatment procedure. Hence, the locking of the slider 221 and sheath 212 may be accomplished by locking mechanisms, e.g., friction fitting, detention features such as notches along the length of the slider travel, grabbing mechanism such as a brake between the slider and handle, actuating features, etc.

Figure 60:
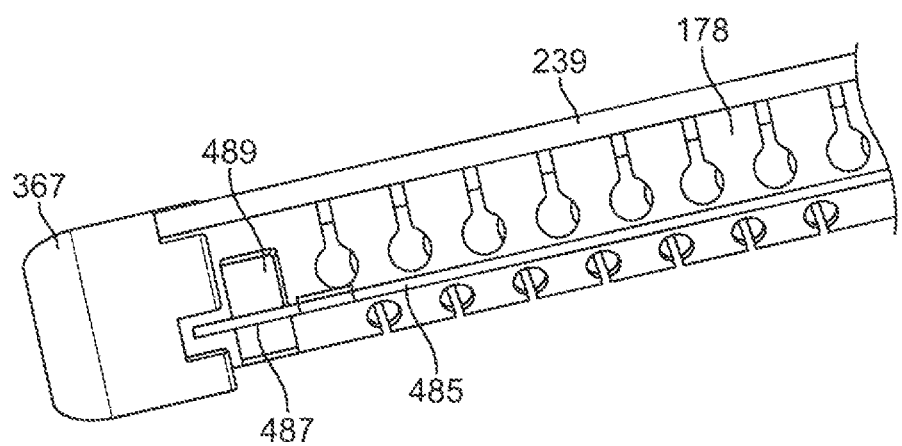
FIG. 60 shows a perspective view of one or more optional pressure sensing lines incorporated along the probe.

By measuring the pressure decay within the liner 174 during treatment, the rate at which the cryogenic liquid is being converted to a gaseous state may be determined since the lower the cavity pressure the less cryogenic fluid is being converted from liquid to gas. One or more optional pressure sensing lines 485 may be incorporated along the probe 178, as shown in the perspective view of FIG. 60. (A secondary line may be provided for redundant measurement of the pressure.) The pressure sensing line 485 may have a pressure sensor 487 positioned along a cutout window 489 defined along the probe 178 for monitoring the pressure internal to the liner 174 during treatment. The cutout window 489 may be provided to prevent the ends of the pressure lines 485 from contacting the interior of the liner 174. The pressure lines 485 may be routed along the full length of the sheath 212 and the proximal ends of the lines 485 may be attached to connectors which connect to the pressure sensors via short silicone tube sections.

Additionally, the pressure sensing lines 485 and sensors 487 may also be used as safety feature for the system. The lines 485 and sensors 487 can trigger the actuatable valve 237 which is fluidly coupled to the cryogenic line 235 (shown above in FIG. 21E) to close and stop the flow of the cryogenic fluid or gas in the event of pressures detected in the uterine cavity which are higher than expected.

Figure 61:
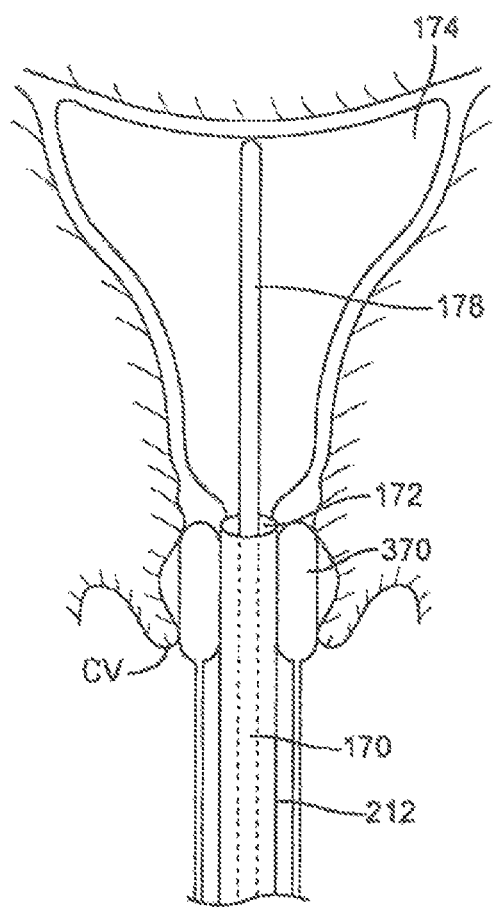
FIG. 61 shows a side view of an example of an inflatable liner or balloon located along the outside distal surface of the sheath.

FIG. 61 shows a partial cross-sectional of another variation where an inflatable balloon 370 may be located along the outside distal surface of sheath 212 for contacting against and directly insulating the cervix CV. The liner or balloon 370 may be filled with a gas or liquid such as air, water, carbon dioxide, etc. to act as an insulator to prevent contact between the delivered cryoablative fluid passing through the shaft 170 and the surrounding cervical tissue. The balloon 370 may be inflated prior to or during an ablation treatment and then deflated once the treatment has been completed to facilitate removal of the device. The size of the balloon 370 may be optionally varied, e.g., by the sheath placement location.

Figure 62:
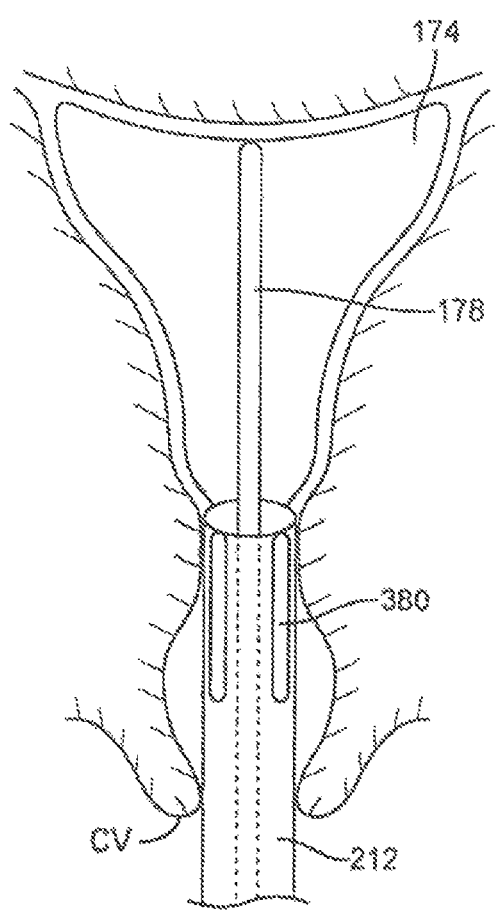
FIG. 62 shows a side view of another example of an inflatable liner or balloon located along the inside distal surface of sheath.
Figure 65:
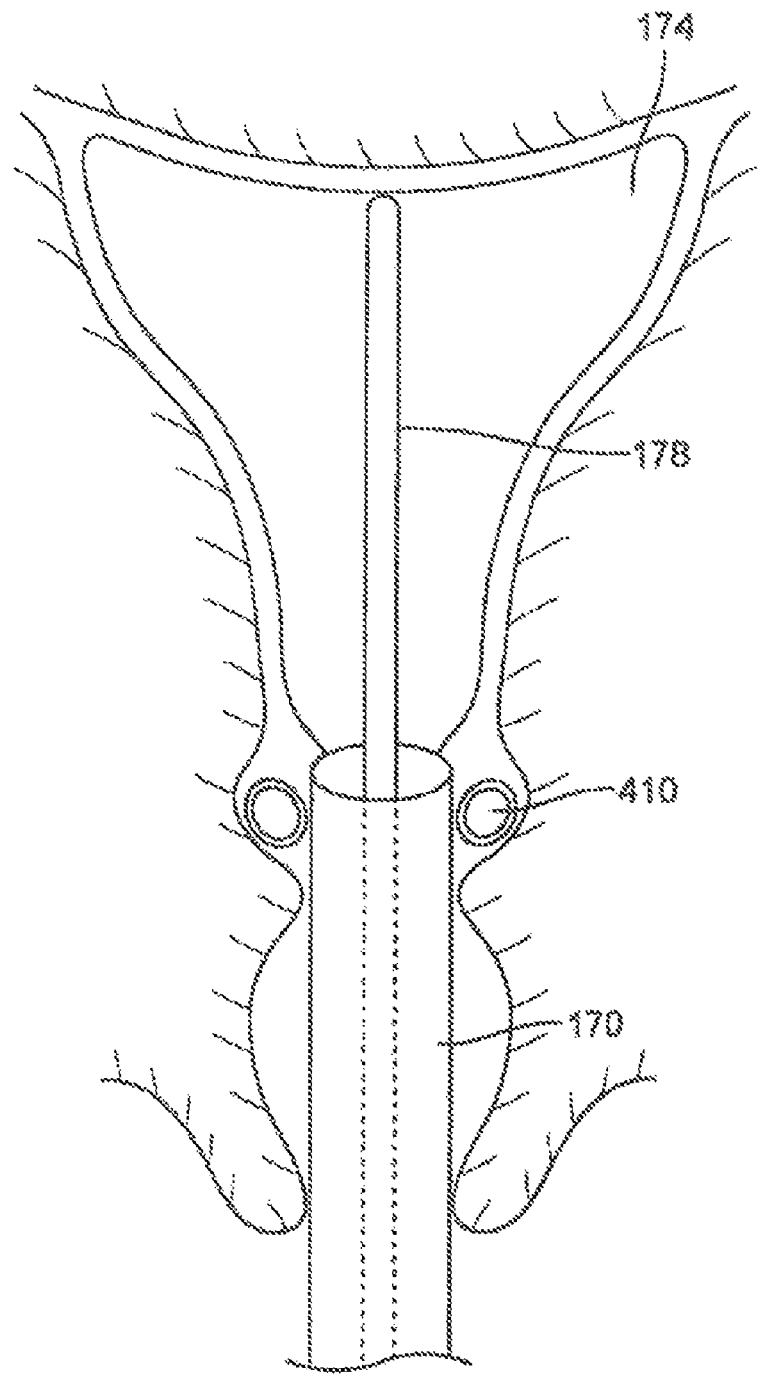
FIG. 65 shows a side view of another example where a ring balloon may be inflated along either the sheath or shaft to either insulate the surrounding cervical tissue or to ensure secure placement of the shaft and/or balloon during treatment.

FIG. 62 shows a cross-sectional side view of another variation of an inflatable liner or balloon 380 located along the inside distal surface of sheath 212. In this variation, the balloon 380 may inflate to insulate the cryoablative fluid from the cervical tissue. FIG. 63 shows another variation where expandable foam 390 may be deployed via the outer sheath 212 for insulating against the cervix CV. FIG. 64 shows yet another variation where a heating element 400 may be located along the inner or outer surface of the elongate shaft 170 for heating the surrounding cervical tissue as the cryoablative fluid is delivered during treatment. FIG. 65 shows yet another variation where a ring balloon 410 may be inflated along either the sheath 212 or shaft 170 to either insulate the surrounding cervical tissue or to ensure secure placement of the shaft 170 and/or balloon 174 during treatment.

Figure 66:
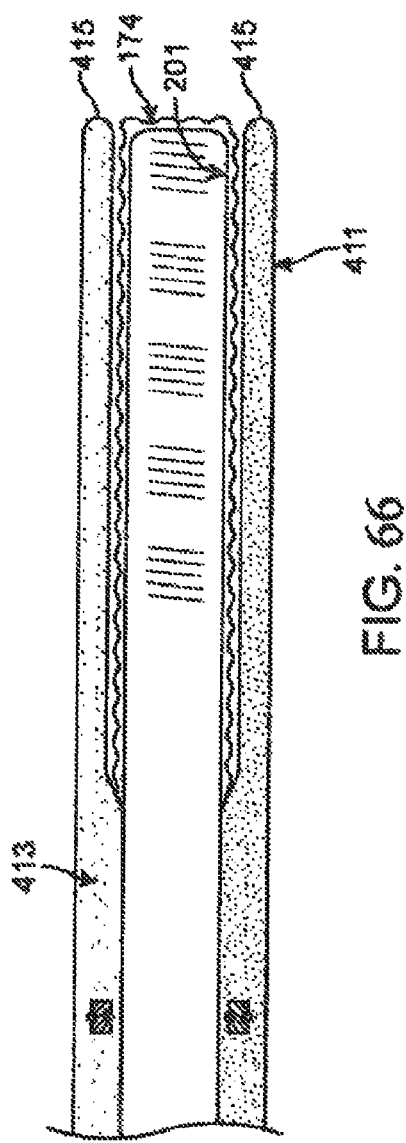
FIG. 66 shows a cross-sectional side view of another variation where the outer sheath may be formed as an inflatable structure.
Figure 67A:
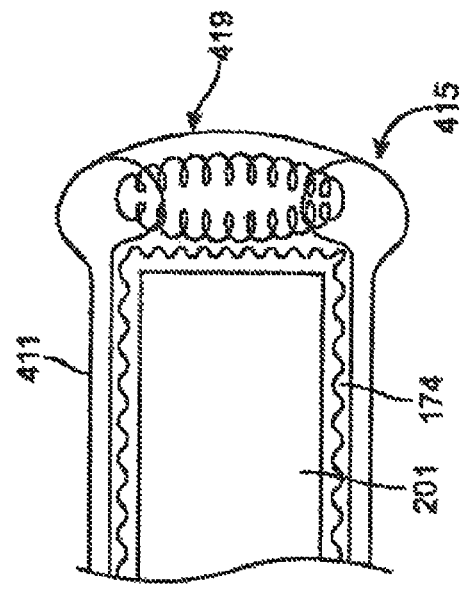
FIGS. 67A and 67B show side views of variations of an outer sheath having a reconfigurable distal end.
Figure 67B:
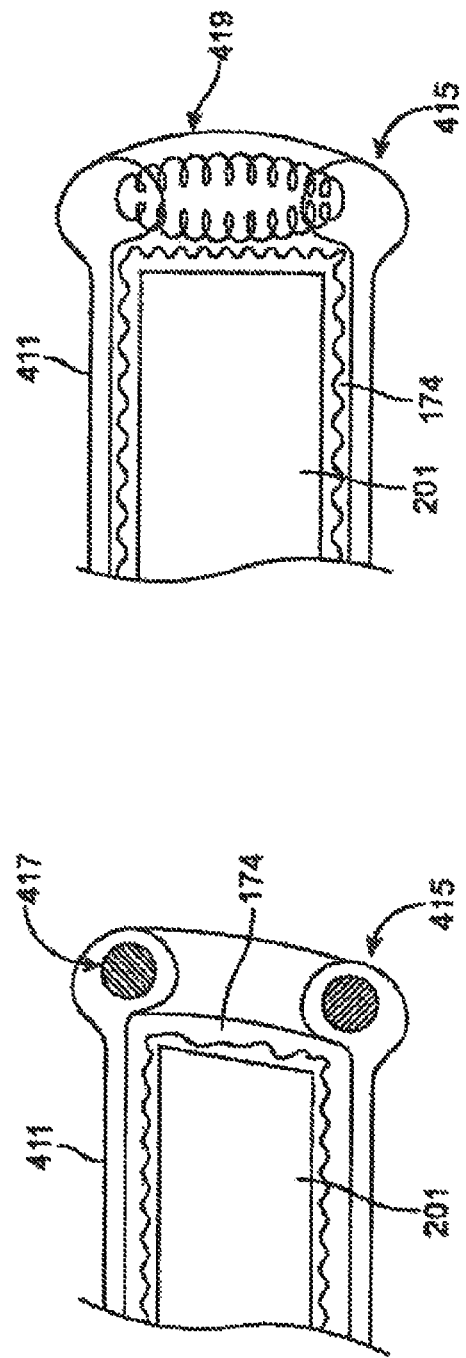

FIG. 66 shows a cross-sectional side view of yet another variation of a sheath 411 which may be formed from, e.g., urethane having a thin wall of about 0.001 in., which may be doubled over and sealed such that the sheath 411 contains a volume of liquid or gas 413 such as saline, air, etc. The cooling probe assembly having the tubing 201 and balloon 174 in its collapsed state may also be seen. The sheath distal end 415 may optionally incorporate a deformable member such as an elastic or expandable ring 417 contained circumferentially within the distal end 415, as shown in the side view of FIG. 67A. Alternatively, a biased circular member such as a ring 419 comprised of a circularly-formed spring may be contained circumferentially within the distal end 415, as shown in FIG. 67B. With the sheath 411 positioned with its distal end 415 distal to the tubing 201, the ring 417 may configure into a ring having a first diameter which at least partially covers the distal opening of the sheath 411. However, when the tubing 201 is advanced from the sheath 411, the ring 417 may stretch or deform into a second larger diameter as it conforms to the outer surface of the tubing 201. The enlarged ring 417 may accordingly form a stop or detent for preventing the proximal over-withdrawal of the sheath 411 relative to the cervix CV as well as facilitating the positioning of the sheath 411 over the cervix CV to provide insulation during a procedure. As the outer sheath 411 and enlarged ring 417 is positioned proximally along the tubing 201 to secure a position of the ring 417 against cervical tissue, the sheath retraction may accordingly adjust an expanded length of the balloon 174 within the uterus UT.

Moreover, since the positioning of the sheath 411 may also actuate and adjust a position of a mandrel 290 within the one or more lines 307 to selectively obstruct or open a selected number of openings 286 (as illustrated in FIG. 41), the single withdrawal and positioning of the outer sheath 411 may not only provide an adjustable securement of the device relative to the cervical tissue, but it may also correspondingly adjust the balloon expanded length and further control the active length of the delivery line 307 via the mandrel 290 positioning. The sheath retraction and securement may be utilized not only in this variation, but in any of the variations shown and described herein, as practicable.

Figure 68:
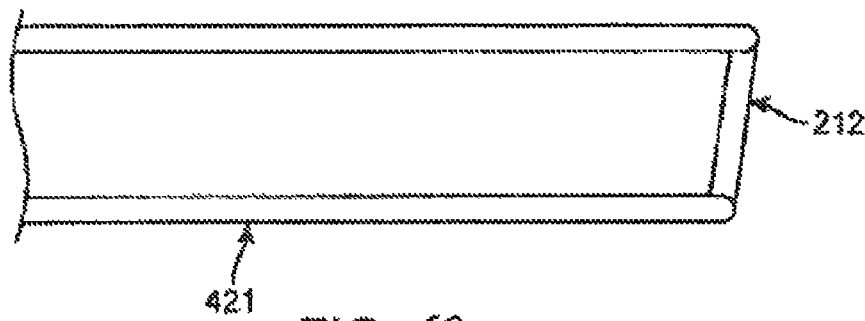
FIG. 68 shows a side view of another variation of a balloon positioned along an outer surface of the outer sheath.
Figure 69:
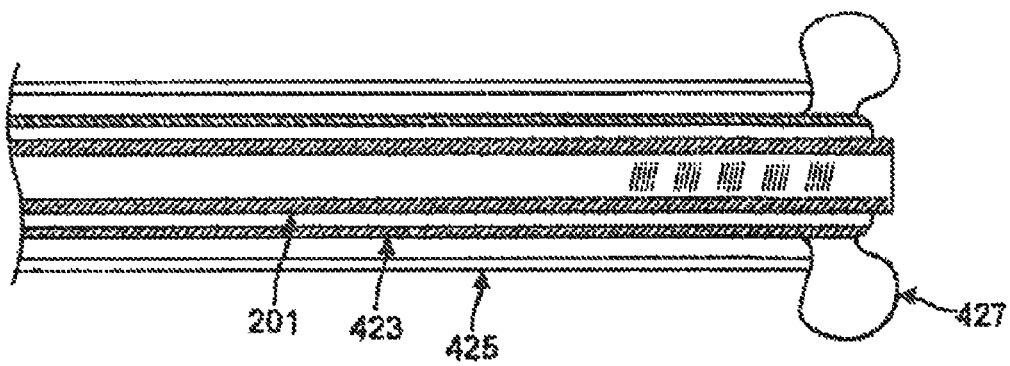
FIG. 69 shows a cross-sectional side view of one variation of a dual-sheath design.
Figure 70A:
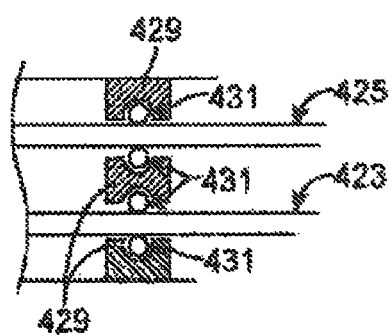
FIGS. 70A and 70B show cross-sectional detail views of the sealing between the inner and outer sheaths.
Figure 70B:
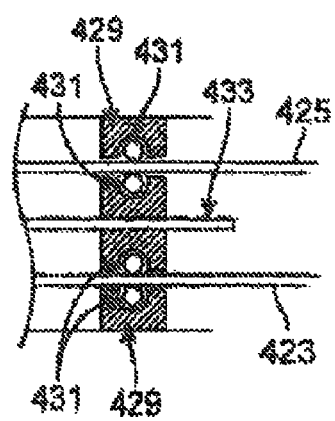

FIG. 68 shows another variation of a cervical protection balloon 421 may have a length, e.g., 4 to 8 cm, that may also be positioned along the outside surface of the sheath 212 (as shown) or along the inside surface for placement against the cervical tissue. FIG. 69 shows a cross-sectional side view of yet another variation of a dual sheath assembly having an inner sheath 423 and an outer sheath 425 which are longitudinally translatable relative to one another. An annular balloon 427 may be attached to the distal ends of both the inner sheath 423 and outer sheath 425 such that the balloon 427 size and configuration may be altered by the relative movement and positioning of the sheaths 423,425. FIGS. 70A and 70B show detail cross-sectional side views of an example of an arrangement for several seals 429 which may be positioned between each respective sheath 423, 425. Corresponding o-ring seals 431 may be incorporated into the seals 429 to provide for fluid-tight sealing. Also, a fluid line 433 may be passed through one or more seals 429, as shown, to provide for inflation and deflation of the balloon 174 or annular balloon 427.

Figure 71:
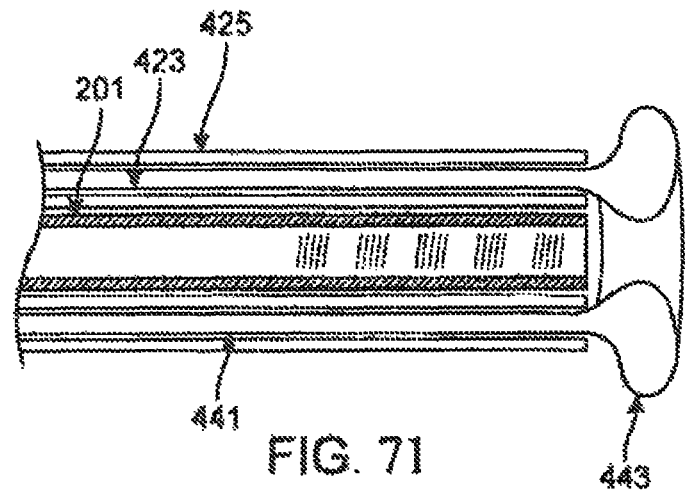
FIG. 71 shows a partial cross-sectional side view of another dual-sheath variation having an expandable balloon contained between the sheaths.

Another variation is shown in the cross-sectional side view of FIG. 71 which shows another dual sheath design where the annular balloon may be comprised of a confined balloon 441 having an expandable balloon portion 443. The balloon, e.g., urethane, may be contained between each respective sheath 423, 425 while a doubled-over portion may be positioned to extend from between the distal ends of the sheaths 423, 425. As inflation fluid is introduced into the balloon, the portion of the balloon constrained between the sheaths 423, 425 may remain collapsed but the unconstrained expandable balloon portion 443 may expand into an annular shape as shown.

Figure 72:
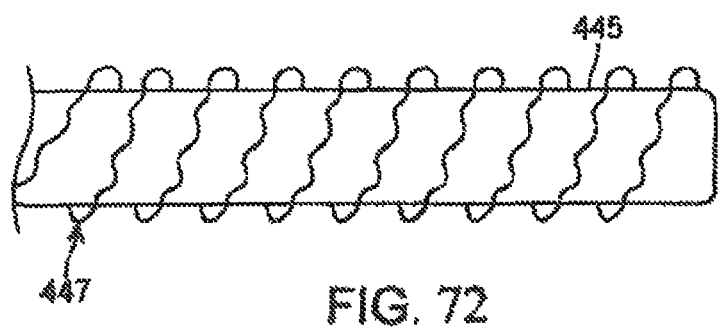
FIG. 72 shows a side view of another variation of a sheath having a reinforced structure.

FIG. 72 shows yet another variation where the sheath 445 may be formed to have a reinforcement member 447, e.g., wire, braid, mesh, etc., integrated along its body to provide for added strength and space between the sheath 445 and adjacent tissue. Any of the balloon embodiments described herein may be incorporated with the sheath 445 as shown.

Figure 73:
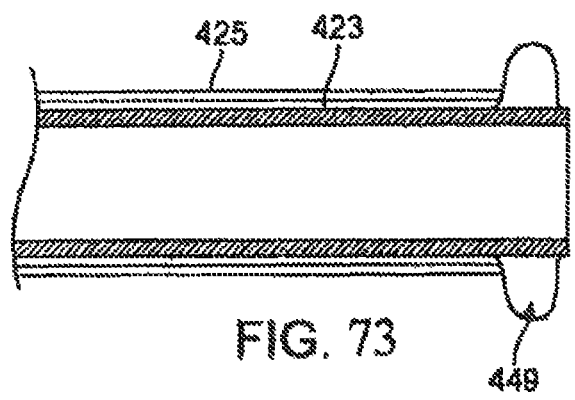
FIG. 73 shows a cross-sectional side view of another variation of an outer sheath having an adjustable balloon member.

FIG. 73 shows another variation of a sheath having an annular balloon 449 positioned along the distal end of the inner sheath 423 while constrained by the distal end of the outer sheath 425. The balloon 449 may be sized according to the relative positioning between the inner and outer sheaths.

FIGS. 74A and 74B show partial cross-sectional side views of yet another example of an outer sheath 451 slidably positioned over tubing 201 where the distal end of outer sheath 451 may incorporate an integrated expandable ring 453, e.g., elastomeric, foam, etc. As previously described in a similar embodiment, the expandable ring 453 may have a first diameter which closes upon the distal end of tubing 201 when the outer sheath 451 is advanced distal to the tubing 201. As the outer sheath 451 is retracted relative to tubing 201, the ring 453 may expand to a larger second diameter as it conforms to the outer surface of the tubing 201. The enlarged profile of the outer sheath 451 may thus function as a stop relative to the cervical tissue during a procedure.

Figure 76:
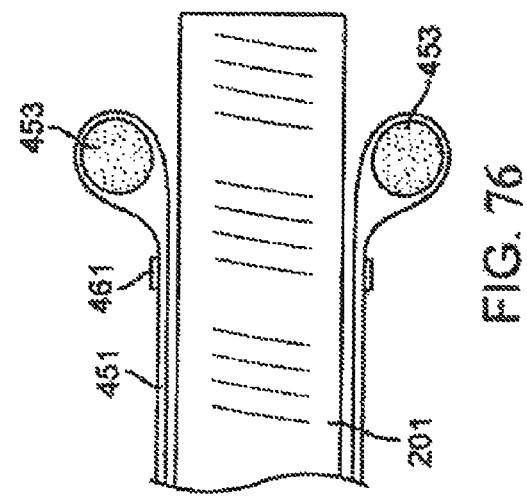
FIG. 76 shows a partial cross-sectional side view of another variation where the reconfigurable distal end may be attached as a separate component.
Figure 75:
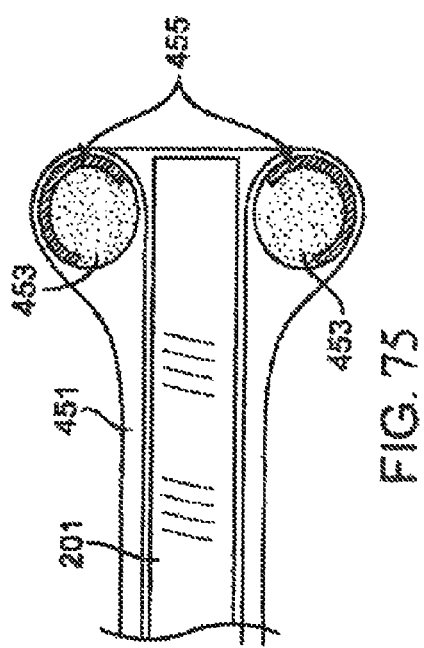
FIG. 75 shows a cross-sectional side view of the reconfigurable distal end having one or more lubricious surfaces.
Figure 77:
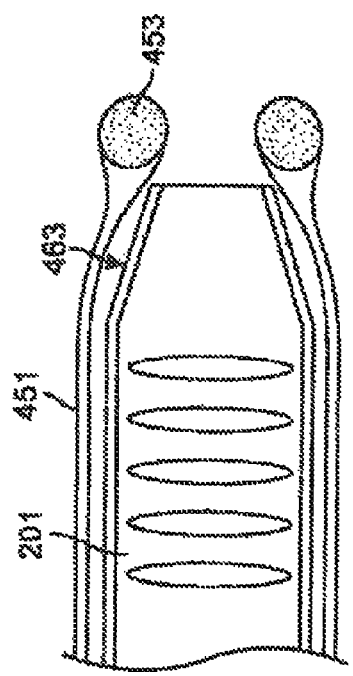
FIG. 77 shows a cross-sectional side view of another variation where a distal end of the cooling probe has a tapered distal end.

FIG. 75 shows a similar variation where the expandable ring 453 may incorporate one or more lubricious surfaces 455 to facilitate the retraction of outer sheath 451, e.g., by peeling the outer layer relative to the inner layer, and the conformance of the ring 453 relative to the tubing 201. FIG. 76 shows a side view of yet another variation where the outer sheath 451 may instead incorporate a discrete ring section 461 having the expandable ring 453 positioned relative to the tubing 201. FIG. 77 shows yet another variation where the distal end of the tubing 201 may define a tapered distal end 463 to facilitate the expansion of the expandable ring 453 when outer sheath 451 is retracted.

In yet another variation of the outer sheath, FIG. 78 shows an embodiment where the outer sheath 465 may have a radially expandable portion 467 formed near or at a distal end of the outer sheath 465. Prior to or during a procedure to secure a position of the outer sheath 465 relative to the cervical tissue, the expandable portion 467 may be utilized rather than an inflatable balloon. The expandable portion 467 may generally comprise one or more lengths of the outer sheath 465 being reconfigurable along a pivotable or bendable portion such that as the distal end of the outer sheath 465 is retracted relative to the remainder of the sheath 465, the one or more lengths may pivot and reconfigure into its radial configuration.

A linkage 475 (such as wire, rod, string, ribbon, etc.) may be coupled to the distal end of the outer sheath 465 at a first stop 469, as shown in the partial cross-sectional side view of FIG. 79A. A second stop 471 may be positioned proximally of the first stop 469 which limits the proximal withdrawal of the linkage 475 by a predetermined distance. When the linkage 475 engages the first stop 469 and retracts the sheath distal end to radially extend the expandable portion 467, the further retraction of linkage 475 may be stopped by the second stop 471. The outer sheath 465 may define the lumen through which the cooling probe assembly may be advanced without interference from the retraction assembly. Another variation is illustrated in FIG. 79B which shows a similar mechanism but where the second stop 471 may be replaced by a biasing element 473, e.g., spring, positioned proximally of the first stop 469.

Figure 80A:
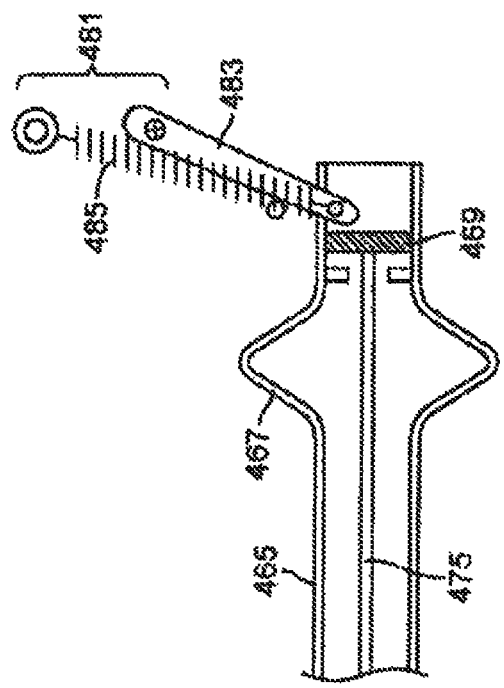
FIGS. 80A and 80B show cross-sectional side views of an illustrative example of an overcenter linkage mechanism.
Figure 80B:
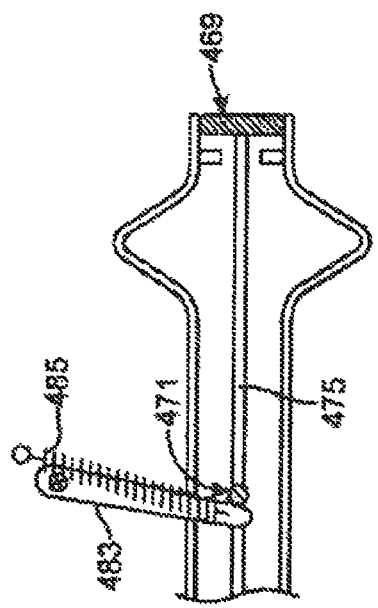

Yet another variation is shown in the side views of FIGS. 80A and 80B which illustrate a representation of an exemplary overcenter linkage mechanism 481 which may be incorporated with the retraction mechanism. A linkage 483 and corresponding biasing element 485, e.g., spring, may be coupled to the linkage member 475 attached to the stop 469. As the linkage 475 is retracted to reconfigure the expandable portion 467, the overcenter mechanism 481 may also be retracted and actuated to engage a position of the linkage 475 such that the retraction of the expandable portion 467 may be selectively maintained. The overcenter mechanism 481 may be selectively disengaged to release and reconfigure the expandable portion 467.

Figure 81:
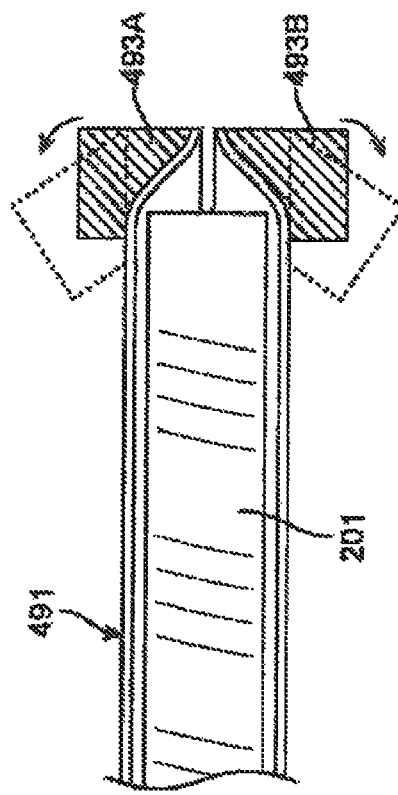
FIG. 81 shows a cross-sectional side view of another variation of an outer sheath having one or more distal cam members.

FIG. 81 shows a side view of yet another variation where the outer sheath 491 may incorporate one or more distal cam members 493A, 493B. With the outer sheath 491 positioned distally of the tubing 201, the cam members 493A, 493B may be configured into a first collapsed configuration. As the outer sheath 491 is retracted relative to tubing 201, the cam members 493A, 493B may pivot along outer sheath 491 when urged by the outer surface of the tubing 201 and reconfigure into an expanded configuration as indicated. The reconfigured expanded cam members 493A, 493B may then be used as a stop for the outer sheath 491 relative to the cervical tissue.

An example of the reconfigured cam members 493A, 493B used as a stop is illustrated in the exemplary cross-sectional side view of FIG. 82. As indicated, as the outer sheath 491 is retracted and the cam members 493A, 493B reconfigure, the outer sheath 491 may be further retracted until secured against the cervix CV. FIG. 83 shows another example where the outer sheath 501 having the distal tip cam members 503A, 503B may be configured to have a tapered distal end 505 to allow for the further pivoting of the cam members 503A, 503B during sheath retraction.

FIG. 84 shows an exemplary illustration of how the outer sheath 465 may be deployed first and secured into position with, e.g., the expandable portion 467, placed into contact against the cervix CV. The cooling probe assembly and collapsed balloon 174 may then be inserted through the outer sheath 465 at a later time and advanced into the uterus UT for treatment. In this and any of the other variations described herein, as practicable, the outer sheath may be deployed independently of the cooling probe if so desired.

Figure 85:
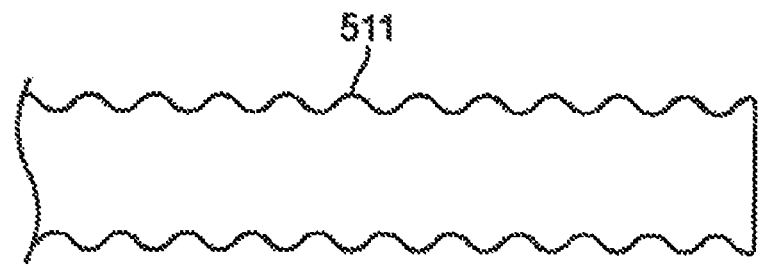
FIG. 85 shows a side view of another variation where the outer sheath is configured as a corrugated structure.
Figure 86:
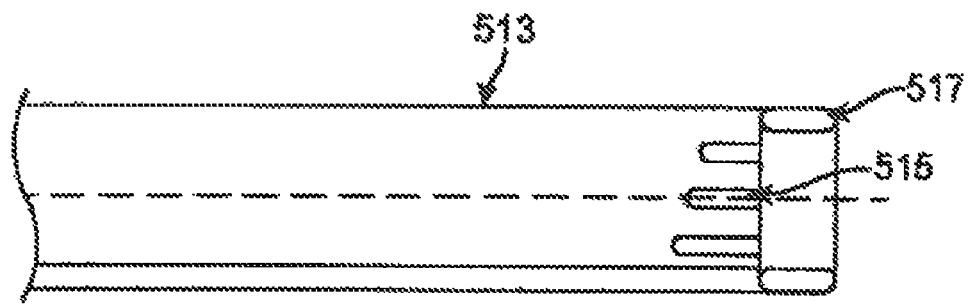
FIG. 86 shows a partial cross-sectional side view of another variation of the outer sheath having an inflatable balloon along an inner surface.
Figure 87:
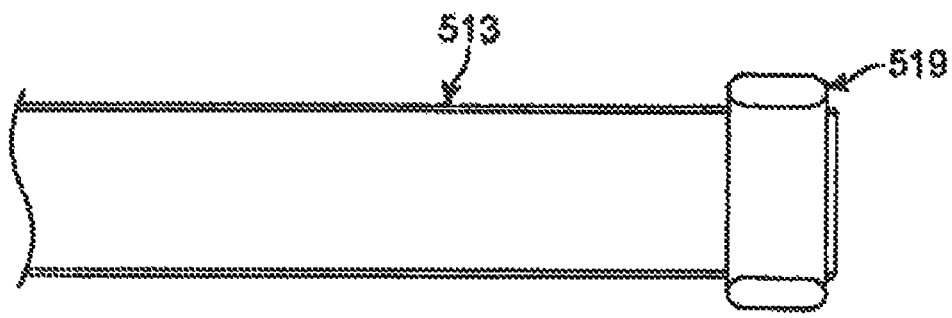
FIG. 87 shows a partial cross-sectional side view of another variation of the outer sheath having an inflatable balloon along an outer surface.

FIG. 85 shows yet another variation where the outer sheath may be configured as a corrugated outer sheath 511 to provide a structure which is strong yet flexible. FIGS. 86 and 87 show additional variations where the outer sheath 513 may comprise an annular balloon 517 located along inner surface of sheath 513. The sheath distal end may define one or more longitudinal slots 515 for selective expansion of the balloon 517. Alternatively, the annular balloon 519 may be located along outer surface of sheath 513, as also previously described.

Figure 88B:
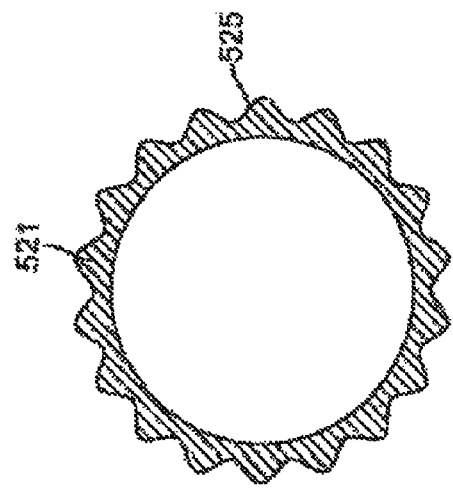
FIG. 88A to 88D show cross-sectional end view of variations of the outer sheath having an integrated feature to provide further insulation to the surrounding tissue.
Figure 88D:
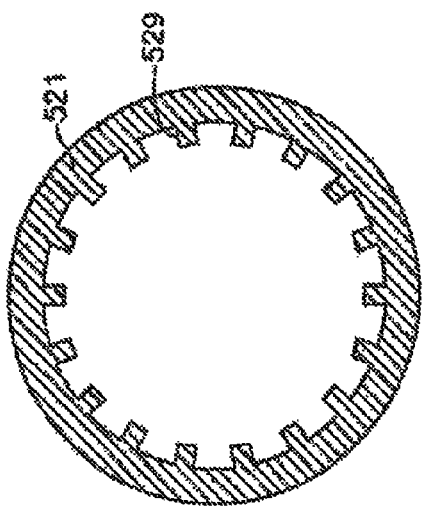
Figure 88A:
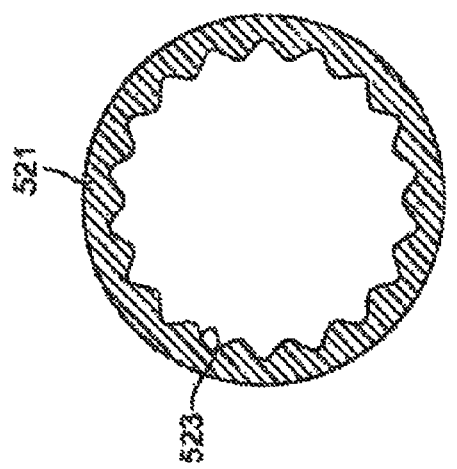
Figure 88C:
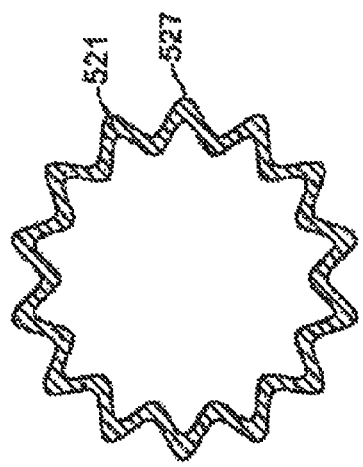

FIGS. 88A to 88D show yet another variation where the sheath 521 may incorporate an integrated feature to provide further insulation between the cryoablative fluid and the surrounding cervical tissue by creating or forming insulative pockets of air. The variation shown in the cross-sectional end view of FIG. 88A shows a sheath 521 defining a plurality of raised and curved surfaces 523 along the inner surface of the sheath 521. FIG. 88B shows another variation where a plurality of raised and curved surfaces 525 may be formed along the outer surface of the sheath 521. Yet another example is shown in FIG. 88C which shows a sheath 521 formed to have both internal and external raised surfaces 527 while the variation of FIG. 88D shows a variation where the internal sheath surface may have a plurality of raised projections or fingers extending inwardly.

In controlling the ablative treatments described above, the treatment assembly may be integrated into a single cooling system 420, as shown in the exemplary schematic illustration of FIG. 89. The cooling system 420 may be contained entirely within the handle assembly 214 as described above or it may be separated into components, as needed or desired. In either case, the cooling system 420 may generally comprise a microcontroller 422 for monitoring and/or controlling parameters such as cavity temperature, cavity pressure, exhaust pressure, etc. A display 424, e.g., a digital display which may be located along handle assembly 214, may be in communication with the microcontroller 422 for displaying parameters such as cavity pressure, cavity temperature, treatment time, etc. Any errors may also be shown on the display 424 as well. A separate indicator 426, e.g., visual or auditory alarm, may also be in communication with the microcontroller 422 for alerting the user to prompts, errors, etc. through as any number of indicators, symbols, or text, etc., for alerts, as well as for instructions, or other indications.

A coolant reservoir 428, e.g., nitrous oxide canister in this example, may be fluidly coupled to the handle 214 and/or elongate shaft 170 via a coolant valve 430 which may be optionally controlled by the microcontroller 422. The coolant reservoir 428 may be in fluid communication with the cooling probe assembly 220 and with the interior of the balloon 174. One or more pressure sensors 432 may be in communication with a pressure lumen 434 contained within the cooling probe assembly 220 or elongate shaft 170 and one or more temperature sensors 436 in communication with a thermocouple/thermistor wire 438 also contained within the cooling probe assembly 220 or elongate shaft 170 may be incorporated. The one or more pressure sensors 432 and/or temperature sensors 436 may be in communication with the microcontroller 422 as well. Moreover, the pressure sensors 432 may optionally comprise a sensor positioned within the balloon 174 where the sensor is designed for low temperature measurement. Such a pressure sensor may incorporate a closed or open column of liquid (e.g., ethanol, etc.) or gas (e.g., air, carbon dioxide, etc.) which extends through the cooling probe assembly.

The cryoablative fluid contained within the coolant reservoir 428, such as nitrous oxide, may be pumped (or allowed to flow if reservoir 428 is under pressure) via, e.g., a motor-driven valve such as coolant valve 430, to control nitrous oxide inflow rate. The valve 430 may also be used to maintain a desired amount of back pressure to separate the walls of the uterus. For instance, a relatively low back pressure of, e.g., 40 to 60 mm Hg, may be used. Alternatively, a simple but precise exhaust flow restriction might be all that is needed, e.g., such as a fixed, non-adjustable valve. In yet another alternative, vacuum pressure may be used to control the rate at which the exhaust gas is pulled-through, e.g., a nitrous oxide deactivation filter.

The rate at which the cryoablative fluid, such as the nitrous oxide, is delivered may be controlled by the temperature measured within the balloon 174 and/or uterine cavity. The target temperature range may range, e.g., between −65 and −80 degrees C. By limiting the temperature measured within the balloon 174 to a value which is lower than the boiling point of nitrous oxide, about −88.5 degrees C., the chance of liquid nitrous oxide build-up in the balloon 174 may be greatly reduced to prevent any excessive intrauterine pressures if the exhaust tube is blocked.

In the event that excessive pressure is measured within the balloon 174 or the pressure differential between two sensors is too large, the system may be programmed to automatically stop the flow of the cryoablative fluid. A separate shut-off valve may be used in-place of the coolant valve 430. Furthermore, if electrical power is interrupted to the system, the separate shut-off valve may automatically be actuated. In addition, the indicator 426 may signal to the user that excessive pressures were reached and the system shut-down.

The inside diameter of the delivery line may also be sized to deliver cryoablative fluid up to but not exceeding, e.g., a maximum anticipated rate for a large, well-perfuse uterus. By limiting the rate of cryoablative fluid infusion and sizing the exhaust tube appropriately, the system may be able to evacuate the expanded gas even in the event of a catastrophic failure of the delivery line.

Additionally, an exhaust lumen 440 in communication with the elongate probe 170 and having a back pressure valve 444 may also include a pressure sensor 442 where one or both of the back pressure sensor 442 and/or valve 444 may also be in communication with the microcontroller 422. While the microcontroller 422 may be used to control the pressure of the introduced cryoablative fluid, the pressure of the cryoablative fluid within the balloon 174 interior may also be controlled automatically by the microcontroller 422 adjusting the back pressure valve 444 or by manually adjusting the back pressure valve 444. In the event that the microcontroller 422 is used to control the back pressure via valve 444, the microcontroller 422 may be configured or otherwise programmed to adjust the valve 444 based on feedback from other sensors, such as the measured parameters from the one or more pressure sensors 432 and/or temperature sensors 436 to create a closed feedback loop system. A vacuum may also be optionally incorporated into the closed feedback loop.

The exhaust lumen 440 may be fluidly connected, e.g., to a reservoir 446 for collecting or deactivating the exhausted cryoablative fluid. The reservoir 446 may optionally incorporate a filter into the handle 214 or become integrated into a reusable console. Alternatively, the exhausted cryoablative fluid may be simply collected in a reservoir 446 or exhausted into atmosphere.

Generally, redundant pressure lines and sensors, such as pressure lumen 434, that terminate in the balloon 174 may correspond to sensors located in the handle 214 to make comparison measurements. The pressure lines may be filled with a fluid such as ethanol to prevent freezing during a procedure. Alternatively, a gas such as air may be used in the pressure lines but may utilize temperature compensation.

As at least one thermocouple may be located within the balloon 174 and used to measure temperature during the procedure, additional thermocouples may be optionally included at other locations internal or external to the balloon 174 to provide for additional temperature measurements. For example, a thermocouple may be optionally located on the distal portion of the sheath 212 to monitor temperature within the cervix CV.

After completion of the procedure, all unused cryoablative fluid still contained in the reservoir 428 or within the system may be automatically or manually vented, e.g., to the deactivation filter or collection reservoir 446.

The system 420 may optionally further incorporate an emergency shut-off system which may be actuated in the event that electrical power is lost, if a user manually activates the shut-off system, or in the event that the microcontroller 422 detects a high-pressure within the system 420. One example of the emergency shut-off system may incorporate an emergency shut-off valve which may include valve 430 or which may alternatively incorporate another valve separate from valve 430. Moreover, in detecting the pressure within the system 420, a redundant pressure sensor may also be utilized along with the one or more pressure sensors 432 either at the same location or at a different location along the system 420.

In any of the examples described herein, the system may employ a thermally conductive fluid having a thermal conductivity greater than that of saline. This thermal conductivity may help to ensure that the fluid within the body cavity or lumen is at the same temperature throughout even without agitation or lavage. Such a fluid may be used with the fluid lavage and/or the fluid infusion followed by application of a cryoprobe. The improved thermal conductivity may be achieved via a variety of different options including, but not limited to, choice of a thermally conductive fluid or gel, addition of thermally conductive compounds to the fluid or gel (e.g., metals or metal ions, etc.) and/or agitation of the fluid within the cavity to help achieve equilibration of the temperature. Additionally, the fluid may be infused as a fluid or gel until a set pressure is achieved. The cryoprobe may then be introduced into the body cavity/lumen and heat may be withdrawn from the fluid/gel. Prior to or in concert with the achievement of a cryotherapeutic (ablative or non-ablative) temperature, the fluid or may form a gel or solid. This may be utilized such that fluid or gel within the cavity may be trapped within the target lumen or body cavity with its change in viscosity or state thereby preventing leakage of the fluid or gel and unwanted exposure of adjacent tissues to the cryotherapeutic effect. Due to the higher thermal conductivity or the gelled or frozen fluid or gel, the continued removal of heat from the gelled or frozen mass may be rapidly and uniformly distributed throughout the body cavity or lumen. The solution may also be partially frozen or gelled and then agitated or recirculated to ensure even greater distribution of the cryotherapeutic effect. Moreover, the fluid may also be formulated to have a freezing temperature at the desired ablation temperature such that the fluid remains at the desired ablation temperature for a significant amount of time while the fluid changed from a liquid to a solid or vice versa.

Furthermore, the fluid or gel may be made thermally conductive by the addition of a biocompatible metal or metallic ion. Any metal or conductive material may be used for this purpose, e.g., silver, gold, platinum, titanium, stainless steel, or other metals which are biocompatible. Alternatively the thermally conductive fluid may be used to transmit the thermal energy to tissues in order to provide thermal ablation as opposed to the extraction of energy with cryoablation. In either embodiment, with sufficient thermal conductivity the fluid may act as an extension of the ablative energy source and provide a custom ablation tip for the application of or removal of energy from any body tissues, body cavities, or body lumens. Another benefit is consistency of treatment since cryoablation may require use of ultrasound in the setting of uterine ablation. Any of the devices herein may allow for the use of temperature tracking or simple timed treatment in order to automate the ablation (with or without ultrasound monitoring). For example, application of −80 C for 3 minutes has been shown to provide the correct depth of ablation for many uterine cavities. The devices herein may allow for tracking of temperature such that once a desired temperature is reached (e.g., −60 C) a timer may be triggered which automatically discontinues therapy and warms the cavity based on time alone. This may be used in the setting of a fixed volume infusion (e.g., 10 to 15 cc of thermally conductive fluid/gel for all patients) or in the setting of infusion of a fluid/gel to a set pressure (with variable volumes). This timed ablation may also be used in concert with any of the device herein to allow for elimination of the burdensome requirement for ultrasound tracking of the cryogenically treated regions.

Alternatively, this thermally conducting fluid (which may optionally include solid particles of metal) may be infused into a balloon which conforms to the uterus, esophagus or other body cavity or lumen at relatively low pressures (e.g., less than 150 mmHg), as also described above. The thermally conducting material may alternatively be comprised entirely of a solid (e.g., copper spheres or a copper chain) within the conforming balloon wherein the thermally conductive solid and/or fluid may be reversibly delivered into the conforming balloon under low pressure after which a cryoprobe, cryogenic liquid and/or cryogenic gas may be delivered into the balloon and activated to ablate the entirety of the uterus UT at once. The cryogen source may also be positioned within the balloon to obtain maximum cryoablation within the body of uterus with less ablative effect proximally and in the cornua. Vaseline, oils or other thermally resistive materials may also be used in conjunction with this or other modalities in order to protect certain areas of the uterus, cervix and vagina.

In creating the optimal thermally conductive fluid and/or gel, any conductive material may be added to the fluid or gel including, e.g., gold, silver, platinum, steel, iron, titanium, copper or any other conductive metal, ion, or molecule. If a metal is used as a dopant to increase the thermal conductivity, the added metal may take any shape or form including spheres, rods, powder, nanofibers, nanotubes, nanospheres, thin filaments or any other shape that may be suspended in a solution or gel. The fluid or gel may itself also be thermally conductive and may be infused and then removed or may be left in the cavity and allowed to flow naturally from the uterus as with normal menstruation. The thermally conductive polymer may also be biocompatible, as well, but this may not be necessary if the fluid/gel is extracted immediately following the procedure.

Despite the potential for toxicity, ethanol may be well suited for a liquid lavage in that it resists freezing down to −110 C and is, other than dose dependent toxicity, biocompatible. Solutions of 75% to 99.9% ethanol concentrations may be used to good effect and have been demonstrated to show that a freeze layer develops very rapidly inhibiting further ethanol absorption. An ethanol copper composition may also be used since ethanol resists freezing whereas aqueous fluids freeze and expand thereby moving the metal particle out of direct contact with the tissue.

Figure 90A:
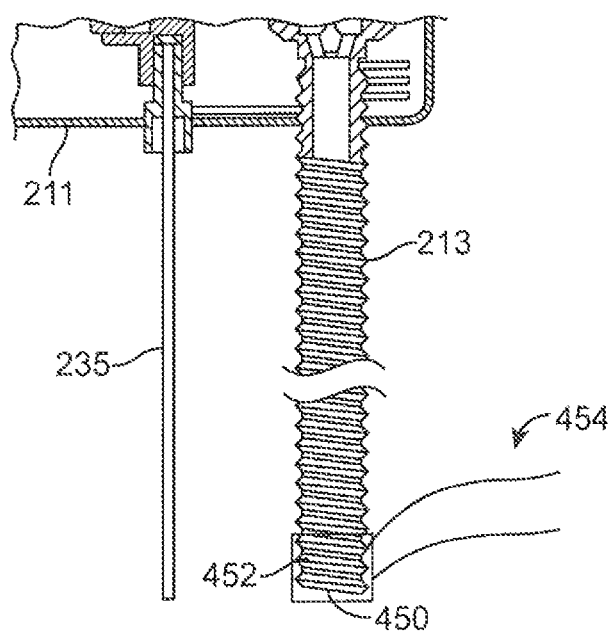
FIGS. 90A and 90B show a device for closing the exhaust flow path to facilitate a liner integrity check and to also increase the pressure within the uterine cavity.
Figure 90B:
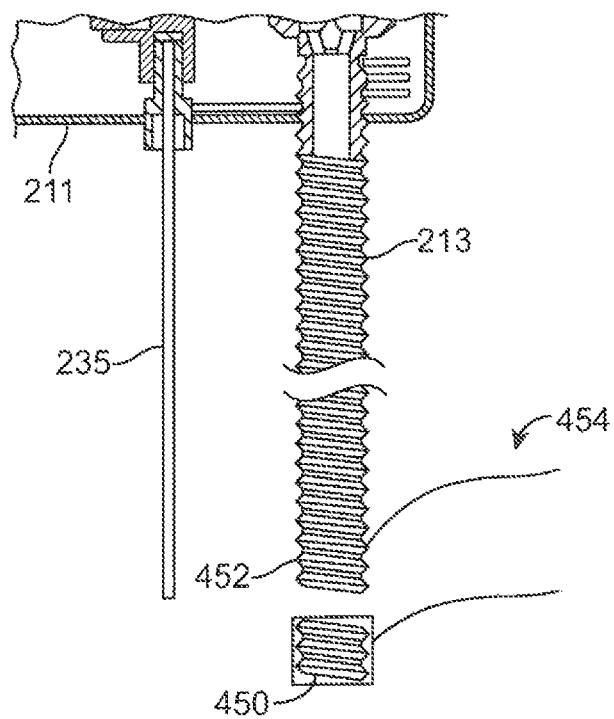

In another variation for creating back pressure within the system, FIGS. 90A and 90B show a device for closing the exhaust flow path to facilitate a liner integrity check and to also increase the pressure within the uterine cavity. As the liner is initially expanded (e.g., up to 100 mmHg of pressure), the transition between initial expansion and treatment should desirably occur with a minimal change in cavity pressure. Hence, the pressure within the liner and system during the first 30 seconds of treatment is ideally maintained 85+/−15 mmHg. The variation shown in FIG. 90A illustrates an end cap 450 which may be used to cover or obstruct the exhaust line 213 to facilitate the increase in back pressure during the initial expansion. The end cap 450 may contact the exhaust tube contact 452 over the exhaust line 213 such that the end cap 450 and exhaust tube contact 452 are electrically coupled to form a circuit via conductive lines 454.

Once sufficient back pressure has been created in the system and cryoablation treatment is ready to begin, the end cap 450 may be removed from the exhaust tube contact 452 (manually or automatically) breaking the electrical connection, as shown in FIG. 90B. The processor or microcontroller in the system may detect the electrical break and automatically initiate infusion of the cryoablative fluid or gas to begin the treatment. Moreover, because the exhaust line 213 is now unobstructed, the discharged fluid or gas may also be vented or removed from the system through exhaust line 213.

In other variations for maintaining exhaust back pressure within the system, the pump (with or without a filter) may be used to increase the pressure. Alternatively, a compressed gas (e.g., coupled via a bladder, tank, etc.) may be infused into the liner and system to increase the pressure. In either case, any of these methods may be used in various combinations with any of the system or device variations described herein.

Alternative mechanisms may also be used for maintaining a sufficient back pressure within the system and the liner. Another variation is shown in the schematic side view of FIG. 91A of flapper valve 460 such as an electromechanical flapper valve which may be incorporated within the handle assembly 211 (e.g., positioned between the pump and the liner) for fluidly coupling to the liner and exhaust. FIG. 91 illustratively shows flapper valve 460 having a chamber 462 with a translating piston 464 within the chamber 462. The pump 468 may be fluidly coupled via pump line 470 to the first section 480 of the chamber 462 (e.g., at a top of the chamber 462) and exhaust and/or liner channel 472 may also be similarly fluidly coupled to the first section 480 of chamber 462. The exhaust and/or liner channel 472 may also incorporate a unidirectional valve 474 within the channel 472 such that fluid or gas may pass through channel 472 and past unidirectional valve 474 but is prevented from flowing back into first chamber 480.

The exhaust and/or liner channel 476 may be fluidly coupled to the second section 482 of chamber 462 (e.g., at the bottom of the chamber 462) in proximity to ambient line 478. A sealing gasket 466 having a first sealing ring 466A which encircles the periphery of the chamber 462 and a second sealing ring 466B which encircles the entry to the exhaust and/or liner channel 476 may also be incorporated in the second chamber 482, as shown in the top view of FIG. 91B.

The flapper valve 460 may remain closed by the system (e.g., motor, linear actuator, magnetic, electromagnetically, etc.) but opened by the system as the ablation treatment begins. The flapper valve may be actuated, e.g., by a separate button or actuator, positioned upon the handle assembly 211.

Figure 91A:
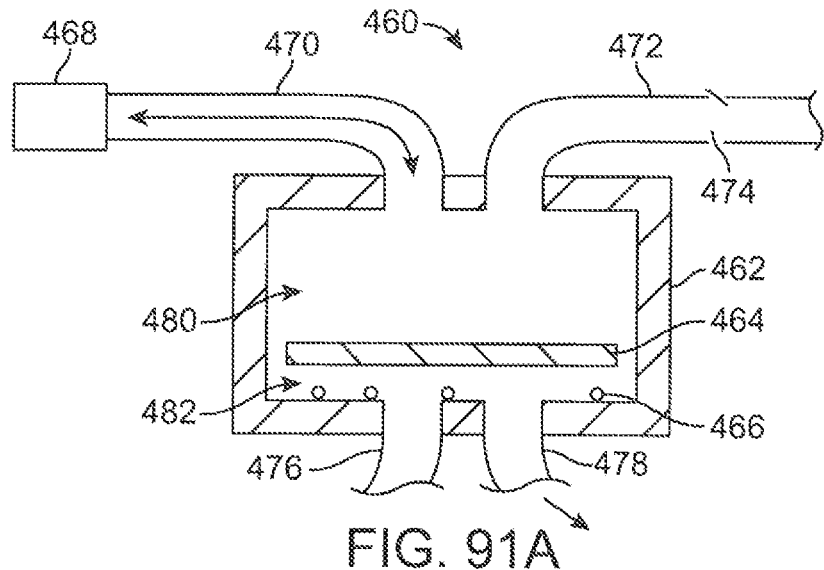
FIGS. 91A and 91B show a schematic side view of a flapper valve and a top view of a gasket within the flapper valve for maintaining exhaust back pressure within the system.
Figure 91B:
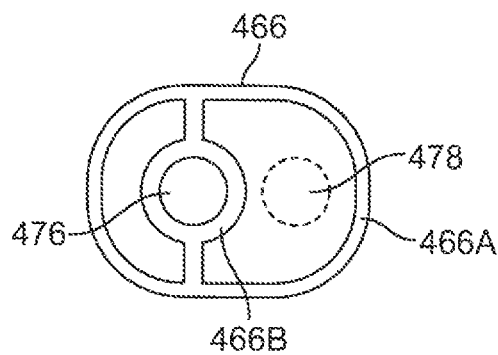
Figure 91C:
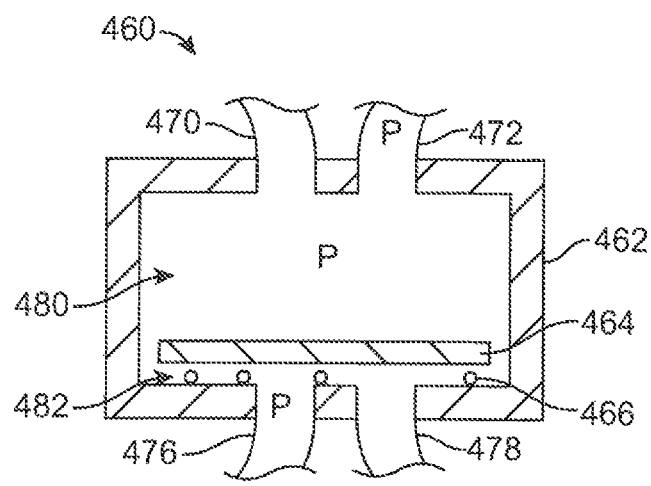
FIGS. 91C to 91E show schematic side views illustrating an example of the flapper valve operation.

When actuated, the pump 468 may be turned on and the piston 464 may remain positioned at the bottom of the chamber 462 upon the sealing gasket 466, as shown in the side view of FIG. 91C. The piston 464 may form a moderate seal while sitting upon the gasket 466 but as the pressure in the chamber 462 is increased, the sealing between the piston 464 and gasket 466 may be increased accordingly. The gasket 466 itself may form different regions of relatively low pressure in the area between the first sealing ring 466A and the second sealing ring 466B (e.g., at atmospheric pressure) and high pressure in the area surrounded by the second sealing ring 466B (e.g., at the same pressure as within the liner/exhaust) during the initial pump up phase.

After the liner has been pumped up to its pre-determined pressure level to properly distend the cavity and deploy the liner (e.g., 85 mmHg), the pump 468 may be reversed to remove the pressure from the chamber 462. The one-way or uni-directional valve 474 may prevent the vacuum from pulling on the liner as would the seal at the bottom of the chamber 462 formed by the piston 464.

Figure 91D:
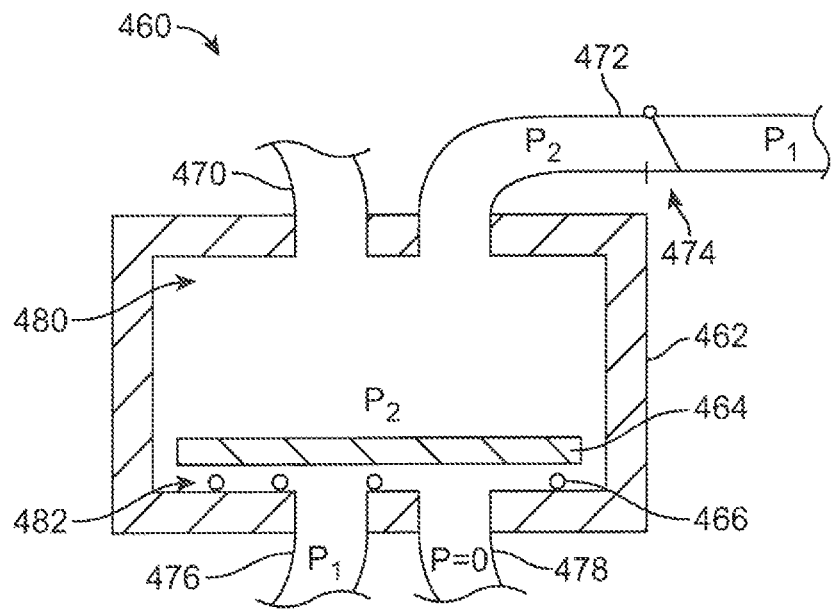
Figure 91E:
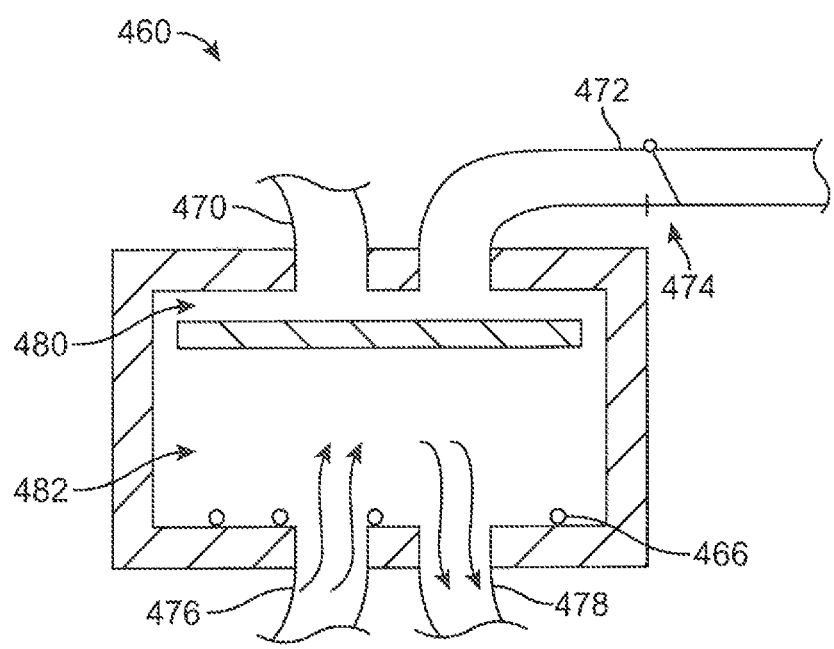

When P2 is lowered, the force of P1 upon the bottom of the piston 464 may cause it to lift within the chamber 462, as shown in FIG. 91D. This piston movement will cause P1 to drop as the seal at the bottom breaks and as P1 begins to drop, the vacuum may shut off and the treatment may be initiated. The flow of the cryogenic fluid or gas through the chamber 462 may cause the piston 464 to move to the top of the chamber 462 which may allow for the free flow of nitrous to the environment, as shown in FIG. 91E.

Figure 92A:
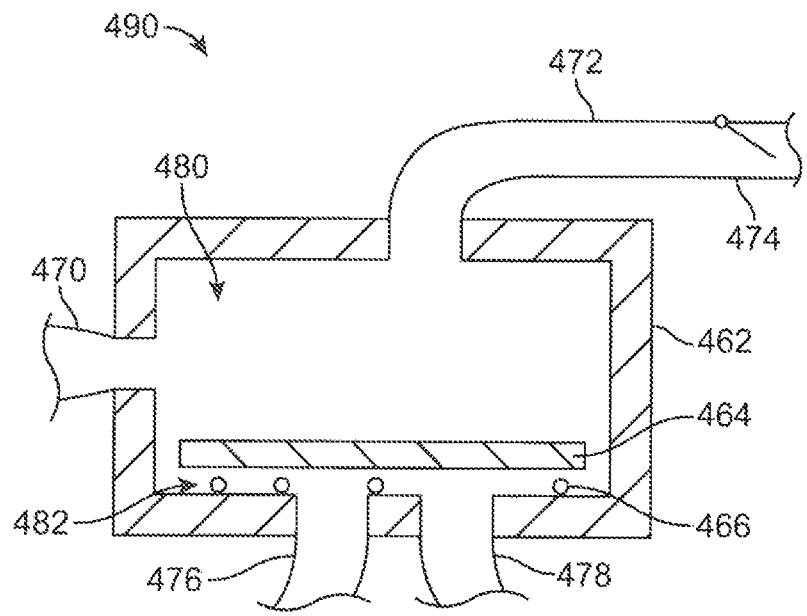
FIGS. 92A and 92B show schematic side views of another variation of the flapper valve.
Figure 92B:
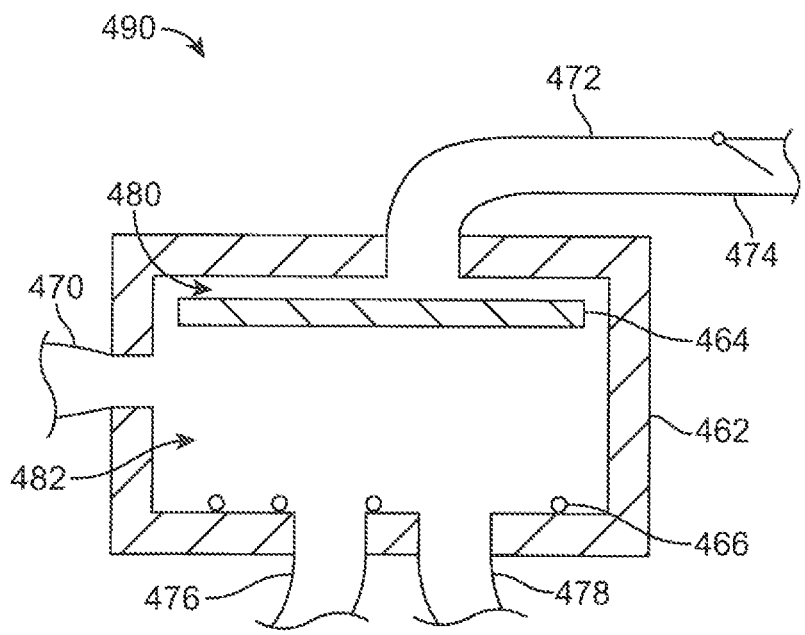

FIGS. 92A and 92B show an alternative flapper valve 490 which may function similarly except for the pump/vacuum line 470 may be positioned along a side wall of the chamber 462. With the vacuum/pump line 470 so positioned, the line 470 may remain below the piston 464 while the cryogenic fluid or gas flows through the chamber 462, as shown in FIG. 92B. If the back pressure in the system is too high, the pump or a vacuum pump 468 may be actuated to provide a slightly negative pressure or suction that may lower the back pressure on the system.

Figure 93:
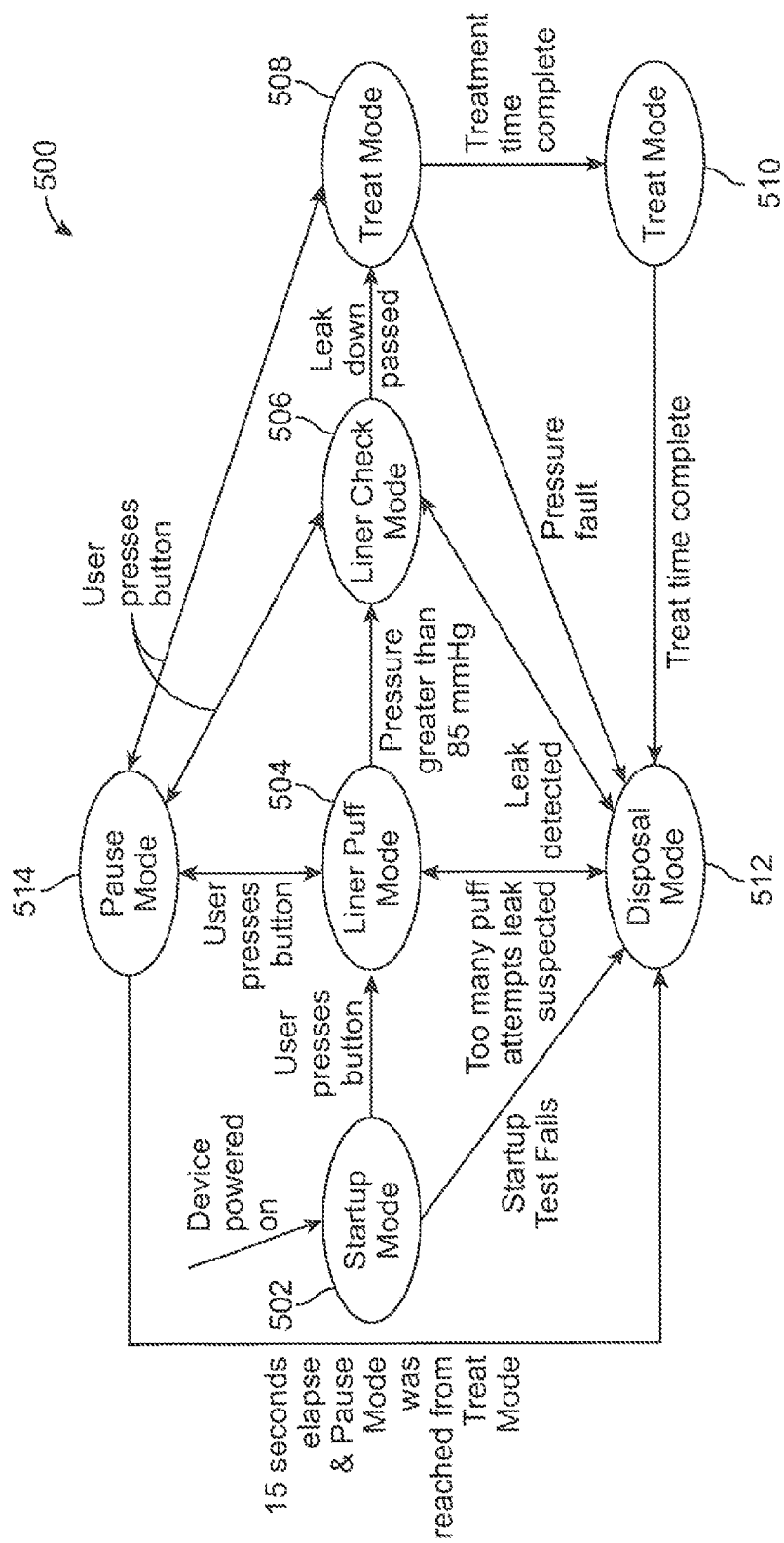
FIG. 93 shows how the various algorithms may be programmed into the processor or microcontroller and how they may functionally interact with one another.

As previously described, the system may be programmed to enable a number of different processes. The processor or microcontroller may be accordingly programmed with a number of different algorithms depending on the functional mode to be performed. FIG. 93 illustrates how the different algorithms 500 may be programmed into the processor or microcontroller and how they may functionally interact with one another. Once the device is initially powered on, the system may enter a Start-Up Mode 502 where the system performs a self-check of the sensors and the overall system. Some of the checks may include, e.g., ensuring pressure sensors have a detected initial reading of between 0 and 10 mmHg which do not deviate from one another by more than 5 mmHg; detecting a battery voltage reading of greater than 7.5 V; and/or detecting any memory feature which may be used to record various readings and parameters as well as load any number of additional features into the system.

Once the Start-Up Mode 502 has been initiated and/or completed, the user may, e.g., actuate the system to enter a Liner Puff Mode 504. In Liner Puff Mode 504, the system may slowly add ambient filtered air into the liner until target treatment pressure is reached, as described above. The pump may be turned on until the pressure has increased by, e.g., 5 mmHg, and may then be shutoff for, e.g., 2 seconds. The pump may cycle on and off until the system measures, e.g., 85 mmHg. Typically, the full ramp-up may take, e.g., 15-20 seconds. When 85 mmHg is reached, the device may then enter Liner Check Mode 506. In this mode, the system may detect for leaks in the system. The system may waits for, e.g., 5 seconds, after Liner Puff Mode 504 is complete and then detect whether the pressure is still above, e.g., 40 mmHg or more. If the system is holding pressure, the device may then enter Treat Mode 508.

During Treat Mode 508, the system may deliver the cryogenic fluid or gas to the liner while looking for pressure faults. An example of a pressure fault may include a detected pressure value greater than, e.g., 150 mmHg. The treatment may be stopped automatically and user restart may be halted at least temporarily by the system. Another example of a pressure fault may include when a detected pressure deviates from other pressure readings by, e.g., 20 mmHg or greater for 3 consecutive seconds. Again, treatment may be stopped automatically and user restart may be halted at least temporarily by the system. Once a predetermined time period has elapsed, e.g., 2 minutes and 30 seconds, the device may enter Thaw Mode 510.

In Thaw Mode 510, the system may push puffs of ambient filtered air into the liner to warm it up for removal from the patient. The pump may push air into the cavity while the exhaust solenoid is closed until, e.g., 10 mmHg pressure in the cavity is measured. The pump may be then turned off and the exhaust solenoid opened for, e.g., 2 seconds to allow the air to escape the cavity. The pump/open cycle may be repeated for, e.g., 2 minutes. Additionally and/or optionally, a vacuum may also be used in Thaw Mode 510, e.g., to facilitate peeling of the liner 174 from the frozen uterine walls and to expedite the removal of the device.

Once Thaw Mode 510 has been completed, the system may then enter Disposal Mode 512 where the liner and system may be evacuated of any cryogenic fluid or gas. In the event that any of the different modes detects a failure, e.g., if the Startup Mode 502 fails, too many puff attempts are detected during the Liner Puff Mode 504, a leak is detected during the Liner Check Mode 506, or a pressure fault is detected by the system during the Treat Mode 508, then the system may automatically default into entering the Disposal Mode 512.

In the event that the user pauses the system anytime during the Liner Puff Mode 504 or the Liner Check Mode 506, the system may enter into the Pause Mode 514 where the system releases pressure and waits indefinitely for the user to re-initiate the puff up sequence by initiating the system again. In the event that the user pauses the system anytime during the Treat Mode 508, the user may have a predetermined period of time, e.g., 15 seconds, to re-start treatment or the system may stop entirely. The time limit may be imposed so that the frozen tissue does not thaw significantly which could affect the ultimate depth of ablation. When treatment is re-started, the treatment time resumes from where it was paused.

Additionally and/or optionally, the processor or microcontroller may also be programmed to monitor the overall system. Hence, the system may be programmed to transmit a signal on a regular basis, e.g., every second, to a monitoring system. If the monitoring system fails to receive the signal, the entire system may be shut down such that the valves automatically close, the exhaust valve opens, and the pumps shut down.

Additional features may also be incorporated for safety. For instance, in order to prevent high pressure from developing within the uterus due to the accumulation of the cryogenic fluid or gas, safety features may be integrated into the system. Examples of some of the safety features may include: redundant, kink-resistant pressure lines and sensors to monitor intrauterine cavity pressure; flow rate-limited delivery line to minimize the amount of cryogenic fluid or gas introduced into the cavity in the event of a catastrophic failure; pressure relief valve in the exhaust flow path which opens if the primary path is obstructed; flexible yet crush-resistant, laser-cut, stainless steel exhaust tube within the liner; fail-safe solenoid valve on the cryogenic fluid or gas inflow path which closes in the event of a power failure or other control system failure; and/or software watchdog to safely shutdown the device in the event of a software malfunction.

Moreover, in order to prevent cryogenic fluid or gas in the exhaust from coming into contact with the physician or patient, additional safety provisions may also be implemented. Examples of some of these safety provisions may include: heat sink in the exhaust pathway to promote the conversion of cryogenic fluid or gas from liquid to gaseous states; and/or convoluted tube at the end of the exhaust path to further promote cryogenic fluid conversion from liquid to gaseous states and also prevent cryogenic fluid or gas from contacting the physician or patient.

As described herein, various visualization modalities may be utilized with any of the system variations described. For instance, hysteroscopic visualization may be accomplished by utilizing scope having, e.g., a 2.9 mm outer diameter and 39 cm length. Such a scope may be introduced through, e.g., the handle assembly 211, through a seal that interfaces with the scope and allows for the inflation of the liner with the scope in place if a more broad view of the cavity is desired. The scope may be removed before treatment is initiated.

Additionally and/or alternatively, ultrasound visualization may also be utilized to aid the user in the placement of the device within the cavity. During treatment, the cryogenic fluid or gas is visible under ultrasound as is the ice front.

While the treatment assembly may be comprised of a completely disposable handheld device which is provided sterile to the user, the cryogenic fluid or gas, e.g., liquid $N_2O$, may be contained in a canister which is integrated into the device. Alternatively, the assembly may be tethered to a reusable liquid $N_2O$ tank. Electronic components may be relocated from the handheld device to a reusable console which could also contain the liquid $N_2O$ tank. In another alternative, a simple disposable element of the system may attach to a reusable handle tethered to a liquid $N_2O$ tank. The reusable handle could be re-sterilizable and may contain the majority of the components normally contained within the disposable handle. The disposable element could consist of the flexible probe, liner, pressure-sensing lumens and the $N_2O$ delivery line.

While the system is described above for the cryoablative treatment of the uterine cavity, the system may also be used for other applications. For instance, the system may be utilized for shrinking or killing uterine fibroids where the probe may be inserted and the liner inflated with gas, as previously described, and a visualization element (ultrasound or hysteroscopy) may be used to position a freezing element up against the fibroid and freezing may be initiated. The freezing element may be positioned against the endometrial wall or may be inserted into the fibroid itself. The time of the freeze may be determined based upon the size of the fibroid with longer freezes for larger fibroids.

In addition to the initial positioning, the freeze may also be tracked using ultrasound, hysteroscopy or other visualization tools and stopped once a sufficient freeze has been achieved. The cryogen may be infused into a small balloon or liner inflated within the larger, gas-filled liner which may extract energy across both liners from the fibroid. The cryogen transmitting lumen can also be flexibly directed to the surface of the fibroid under visualization and the cryogen transmission balloon can be sized to best fit the endometrial surface of the fibroid and the freeze can be initiated and tracked under visualization. The small cryogen transmission balloon may also be replaced with a metal or other thermally conductive tip in which the cryogen undergoes a phase change and/or extracts energy. The gas-filled liner will allow for good visualization of the uterus and the freezing probe. In alternative variations, hyperthermal or other destructive energy may also be transmitted across the liner in order to destroy the fibroid with the liner simply acting as a source of controlled visualization without the introduction of saline or other distention media.

In yet another application, the system may be used to treat conditions such as Barrett's Esophagus. The probe may be inserted under endoscopic visualization and the liner sized to the length of the esophagus to be treated. The liner may then be inflated and visualization may be repeated across the liner to ensure optimal distention and contact with tissues to be treated. The cryogen delivery probe may then deliver a liquid cryogen or, preferably, a cold gas to the interior of the liner to treat the tissues adjacent to the liner. If needed or desired, the liner may then be deflated, repositioned and cryogen may be reinfused one or more times. This may be particularly the case for a relatively smaller esophagus in which the oversized liner may have more extreme folds which could prevent energy transmission. Repositioning and redeployment of the liner may allow for these folds to occur in different areas and will allow for a more consistent ablation. The use of cold gas may also allow for a more consistent, light ablation, as well, due to the smaller gradient in temperature and lack of the powerful phase change. Benefits of this design include the ability to prevent overlapping circumferential ablations which have been found to cause strictures and stenosis. Additional benefit can be found from the consistent treatment of all or part of the esophagus, including the gastroesophageal junction.

In yet another application, the system may be used to treat conditions such as treating benign prostatic hyperplasia (BPH) by shrinking the prostrate. The prostate tissue is sensitive to cryotherapy as evidenced by the efficacy of cryogenic freezing of the prostate for oncology. In this variation of the device, the liner may be placed in the urethra in the region of the prostate and cryogen may be infused (liquid or gas) into the liner. The energy may be transmitted across the wall of the liner and the urethra into the prostate causing apoptosis and death of the prostatic cells that are generating the symptoms of benign prostatic hyperplasia. The urethra may be temporarily stented open to allow for epithelialization without stricture formation either before or after the therapy. The stent could be configured to degrade over time, pass on its own and provide symptomatic relief and protection from urine during the healing period (i.e., be an occlusive barrier).

Due to the ease of visualization of the freeze, this therapy may also be conducted under direct visualization to ensure optimal freezing. This freeze may be stopped and/or restarted by the user, but may optimally be a programmed time or time at temperature. The therapy may also be performed without visualization in which case the freeze probe may be inserted with a location indicator (i.e., a balloon that is inflated in the bladder and drawn back to the urethral outlet) and therapy initiated once the correct position has been obtained.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A tissue treatment system for treating a contoured tissue surface, comprising:
   a handle having a housing;
   an elongate probe extending from the housing and having a distal tip and a flexible length;
   a liner expandably enclosing the probe and adapted to conform to the contoured tissue surface;
   at least one infusion lumen positioned through or along the elongate probe, wherein the infusion lumen defines one or more openings along its length; and
   a controller configured to:
      deliver a non-ablative fluid into the interior of the liner at a pressure to expand the liner to conform to the contoured tissue surface without deforming the contoured tissue surface;
      monitor a condition of the liner;
      deliver an ablative fluid into an interior of the liner via the infusion lumen;
      evacuate the ablative fluid from the liner.

2. The tissue treatment system of claim 1, where the controller is configured to monitor the condition of the liner by monitoring a pressure in the liner for a period of time.

3. The system of claim 2 wherein the controller is further configured to monitor the condition of the liner by detecting whether the pressure within the interior of the liner remains above a set pressure over a pre-determined period to determine whether a leak is present within the liner.

4. The tissue treatment system of claim 1, where ablative fluid comprises a cryoablative liquid.

5. The tissue treatment system of claim 4, where the controller is configured to evacuate the ablative fluid from the liner after the cryoblative liquid changes to a gas.

6. The tissue treatment system of claim 1, where delivering the ablative fluid into the interior of the liner occurs subsequent to monitoring the condition of the liner.

7. The system of claim 1 further comprising at least one delivery lumen slidingly positioned through or along the infusion lumen, wherein translation of the delivery lumen relative to the infusion lumen controls a number of unobstructed openings along the infusion lumen to control an ablative length of the liner.

8. The tissue treatment system of claim 1, where the non-ablative fluid comprises an ambient air.

9. The system of claim 8 wherein the controller is further configured to deliver the ambient air into the interior of the liner at a pre-determined pressure for a pre-determined period prior to infusing the ablative fluid.

10. The system of claim 1 wherein the controller is further configured to cease delivering the ablative fluid into the interior of the liner.

11. The system of claim 10 wherein the controller is further configured to infuse air into the interior of the liner while the ablative fluid remains within the interior and then vent the liner to thaw tissue in contact with an exterior of the liner.

12. The tissue treatment system of claim 1, where the liner comprises a tapered shape when expanded to conform to the contoured tissue surface to facilitate positioning in a tissue cavity.

13. A method of treating tissue, comprising:
   positioning an elongate probe into a body lumen to be treated;
   expanding a liner enclosing the probe into direct contact against the body lumen using a non-ablative fluid without deforming the body lumen;
   monitoring a fluid condition of the liner; and
   infusing an ablative fluid through a delivery lumen such that the fluid passes into an infusion lumen and into the liner to contact an interior of the liner.

14. The method of claim 13, further comprising adjusting a position of the delivery lumen relative to the infusion lumen which is positioned through or along the elongate probe such that one or more openings defined along a length of the infusion lumen remain unobstructed by the delivery lumen.

15. The method of claim 14, where infusing the ablative fluid through the delivery lumen further comprises maintaining the liner at a pressure of up to 150 mmHg and for a period of time of up to 150 seconds.

16. The method of claim 13, where monitoring the fluid condition of the liner comprises monitoring a pressure in the liner for a period of time.

17. The method of claim 13 further comprising detecting whether the pressure within the interior of the liner remains above 40 mmHg over a period of 5 seconds to determine whether a leak is present within the liner.

18. The method of claim 13 wherein infusing the ablative fluid is controlled via a controller.

19. The method of claim 13 further comprising ceasing the infusion of the ablative fluid into the interior of the liner.

20. The method of claim 13 wherein prior to infusing the ablative fluid, infusing an air into the interior of the liner at a pre-determined pressure and for a period of time.

21. The method of claim 13 further comprising detecting whether the pressure within the interior of the liner deviates by at least pre-determined pressure over a pre-determined period of time to determine whether a leak is present within the liner.

22. The method of claim 13 further comprising infusing an air into the interior of the liner at a pre-determined pressure while the ablative fluid remains within the interior and then venting the liner for a pre-determined about 2 seconds to thaw tissue in contact with an exterior of the liner.

* * * * *